(12) United States Patent
Berraondo Lopez et al.

(10) Patent No.: US 8,771,664 B2
(45) Date of Patent: Jul. 8, 2014

(54) COMPOSITIONS COMPRISING APOLIPOPROTEIN A POLYPEPTIDE AND INTERLEUKIN 15, AND METHODS OF TREATMENT USING THE SAME

(75) Inventors: Pedro Berraondo Lopez, Navarra (ES); Jessica Fioravanti, Pamplona (ES); Jose Medina Echeverz, Pamplona (ES); Ignacio Javier Melero Bermejo, Navarra (ES); Maria del Carmen Ochoa Nieto, Navarra (ES); Francisco de Asis Palazon Garcia, Navarra (ES); Silvia Bulfone-Paus, Borstel (DE); Erwin Hans Duitmann, Borstel (DE)

(73) Assignees: Fundacion para la Investigacion Medica Aplicada, Pamplona (Navarra) (ES); Research Center Borstel, Borstel (DE)

( * ) Notice: Subject to any disclaimer, the term of this patent is extended or adjusted under 35 U.S.C. 154(b) by 0 days.

(21) Appl. No.: 13/514,855

(22) PCT Filed: Dec. 10, 2010

(86) PCT No.: PCT/ES2010/070818
§ 371 (c)(1),
(2), (4) Date: Jun. 8, 2012

(87) PCT Pub. No.: WO2011/070214
PCT Pub. Date: Jun. 16, 2011

(65) Prior Publication Data
US 2012/0244118 A1    Sep. 27, 2012

(30) Foreign Application Priority Data

Dec. 11, 2009  (ES) ................................. 200931158
May 27, 2010  (ES) ................................. 201030813

(51) Int. Cl.
| | | |
|---|---|---|
| *A61K 38/20* | (2006.01) | |
| *C07H 21/04* | (2006.01) | |
| *C07K 14/54* | (2006.01) | |
| *C07K 14/775* | (2006.01) | |
| *C12N 5/00* | (2006.01) | |
| *C12P 21/02* | (2006.01) | |

(52) U.S. Cl.
USPC ...... 424/85.2; 435/69.5; 435/320.1; 435/325; 536/23.5; 530/350; 424/192.1

(58) Field of Classification Search
None
See application file for complete search history.

(56) References Cited

U.S. PATENT DOCUMENTS

2002/0156007 A1  10/2002  Graversen et al.
2008/0138394 A1  6/2008  Kim et al.

FOREIGN PATENT DOCUMENTS

GB  WO2008007146 A1  1/2008
WO  WO2005070400 A1  8/2005

OTHER PUBLICATIONS

Fioravanti et al, Hepatology 2011; vol. 53, pp. 1864-1873.*
Fioravanti et al, The Journal of Immunology, 2012, vol. 188, pp. 3988-3992.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, (Current Opinion in Structural Biology 2009, 19: 596-604.*
Ochoa et al, Cancer Research, vol. 73, No. 1, pp. 139-149.*
Ochoa et al, Cancer Research, Nov. 13, 2012; vol. 73, No. 1, pp. 139-149.*
International Search Report corresponding to PCT/ES2010/070818, May 13, 2011.
Bessard, Anne et al: "High antitumor activity of RLI, an interleukin-15 (IL-15)-IL-15 receptor alpha fusion protein, in metastic melanoma and colorectal cancer," Molecular Cancer Therapeutics, Sep. 2009, pp. 2736-2745.
Stoklasek, Thomas A. et al: "Combined IL-15/IL-15R alpha immunotherapy maximezes IL-15 activity in vivo," Journal of Immunology, vol. 177, No. 9, Nov. 2006, pp. 6072-6080.
Alexander J. J. et al: "Competitive inhibition of LDL binding and uptake by HDL in aortic endothelial cells," Journal of Surgical Research, Academic Press Inc., San Diego, CA, US, vol. 49, No. 3, Sep. 1, 1990, pp. 248-251.
Dubois Sigrid et al: "Preassociation of IL-15 with IL-15R alpha-IgG1-Fc enhances its activity on proliferation of NK and CD8(+)/CD44(high) T cells and its antitumor action," Journal of Immunology, vol. 180, No. 4, Feb. 2008, pp. 2099-2106.
Informe del Estado de la Tecnica corresponding to P200931158, Mar. 22, 2011.
Budagian et al., 2006, Cytokine & Growth Factor Reviews 17:259-80.
Cha et al., 2010, Breast Cancer Research and Treatment 122:359-69.
Chou et al., 2009, Veterinary Immunology and Immunopathology 130:25-34.
Duitman et al., 2008, Molecular and Cellular Biology 28:4851-61.
Hazama et al., 1999, British Journal of Cancer 80:1420-6.
Klebanoff et al., 2008, Proceedings of the National Academy of Science USA 101:1969-74.
Lin et al., 2008, Cancer Letters 272:185-95.

(Continued)

*Primary Examiner* — Bridget E Bunner
*Assistant Examiner* — Fozia Hamud
(74) *Attorney, Agent, or Firm* — Hoffmann & Baron, LLP

(57) ABSTRACT

The present invention relates to compositions capable of promoting both the innate immune response as well as the adaptive immune response in a subject based on the jointly use of ApoA, interleukin 15 and the Sushi domain of the IL15 receptor alpha chain, as well as to the use of these compositions for the stimulation of the immune response in a patient and to therapeutic methods for the treatment of infectious and neoplastic diseases.

22 Claims, 15 Drawing Sheets

(56) References Cited

OTHER PUBLICATIONS

Mortier et al., 2006, Journal of Biological Chemistry 281:1612-9.
Rubinstein et al., 2006, Proceedings of the National Academy of Science USA 103:9166-71.
Suzuki et al., 2001, Journal of Leukocyte Biology 69:531-7.
Zhang et al., 2009, Proceedings of the National Academy of Science USA 106:7513-8.

* cited by examiner

COMPOSITIONS COMPRISING APOLIPOPROTEIN A POLYPEPTIDE AND INTERLEUKIN 15, AND METHODS OF TREATMENT USING THE SAME

CROSS-REFERENCE TO RELATED APPLICATIONS

This application is the National Stage of International Application No. PCT/ES2010/070818, filed Dec. 10, 2010, which claims the benefit of Spanish Applications No. P200931158, filed Dec. 11, 2009, and P201030813, filed May 27, 2010, the contents of which are incorporated by reference herein.

FIELD OF THE INVENTION

The present invention relates to the field of immunology and, more specifically, the field of compositions capable of promoting both the innate immune response as well as the adaptive immune response of a subject. These compositions are useful for treating all diseases requiring greater immune system activity, such as tumours and infectious diseases.

BACKGROUND OF THE INVENTION

Interleukin 15 (IL15 or IL15) is a vital cytokine for the activity of NK, NKT cells and CD8 T memory lymphocytes. It performs its function through a receptor consisting of 3 subunits known as α, β and γ. Subunits β and γ are common to the IL-2 receptor. The α chain of the IL15 receptor is unique to IL15 and is necessary for the cytokine's release into the extracellular medium [Duitman, E. H., et al., Mol Cell Biol, 2008. 28:4851-61] and "presents" IL15 to subunits IL15Rβ and IL15Rγ.

Due to the stimulant properties of the immune system, this interleukin has anti-tumoral properties dependent on the presence of NK cells (Suzuki, 2001, J. Leuokoc. Biol., 69:531-537) and T cells (Hazama, 1999, Br. J. Cancer., 80:1420-1426, Meazza, 2000, Int. J. Cancer, 87:574-581 and Klebanoff, 2004, Proc. Natl. Acad. Sci. USA, 2004, 101: 1969-1974). IL15 is also involved in protection against viral infections and in the expansion and maintenance of a T cell-based response in immunisation and dendritic cell development.

Therefore, IL15 can be a useful therapeutic agent for treating diseases in which the immune system is involved. However, in vivo studies for the function of IL15 have been prevented partly due to the lack of availability of recombinant IL15 and to the low secretion level observed when IL15 is expressed from the native gene. Moreover, most cytokines have very low plasma half-lives given that they are produced in vivo in a local and transitory manner. Consequently, the use of IL15 in vivo requires the use of relatively high doses and frequent administration, resulting in different secondary effects which can result in cancer patients not tolerating the treatment.

With a view to overcoming these disadvantages, IL15 has been used in anti-tumoral therapy in combination with other treatments such as anti-CD40, IL-7 or IL-6 antibodies [Chou, P. C., et al., 2009, Vet Immunol Immunopathol, 130:25-34; Lin, C. Y., et al., Cancer Lett, 2008. 272(2): p. 285-95; Zhang, M., et al., Proc Natl Acad Sci USA, 2009, 106:7513-8 and Cha, E., et al., Breast Cancer Res Treat, 2009]. These combinations demonstrate a synergic effect making it possible to achieve similar effects with lower doses of IL15.

Another possibility for increasing IL 15 activity consists of co-administering it with a fusion protein that comprises the constant region of an immunoglobulin and the soluble region of the α chain of the IL 15 receptor, which produces a 50-fold increase in IL 15 activity (Rubinstein M. P. et al., 2006, Proc. Natl. Acad. Sci. USA, 103:9166-71 and Stoklasek T. A. et al., 2006, J. Immunol.; 177:6072-80).

Recently, it has been demonstrated that a polypeptide formed by amino acids 1 to 77 of the amino terminus end of the IL15 receptor α chain (the so-called "sushi domain") is an agonist of IL15 [Mortier, E., et al., J Biol Chem, 2006. 281(3): p. 1612-9]. Thus, the administration of a fusion protein containing said domain and IL15 shows a greater antitumoral effect than that of IL15 resulting in a 65% decrease in lung metastasis of the B16F10 tumour and a reduction in the number of metastases of the HCT-116 human tumour implanted in the caecum of nude mice [Bessard, A., et al., Mol Cancer Ther, 2009. 8(9): p. 2736-45].

Another alternative to achieve improving the effect of IL15 without incurring in unwanted secondary effects consists of modifying the molecule with a view to increasing its half life. Thus, US2006257361 describes fusion proteins comprising the constant region of an immunoglobulin and IL15 presenting half lives in serum following administration higher than unmodified IL15.

Nonetheless, there is a need in the state of the art for alternative formulations of IL15 wherein the protein maintains its immune response-promoting activity but allows IL 15-related secondary effects to be reduced as much as possible.

SUMMARY OF THE INVENTION

In a first aspect, the invention relates to a composition comprising, jointly or separately,
(i) a first component selected from the group of
  (a) a polypeptide comprising an Apo A polypeptide or a functionally equivalent variant thereof having at least 70% identity to said Apo A polypeptide and
  (b) a polynucleotide encoding an Apo A polypeptide or a functionally equivalent variant thereof having at least 70% identity to said Apo A polypeptide and
(ii) a second component selected from the group of
  (a) IL15 or a functionally equivalent variant thereof having at least 70% identity to IL15 and
  (b) a polynucleotide encoding IL15 or a functionally equivalent variant thereof having at least 70% identity to IL15 and
(iii) a third component selected from the group of
  (a) the Sushi domain of the IL15 receptor alpha chain or a functionally equivalent variant thereof having at least 70% identity to the Sushi domain of the IL15 receptor alpha chain and
  (b) a polynucleotide encoding the Sushi domain of the IL15 receptor alpha chain or a functionally equivalent variant thereof having at least 70% identity to the Sushi domain of the IL15 receptor alpha chain.

In a second aspect, the invention relates to a fusion protein comprising
(i) a region A formed by an Apo A polypeptide or a functionally equivalent variant thereof having at least 70% identity to said Apo A polypeptide,
(ii) a region B formed by IL15 or a functionally equivalent variant thereof having at least 70% identity to IL15 and
(iii) a region C formed by the Sushi domain of the IL15 receptor alpha chain or a functionally equivalent variant thereof having at least 70% identity to the Sushi domain of the IL15 receptor alpha chain.

In further aspects, the invention relates to a polynucleotide encoding a fusion protein of the invention, to a vector or gene construct comprising a polynucleotide of the invention, to a host cell comprising a fusion protein of the invention, to a polynucleotide of the invention, to a vector of the invention or to a gene construct of the invention.

In another aspect, the invention relates to a pharmaceutical composition comprising a composition of the invention, a fusion protein of the invention, a polynucleotide of the invention, a vector or gene construct of the invention, a host cell of the invention, and a pharmaceutically acceptable vehicle.

In another aspect, the invention relates to an in vitro method for promoting antigen-specific T-lymphocyte expansion which comprises contacting a lymphocyte population previously exposed in vivo to said antigen, with a composition of the invention, a fusion protein of the invention, a polynucleotide of the invention, a vector or gene construct of the invention, a host cell of the invention.

In addition, the invention relates to a composition of the invention, a fusion protein of the invention, a polynucleotide of the invention, a vector or gene construct of the invention, a host cell of the invention for use in medicine or for the treatment of diseases that require stimulation of a subject's immune response.

DETAILED DESCRIPTION OF THE INVENTION

Figure 1:
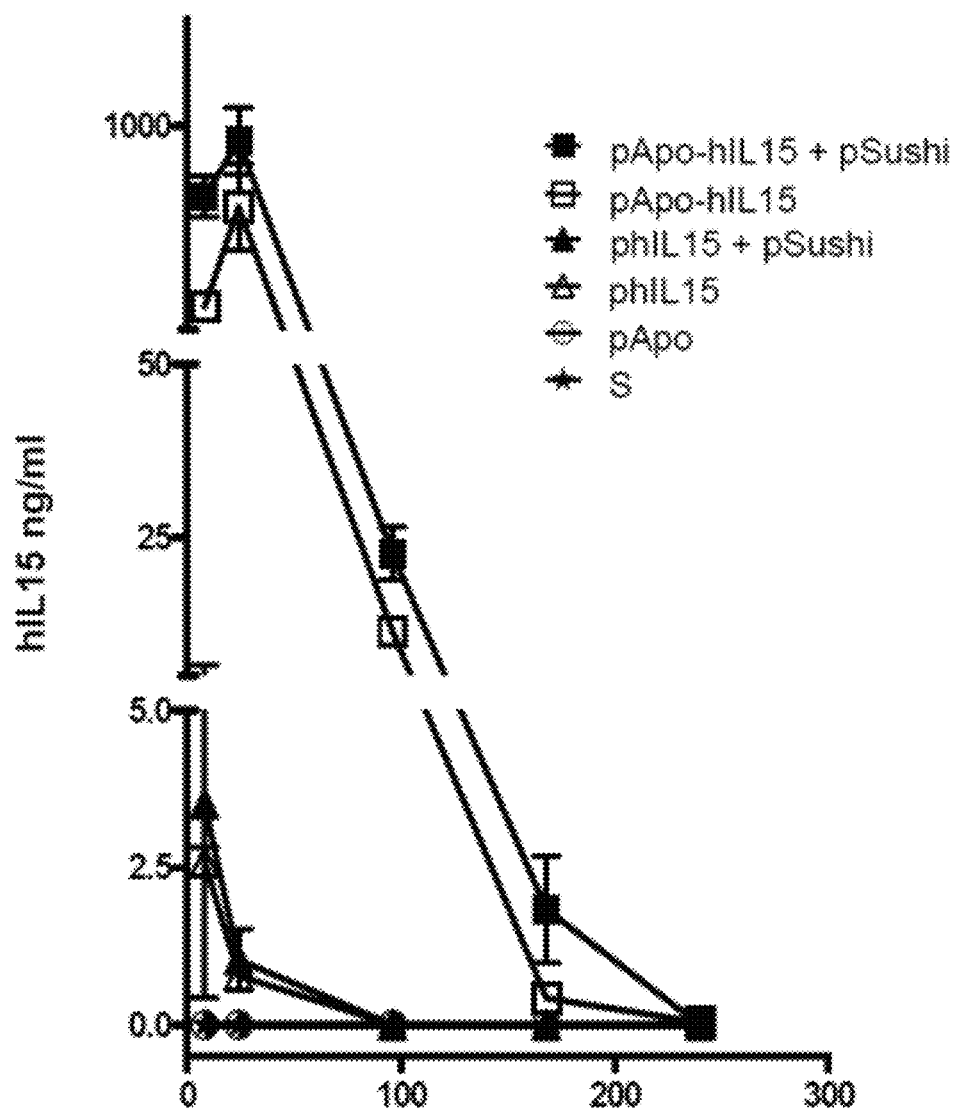
FIG. 1. Expression kinetics of hIL15 (ng/mL) in time t (h: hours). Groups of C57B16 mice received a hydrodynamic injection of plasmids, pApo-hIL15 +pSushi, pApo-hIL15, phIL15+pSushi, phIL15, pApo or saline (S). At 8, 24, 96, 168 and 240 hours blood was extracted and serum concentration of hIL15 was analysed by ELISA assay. The mean and mean standard deviation of a representative experiment with 2-3 animals per group is shown. The results were statistically compared by repeated measurement ANOVA, followed by a Bonferroni test. Significant differences are observed between hIL15 levels at 8 and 24 hours of the group treated with pApo-hIL15 in contrast to other groups ($p<0.001$).

The authors of the present invention have observed that, surprisingly, the co-administration of a nucleic acid encoding a fusion protein comprising IL15 fused to the ApoA protein together with the sushi domain of the IL15 receptor α chain (hereinafter IL15αR-sushi) produces a higher IL15 activity than that observed when IL15 and IL15αR-sushi are administered jointly. Said higher activity is the result of not only higher and longer lasting circulating levels of IL15 obtained as observed in example 3 of the present invention, but also of the capacity to induce CTLL2 cell proliferation (example 4 of the present invention), the capacity to promote the proliferation of intrasplenic CD8 T lymphocytes and CD8 T memory cells, CD8 T intrahepatic lymphocytes and blood CD8 T lymphocytes (example 5 of the present invention) as well as a higher antitumoral effect in two experimental tumour models (example 7 of the present invention) and anti-metastatic effect (example 8 of the present invention).

Without wanting to be bound by any theory, it is believed that the synergic effect resulting from the administration of IL15 in the form of a fusion protein with ApoA is a result of IL15 action in target tissues that express ApoA receptors on their surface, in such a way that IL15 can perform its effect on different or complementary tissues to those believed until now. This hypothesis is sustained on the synergic effect also observed in mice deleted of the gene for the α receptor of IL15.

More surprisingly still is the observation that the administration of a nucleic acid encoding and allowing the expression of a triple fusion protein comprising the ApoA1 protein fused to IL15 and IL15αR-sushi produces a proliferation of CD8 lymphocytes and NK cells far higher than that obtained with the administration of a nucleic acid encoding IL15, either alone or in combination with another encoding IL15αR-sushi, or with a nucleic acid encoding the fusion protein of ApoA1 with IL15, either alone or in combination with another encoding IL15αR-sushi.

Compositions of the Invention

Thus, in a first aspect, the invention relates to a composition comprising, jointly or separately,
(i) a first component selected from the group of
 (a) a polypeptide comprising an Apo A polypeptide or a functionally equivalent variant thereof having at least 70% identity to said Apo A polypeptide and
 (b) a polynucleotide encoding an Apo A polypeptide or a functionally equivalent variant thereof having at least 70% identity to said Apo A polypeptide and
(ii) a second component selected from the group of
 (a) IL15 or a functionally equivalent variant thereof having at least 70% identity to IL15 and
 (b) a polynucleotide encoding IL15 or a functionally equivalent variant thereof having at least 70% identity to IL15 and (iii) a third component selected from the group of
(c) the Sushi domain of the alpha chain of the IL15 receptor or a functionally equivalent variant thereof having at least 70% identity to the Sushi domain of the alpha chain of the IL15 receptor and
(d) a polynucleotide encoding the Sushi domain of the alpha chain of the IL15 receptor or a functionally equivalent variant thereof having at least 70% identity to the Sushi domain of the alpha chain of the IL15 receptor.

The term "composition" as used in the present invention refers to a composition of material comprising the indicated components, in other words, the polypeptide Apo A, IL15 and the Sushi domain of the IL15 receptor alpha chain as well as any other product resulting directly or indirectly from the combination of the different components in any quantities thereof. The expert in the art will appreciate that the composition may be formulated as a single formulation or may be presented as a formulation of each one of the components separately so that they can be combined for joint use in the form of a combined preparation. The composition may be a kit of parts wherein each component is separately formulated and packaged.

The term "protein", used herein indiscriminately with polypeptide, refers to a chain of amino acids of any length wherein the different amino acids are joined together by peptide bonds or disulphide bridges.

The term "polynucleotide", as used in the present invention, relates to a polymer formed by a variable number of monomers wherein the monomers are nucleotides, including ribonucleotides as well as deoxyribonucleotides. The polynucleotides include monomers modified by methylation as well as unmodified forms. The terms "polynucleotide" and "nucleic acid" are used indiscriminately in the present invention and include mRNA, cDNA and recombinant polynucleotides. As used in the present invention, polynucleotides are not limited to polynucleotides as they appear in nature, and also include polynucleotides where unnatural nucleotide analogues and inter-nucleotide bonds appear. Non-limitative examples of this type of unnatural structures include polynucleotides wherein the sugar is different from ribose, polynucleotides wherein the phosphodiester bonds 3'-5' and 2'-5' appear, polynucleotides wherein inverted bonds (3'-3' and 5'-5') appear and branched structures. Also, the polynucleotides of the invention include unnatural inter-nucleotide bonds such as peptide nucleic acids (PNA), locked nucleic acids (LNA), C1-C4 alkylphosphonate bonds of the methylphosphonate, phosphoramidate, C1-C6 alkylphosphotriester, phosphorothioate and phosphorodithioate type. In any case, the polynucleotides of the invention maintain the capacity to hybridise with target nucleic acids in a similar way to natural polynucleotides.

First Component of the Composition of the Invention

The first component of the invention is selected from the group of an Apo A polypeptide or a functionally equivalent variant thereof and a nucleic acid encoding an Apo A polypeptide or a functionally equivalent variant thereof.

The term "ApoA polypeptide", as used in the present invention relates to any member of the Apo A family forming part of the high density lipoproteins (HDL) and that is capable of interacting specifically with receptors on the surface of liver cells thereby guaranteeing its capacity to transport the molecules of interest to this organ joined to the aforesaid Apo A protein. Preferably, the Apo A molecules that can be used in the present invention are selected from the group of ApoA-I, ApoA-II, ApoA-III, ApoA-IV and ApoA-V or of functionally equivalent variants thereof.

In a preferred embodiment, the Apo A protein that is used in the present invention is the protein ApoA-I. ApoA-I is understood, in the context of the present invention, as the mature form of the pre-proApoA-I protein which forms part of high density lipoproteins (HDL). ApoA-I is synthesised as a precursor (pre-proApoA-I) containing a secretion signal sequence that is eliminated to make way for the precursor. The signal sequence consists of 18 amino acids, the propeptide of 6 and the mature form of the protein of 243 amino acids. Preferably the mature protein form is used lacking the peptide signal and processed. In a preferred embodiment, the ApoA-I protein is of human origin and its amino acid sequence is the one shown in SEQ ID NO:1 (UniProt accession number P02647). In another preferred embodiment, protein ApoA-I is of murine origin, in particular of mouse, and its amino acid sequence is the one shown in SEQ ID NO:2 (UniProt accession number Q00623). In another preferred embodiment, the ApoA-1 protein is of murine origin, in particular of rat, and its amino acid sequence is the one shown in SEQ ID NO:3 (UniProt accession number PO4639).

"Functionally equivalent variant of ApoA-I" is understood as meaning all those polypeptides resulting from the insertion, substitution, or deletion of one or more amino acids of the abovementioned ApoA-I sequence substantially maintaining intact their capacity to interact with the so-called "scavenger receptor class B type I" (SR-BI) forming the HDL receptor present in liver cells. The capacity to interact with the HDL receptor is determined essentially as described by Monaco et al (EMBO J., 1987, 6:3253-3260) either through ApoA-I binding studies to the membrane of hepatocytes or through the determination of ApoA-I or its variant's capacity to inhibit HDL bonding to the receptors of hepatocyte membranes. Preferably, the dissociation constant of the ApoA-I variant bond to hepatocyte membranes is at least $10^{-8}$ M, $10^{-7}$ M, $10^{-6}$ M, $10^{-5}$ M or $10^{-4}$ M.

ApoA-I variants contemplated in the context of the present invention include polypeptides showing at least 70%, 72%, 74%, 76%, 78%, 80%, 90%, or 95% similarity or identity with ApoA-I polypeptides. The degree of identity between two polypeptides is determined using computer-implemented algorithms and methods extensively known by experts in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

Preferably, the ApoA-I variants used in the context of the invention present a high serum half-life in relation to the ApoA-I mentioned above, making it possible to reach serum levels of ApoA-I higher than those observed with ApoA-I. Methods for determining the serum half life of a protein and, in particular of ApoA-I, are known in the art and include, among others, using methods based on metabolic labelling with marked proteins described by Eisenberg, S. et al (J. Lipid Res., 1973, 14:446-458), by Blum et al. (J. Clin. Invest., 1977, 60:795-807) and by Graversen et al (J Cardiovasc Pharmacol., 2008, 51:170-177). An example of said variants showing a higher half-life is, for example, the variant known as Milano (which contains the R173C mutation).

The first component of the invention can be a nucleic acid that encodes at least one of the ApoA and Apo A variants mentioned above. Thus, in the case of the nucleic acid encoding ApoA, it may be of human origin corresponding to the sequence with NCBI accession number X02162 (SEQ ID NO:4), of murine origin corresponding to the sequence with NCBI accession number X64262 (SEQ ID NO:5), of rat corresponding to the sequence with NCBI accession number M00001 (SEQ ID NO:6).

The expert in the art will appreciate that the nucleic acid forming the first component of the invention needs to be expressed inside the cell and eventually secreted into the medium, wherefore, the sequence encoding ApoA or a functionally equivalent variant thereof may present at a 5' end, a sequence encoding a secretion signal. The expression "secretion signal sequence", as used in the present invention, refers to an amino acid sequence capable of promoting access to the cell secretory pathway for all those proteins presenting said sequence in their N-terminal end. Suitable signal sequences for use in the present invention include, among others, the signal sequence of tissue plasminogen activator (tPA), of the growth hormone, GM-CSF and of immunoglobulins and, in particular, of Igκ or of IgV$_χ$. Preferably, the signal sequence forming part of the component A of the invention is the signal sequence of Apo A itself as defined previously.

Alternatively, the first component of the invention may be a nucleic acid showing a sequence identity of at least 70%, at least 75%, at least 80%, at least 85%, at least 90%, at least 91%, at least 92%, at least 93%, at least 94%, at least 95%, at least 96%, at least 97%, at least 98% or at least 99% with any of the abovementioned sequences wherein the percentage of identity is determined by using an algorithm of the GAP, BESTFIT or FASTA type whose computer implementation appears in the Wisconsin Genetics Software Package Release 7 (Wisconsin Genetics Software Package Release 7.0, Genetics Computer Group, 575 Science Dr., Madison, Wis.) and which uses the local algorithms of Smith and Waterman (Adv. Appl. Math., 1981, 2:482), of Needleman and Wunsch (J. Mol. Biol. 1970, 48: 443) or of Pearson and Lipman (Proc. Natl. Acad. Sci. (U.S.A.), 1988, 85:2444) using the default values for the different parameters.

Alternatively, the first component of the composition of the invention is a polynucleotide encoding ApoA or a variant thereof capable of hybridising specifically with any of the native sequences corresponding to ApoA of different previously defined mammals. "Polynucleotides capable of hybridising specifically with a target polynucleotide" is understood, in the context of the present invention, as meaning those polynucleotides capable of hybridising in strict conditions, strict conditions understood as meaning the conditions that allow specific hybridisation of two nucleic acids at temperatures of approximately 65° C. for example, in a solution of 6×SSC, 0.5% SDS, 5% Denhardt solution and unspecified denatured DNA at a concentration of 100 µg/ml any other solution with an equivalent ionic strength and following a stage of washing at 65° C. in the presence of a solution of, for example 0.2% SSC and 0.1% SDS and any other solution with an equivalent ionic strength. Nevertheless, the strict conditions may be adapted by the expert in the art according to the size of the sequence to be hybridised, according to the content in GC and according to other parameters. Suitable methods for selecting the appropriate hybridisation conditions have been described by Sambrook et al., 2001 (Molecular Cloning: A Laboratory Manual, 3$^{rd}$ Edition, Laboratory Press, Cold Spring Harbor, N.Y.).

Second Component of the Composition of the Invention

The second component of the invention is selected from the group of IL15 or a functionally equivalent variant thereof and of a nucleic acid encoding IL15 or a functionally equivalent variant thereof.

The term "IL15" or "IL-15", as used in the present invention, refers to a cytokine whose isolation, cloning and sequence is described in Grabstein et al. (U.S. Pat. No. 5,747,024 and Grabstein et al., 1994, *Science* 246: 965-968). The term IL15 includes any polypeptide form with the amino acid sequence of a natural IL15. Examples of IL15 that may be used forming part of the compositions and fusion proteins of the present invention include, IL15 of rodents (mouse, rat, hamster), human, primate, canine, feline, porcine, equine, bovine, ovine, and similar. IL 15 polypeptides of mammals that can form part of the compositions and fusion proteins of the invention include, without limitation, IL15 of human origin and whose amino acid sequence is the one shown in P40933 (SEQ ID NO: 7); mouse IL15 whose amino acid sequence is shown in P48346 (SEQ ID NO:8), rat IL15 whose amino acid sequence is shown in P97604 (SEQ ID NO:9), cat IL15 whose amino acid sequence is shown in O97687 (SEQ ID NO:10) and bovine IL15 whose amino acid sequence is the one shown in Q28028 (SEQ ID NO:11).

"Functionally equivalent variant of IL15" is understood as meaning all those polypeptides resulting from the insertion, substitution or deletion of one or more amino acids from any of the abovementioned sequences of IL15 and that maintain substantially intact at least one of the functions of IL15, wherein said function is selected from:

the capacity to promote the proliferation of CD8+ T cells determined, for example, by the method described by Montes, et al, (Clin. Exp. Immunol., 2005, 142:292-302) based on the incubation of a population of peripheral blood mononuclear cells with an antigen peptide in the presence of the variant of IL15 followed by the determination of the percentage of cells that can be labelled with specific antibodies against CD8, the capacity to promote the activation of NK cells after being presented in trans by the dendritic cells. This capacity may be determined by measuring the incorporation of tritiated thymidine on the part of the CD56+ NK cells in the presence of IL15 or by measuring the NK cell secretion of the GM-CSF cytokine. Methods for determining both IL15 functionalities have been described by Carson, W. et al. (J. Exp. med., 1994, 180:1395-1403), macrophages and neutrophils.

The capacity of IL15 to inhibit Fas-mediated apoptosis in B-cell precursors, as described by Demirci et al. (Cell Mol Immunol. 2004, 1:123-8.), which can be determined using standard techniques for determining apoptosis such as TUNEL or the determination of DNA fragmentation by gel electrophoresis and ethidium bromide staining.

Variants of IL15 contemplated in the context of the present invention include polypeptides showing at least 70%, 72%, 74%, 76%, 78%, 80%, 90%, or 95% of similarity or identity with the IL15 polypeptides of the mammals mentioned above. The degree of identity between two polypeptides is determined using computer-implemented algorithms and methods that are extensively known to experts in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

The second component of the invention can be a nucleic acid encoding at least one of the native IL15 and variants of IL15 mentioned above. The nucleic acids encoding mammal IL15 can be recovered from nucleic acid repositories and include, without limitation, polynucleotides whose sequences are defined by accession numbers U14407 (human, SEQ ID NO:12), U14332 (mouse, SEQ ID NO:13), U69272 (rat, SEQ ID NO:14), AF108148 (cat, SEQ ID NO:15) and U42433 (bovine, SEQ ID NO:16).

Said polynucleotides include those that show a sequence identity of at least 70%, at least 75%, at least 80%, at least 85%, at least 90%, at least 91%, at least 92%, at least 93%, at least 94%, at least 95%, at least 96%, at least 97%, at least 98% or at least 99% identity with any of the aforesaid sequences wherein the percentage of identity is determined by using one of the algorithms mentioned above.

Alternatively, the polynucleotides forming the second component of the invention are polynucleotides capable of hybridising specifically with the previously defined polynucleotides. Methods for determining a polynucleotide's capacity to hybridise specifically with a target sequence have been described in detail in the context of the first component of the invention.

The expert in the art will appreciate that the nucleic acid forming the second component of the invention can be found operatively bound to a signal sequence allowing secretion into the medium of the IL15 or functionally equivalent variant. Suitable signal sequences for use in the present invention include those mentioned previously in the context of the first component of the invention. Preferably, the signal sequence forming part of the second component of the composition of the invention is the signal sequence of IL15 itself as previously defined or the signal sequence of one of the immunoglobulins, in particular IgK or IgV$_\chi$.

Third Component of the Composition of the Invention

The third component of the invention is selected from the group of the sushi domain of the IL15 receptor alpha chain or a functionally equivalent variant thereof.

The expression "sushi domain of the IL15 receptor alpha chain" (hereinafter IL15Rα-sushi), as used in the present invention, refers to an amino acid sequence that appears in the extracellular region of the IL15 receptor alpha chain and that corresponds to the sequence beginning with the first cysteine to appear in the first exon of the gene of the IL15 receptor alpha chain and ending with the cysteine encoded by exon 4 of the gene of the IL15 receptor alpha chain. Alternatively, the sushi domain is defined as the sequence starting in the first cysteine residue of the IL15 receptor alpha chain after the signal sequence and ending with the fourth cysteine residue after the signal sequence in the aforesaid sequence. Suitable sushi domains for use in the present invention include the sushi domain from the human origin IL15 receptor alpha chain, corresponding to the sequence with UniProt accession number NP_002180 and whose Sushi domain corresponds to the sequence

```
                                      (SEQ ID NO: 17)
CPPPMSVE HADIWVKSYS LYSRERYICN SGFKRKAGTS

SLTECVLNKA TNVAHWTTPS LKC
``` and the sushi domain from the mouse IL15 receptor alpha chain corresponding to the sequence with Swiss-Prot accession number Q60819 and whose Sushi domain corresponds to the sequence

```
                                      (SEQ ID NO: 18)
CPPPV SIEHADIRVK NYSVNSRERY VCNSGFKRKA GTSTLIECVI

NKNTNVAHWT TPSLKC;
```

"Functionally equivalent variant of the sushi domain of the IL15 receptor alpha chain" is understood as meaning all those polypeptides resulting from the insertion, substitution or deletion of one or more amino acids of the sequence of any of the sequences of human origin or murine sushi domains mentioned previously and that maintain substantially intact their capacity to bind to IL15 and increase the proliferative effect of IL15 in cells expressing the low affinity IL15 receptor (for example, cells from Mo-7e or 32Dβ lines) as described by Mortier et al. (J. Biol. Chem., 2006, 281:1612-1619).

Variants of IL15Rα-sushi contemplated in the context of the present invention include polypeptides showing at least 70%, 72%, 74%, 76%, 78%, 80%, 90%, or 95% similarity or identity with the polypeptides mentioned above. The degree of identity between two polypeptides is determined using computer-implemented algorithms and methods extensively known to experts in the art. The identity between two amino acid sequences is determined preferably by using the BLASTP algorithm (BLAST Manual, Altschul, S. et al., NCBI NLM NIH Bethesda, Md. 20894, Altschul, S., et al., J., 1990, Mol. Biol. 215:403-410).

The third component of the invention may be a nucleic acid encoding at least one sushi domain of the IL15 receptor alpha chain, native and variants thereof as mentioned previously. The nucleic acids encoding mammal IL15Rα-sushi can be recovered from the sequences of the corresponding alpha chains found in the nucleic acid repositories and include, without limitation, the sequences encoding IL15Rα-sushi of the human IL15 receptor alpha chain (NCBI accession numbers corresponding to U31628, SEQ ID NO:19) and mouse (NCBI accession number: U22339, SEQ ID NO:20).

Said polynucleotides include those showing a sequence identity of at least 70%, at least 75%, at least 80%, at least 85%, at least 90%, at least 91%, at least 92%, at least 93%, at least 94%, at least 95%, at least 96%, at least 97%, at least 98% or at least 99% identity with any of the abovementioned sequences wherein the percentage of identity is determined using any of the previously mentioned algorithms.

Alternatively, the polynucleotides forming the third component of the invention are polynucleotides capable of hybridising specifically with the polynucleotides defined previously. Methods for determining a polynucleotide's capacity to hybridise specifically with a target sequence have been described in detail in the context of the invention's first component.

The expert in the art will appreciate that the nucleic acid forming the second component of the invention may be found operatively bound to a signal sequence allowing secretion into the medium of the sushi domain or of its functionally equivalent variant. Suitable signal sequences for use in the present invention include those mentioned previously in the context of the first component of the composition of the invention. Preferably, the signal sequence forming part of the second component of the composition of the invention is the signal sequence of the IL15 receptor alpha chain itself as previously defined or the signal sequence of one of the immunoglobulins, in particular, of IgK or of IgV$_\chi$.

In a preferred embodiment, the third component of the compositions of the invention is a polynucleotide comprising or consisting of the sequence identified as SEQ ID NO: 21 and that encodes a polypeptide comprising the Sushi domain of the human IL15RA receptor, preceded by its own signal peptide (SEQ ID NO: 22).

The compositions of the invention may be formed by polypeptides or polynucleotides from different species. Nonetheless, in a preferred embodiment the three components originate from the same animal species. In a preferred embodiment, the three components are of human origin. In another preferred embodiment, the three components are of murine origin.

Compositions Wherein the First and Second Component Form a Single Molecule

The authors of the present invention have observed that it is possible to obtain the synergic effect on the antitumoral activity of IL15 when the first and the second component of the composition of the invention form part of a single molecule. In this case, the compositions of the invention are binary compositions formed by a first component that in turn comprises the first and second component defined above, and a second component, which corresponds to the third component defined above. The expert in the art will appreciate that if the first and second components of the composition are polypeptides, said single molecule is a fusion protein comprising (i) an Apo A polypeptide or functionally equivalent variant thereof and (ii) IL15 or a functionally equivalent variant thereof.

The term "fusion protein", as used in the present invention, refers to polypeptides comprising two or more regions from different or heterologous proteins.

Alternatively, in the case of both the first and second components of the composition being polynucleotides, said single molecule is a polynucleotide encoding a fusion protein comprising (i) a polypeptide comprising an Apo A polypeptide or a functionally equivalent variant thereof and (ii) IL15 or a functionally equivalent variant thereof.

In this case, when the first and second components are of a peptidic nature, the invention contemplates compositions wherein the first component is in the N-terminal position in relation to the second component, and compositions wherein the first component is in the C-terminal position in relation to the second component.

In the case of the first and second components being of a polynucleotidic nature, the invention contemplates compositions wherein the first component is in position 5' in relation to the second component, and compositions wherein the first component is in position 3' in relation to the second component.

In both cases, it is possible for the first and second component to be associated directly, in other words, the C-terminal end of the first component is associated to the N-terminal end of the second component, or the C-terminal end of the second component is associated to the N-terminal end of the first component, or the 3' end of the first component is associated to the 5' end of the second component and compositions wherein the 3' end of the second component is associated to the 5' end of the first component.

Alternatively, in another aspect, the invention contemplates compositions wherein the fusion of the first and second component is carried out through a peptide linker (in the case of the first and second component being of a polypeptidic nature) or through a sequence encoding a peptide linker (in the case of the first and second component being of a polynucleotidic nature).

The term "peptide linker", "linker", "connector", "spacer" or its grammatical equivalents, as used in the present invention, refers to a molecule that connects two molecules and that frequently allows connected molecules to acquire a functional configuration. The linker peptide preferably comprises at least two amino acids, at least three amino acids, at least five amino acids, at least ten amino acids, at least 15 amino acids, at least 20 amino acids, at least 30 amino acids, at least 40 amino acids, at least 50 amino acids, at least 60 amino acids, at least 70 amino acids, at least 80 amino acids, at least 90 amino acids or approximately 100 amino acids.

Suitable linkers for use in the present invention include:
Linkers comprising 2 amino acids or more selected from the group consisting of glycine, serine, alanine and threonine such as, without limitation the linkers of sequence SGGTSGSTSGTGST (SEQ ID NO:23), AGSSTGSSTGPGSTT (SEQ ID NO:24), GGSGGAP (SEQ ID NO:25) and GGGVEGGG (SEQ ID NO: 26) described by Muller, K. M. et al. (Methods. Enzimology, 2000, 328: 261-281).

Linkers based on residues 53-56 of tetranectin, which form a β sheet in tetranectin, and residues 57-59 which form a turn in tetranectin (Nielsen, B. B. et al., FEBS Lett. 412: 388-396, 1997) such as the linker of sequence GTKVHMK (SEQ ID NO:27), Linkers based on a subsequence of the linker sheet 3 of human fibronectin, corresponding to amino acids 1992-2102 such as the linker PGTSGQQPSVGQQ (SEQ ID NO: 28) corresponding to amino acids number 2037-2049, and within that subsequence fragment GTSGQ (SEQ ID NO: 29) corresponding to the residues of amino acids 2038-2042 is more preferable.

Linker based on the sequence of 10 residues of amino acids of the upper hinge region of murine IgG3 such as the linker of sequence PKPSTPPGSS (SEQ ID NO: 30) which has been used for the production of dimeric antibodies by means of a coiled helix (Pack P. and Pluckthun, A., 1992, Biochemistry 31:1579-1584), Linker peptide of sequence APAETKAEPMT (SEQ ID NO:31)

Linker peptide of sequence GGSGGGGSGGGSGGGGSLQ (SEQ ID NO:32)

Linker peptide of sequence GAP.

Alternatively, the two components of the conjugates of the invention can be connected by a peptide whose sequence contains a cleavage target for a protease, thereby allowing separation of ApoA-I from component (ii). Suitable protease cleavage sites for incorporation into the polypeptides of the invention include enterokinase (cleavage site DDDDK SEQ ID NO: 33), Xa factor (cleavage site IEDGR, SEQ ID NO:34), thrombin (cleavage site LVPRGS, SEQ ID NO:35), TEV protease (cleavage site ENLYFQG, SEQ ID NO:36), PreScission protease (cleavage site LEVLFQGP, SEQ ID NO:37), inteins and similar. In a preferred embodiment, the cleavage site is that of a protease expressed in tumoral tissues, inflamed tissues or in the liver in such a way that separation of Apo A and component (ii) takes place once the conjugate has reached the liver. In a preferred embodiment, the linker contains a matrix metalloproteinase 9 recognition site (cleavage site LFPTS, SEQ ID NO: 38).

Although the invention has been exemplified with compositions wherein both the component resulting from the fusion of the first and second component (the fusion protein of Apo A with IL15) and the third component (the Sushi domain of the IL15 receptor α chain) are used in the form of a nucleic acid, the invention is not limited to compositions wherein both components are nucleic acids and rather contemplates, as alternatives, compositions wherein the first and/or second component are polypeptides. Thus, the invention contemplates compositions formed by:

A polypeptide comprising a fusion protein formed by Apo A and IL15 and a polypeptide comprising the sushi domain of the IL15 receptor α chain.

A polypeptide comprising a fusion protein formed by Apo A and IL15 and a polynucleotide encoding a polypeptide comprising the sushi domain of the IL15 receptor α chain.

A polynucleotide encoding a polypeptide comprising a fusion protein formed by Apo A and IL15 and a polypeptide comprising the sushi domain of the IL15 receptor α chain.

A polynucleotide encoding a polypeptide comprising a fusion protein formed by Apo A and IL15 and a polynucleotide encoding a polypeptide comprising the sushi domain of the IL15 receptor α chain.

The ratio between the components forming part of the compositions of the invention will depend on the inductor agent of the first and second component used in each particular case, as well as the required use. Thus, the invention contemplates compositions wherein the ratio between the amounts of the two components can range between 50:1 and 1:50, in particular between 20:1 and 1:20, between 1:10 and 10:1, or between 5:1 and 1:5.

In the case of compositions wherein the first and second component form a single molecule, each one of the components may come from a different species, although it is preferred for the components forming part of a single molecule to come from the same species. Thus, in a preferred embodiment, Apo A or the functionally equivalent variant thereof is of human origin and IL15 or the functionally equivalent variant thereof is of human origin. In another preferred embodiment, Apo A or the functionally equivalent variant thereof is of murine origin and IL15 or the functionally equivalent variant thereof is of murine origin.

In a preferred embodiment, the single molecule forming the first component of the composition is formed by the human origin ApoAI polypeptide and human origin IL15, separated by a linker presenting the GAP sequence. The polynucleotide encoding said fusion presents a sequence identified in the present invention as SEQ ID NO: 39.

In another preferred embodiment, the single molecule forming the first component of the composition is formed by the murine origin ApoAI polypeptide and human origin IL15, separated by a linker presenting the GAP sequence. The polynucleotide encoding said fusion presents a sequence identified in the present invention as SEQ ID NO: 40.

In another preferred embodiment, the single molecule forming the first component of the composition is formed by the murine origin ApoAI polypeptide and murine origin IL15, separated by a linker presenting the GAP sequence. The polynucleotide encoding said fusion presents a sequence identified in the present invention as SEQ ID NO: 41.

The polypeptide comprising the Sushi domain of the IL15 receptor alpha chain or the functionally equivalent variant thereof may be of human origin or murine origin. Nonetheless, if the components forming the single molecule are both of human origin, it is preferable for the Sushi domain of the IL15 receptor alpha chain or functionally equivalent variant thereof to also be of human origin. Alternatively, if the components forming the single molecule are both of murine origin, it is preferred for the Sushi domain of the IL15 receptor alpha chain or functionally equivalent variant thereof to also be of murine origin.

In another aspect, the invention contemplates a fusion protein comprising ApoA or a functionally equivalent variant thereof and IL15 or a functionally equivalent variant thereof. The terms "ApoA", "IL15", "functionally equivalent variant of ApoA", "functionally equivalent variant of IL15" have been explained in detail above and are used essentially in the same way as in the case of the fusion proteins.

The fusion proteins may present the polypeptide ApoA in the N-terminal position in relation to IL-15 or the polypeptide IL-15 in the N-terminal position in relation to Apo A. Similarly, both components may be joined directly or through a linker, which may be any of the linkers mentioned in the present invention. Also, the components may be of human or murine origin, in such a way that the invention contemplates fusions of human origin ApoA and IL15, fusions of murine origin ApoA and IL15 and fusions of ApoA and IL15 wherein ApoA is of human origin and IL15 is of murine origin and fusions of ApoA and IL15 wherein ApoA is of murine origin and IL15 is of human origin.

In preferred embodiments of the invention, the fusion proteins of Apo A and IL15 correspond to the polypeptides having sequences SEQ ID NO:39, SEQ ID NO:40 and SEQ ID NO:41.

Fusion Protein of the Invention

In another aspect, the invention relates to a fusion protein comprising
(i) a region A formed by an Apo A polypeptide or a functionally equivalent variant thereof having at least 70% identity to said Apo A polypeptide,
(ii) a region B formed by IL15 or a functionally equivalent variant thereof having at least 70% identity to IL15 and
(iii) a region C formed by the Sushi domain of the IL15 receptor alpha chain or a functionally equivalent variant thereof having at least 70% identity to the Sushi domain of the IL15 receptor alpha chain.

Region A of the fusion protein essentially coincides with the first component of the compositions of the invention meaning that it has been described in detail above.

Region B of the fusion protein essentially coincides with the second component of the compositions of the invention meaning that it has been described in detail above.

Region C of the fusion protein essentially coincides with the third component of the compositions of the invention meaning that it has been described in detail above.

The expert in the art will appreciate that the fusion protein of the invention may present different arrangements of regions A, B and C. Thus, the invention contemplates:
a fusion protein wherein region A is in the N-terminal position, region B is in the central position and region C is in the C-terminal position,
a fusion protein wherein region A is in the N-terminal position, region C in the central position and region B in the C-terminal position,
a fusion protein wherein region B is in the N-terminal position, region A is in the central position and region C is in the C-terminal position,
a fusion protein wherein region B is in the N-terminal position, region C is in the central position and region A is in the C-terminal position,
a fusion protein wherein region C is in the N-terminal position, region A is in the central position and region B is in the C-terminal position and
a fusion protein wherein region C is in the N-terminal position, region B is in the central position and region A is in the C-terminal position.

Also, regions A, B and/or C can be directly associated, in other words, wherein the C-terminal amino acid of a region is joined by a peptide bond to the N-terminal amino acid of another region. Alternatively, the different regions are joined together by a peptide linker. Suitable linkers for the fusion protein of the invention are essentially the same as used in the composition of the invention and have been described in detail above. The expert in the art will appreciate that the fusion protein may contain one or two peptide linkers depending on whether only two of the three regions are associated together by a linker or whether the three regions are associated by linkers.

In a preferred embodiment, the fusion protein presents a C-B-A-type arrangement, in other words, comprises, in the direction N-to C terminal, the Sushi domain of IL15Rα (region C), IL15 (region B) and ApoAI (region A). In an even more preferred embodiment, regions C and B are separated by a linker of type GGSGGGGSGGGSGGGGSLQ (SEQ ID NO:32). In another embodiment, regions B and A are separated by a GAP-type linker. In an even more preferred embodiment, regions C and B are separated by a linker of type GGSGGGGSGGGSGGGGSLQ (SEQ ID NO:32) and regions B and A are separated by a GAP-type linker.

Although the fusion proteins of the invention are exemplified with fusion proteins wherein regions A, B and C are of murine origin, the expert in the art will appreciate that the invention contemplates fusion proteins wherein each one of the regions A, B and C may be of different origin, from among the different variants of the regions mentioned above.

Thus, in a preferred embodiment, the fusion protein comprises a region A of human origin or murine origin, a region B of human origin or murine origin, a region C of human origin or murine origin. In an even more preferred embodiment, the three regions come from the same organism. Thus, in an even more preferred embodiment, regions A, B and C are of murine origin. In another preferred embodiment, regions A, B and C are of human origin.

In a preferred embodiment, the fusion protein presents an arrangement of the C-B-A type wherein the three components are of human origin and wherein both regions C and B as well as regions B and A are connected by peptide linkers. In a preferred embodiment, the fusion protein comprises, in the direction N-to C- terminal, the sushi domain of human IL15Rα (region C), human IL15 (region B) and human ApoAI (region A). In an even more preferred embodiment, regions C and B are separated by a linker of type GGSGGGGSGGGSGGGGSLQ (SEQ ID NO:32). In another embodiment, regions B and A are separated by a GAP-type linker. In an even more preferred embodiment, regions C and B are separated by a linker of type GGSGGGGSGGGSGGGGSLQ (SEQ ID NO:32) and regions B and A are separated by a GAP-type linker. In a preferred embodiment, the fusion protein comprises the sequence defined by SEQ ID NO:42.

In another preferred embodiment, the fusion protein comprises, in the direction N-to C terminal, the sushi domain of murine IL15Rα (region C), murine IL15 (region B) and murine ApoAI (region A). In an even more preferred embodiment, regions C and B are separated by a linker of type GGSGGGGSGGGSGGGGSLQ (SEQ ID NO:32). In another embodiment, regions B and A are separated by a GAP-type linker. In an even more preferred embodiment, regions C and B are separated by a linker of type GGSGGGGSGGGSGGGGSLQ (SEQ ID NO:32) and regions B and A are separated by a GAP-type linker. In a preferred embodiment, the fusion protein comprises the sequence defined by SEQ ID NO:43.

Polynucleotides, Gene Constructs, Vectors and Host Cells of the Invention

In another aspect, the invention contemplates a polynucleotide encoding the fusion protein of the invention. Given that the fusion protein of the invention performs its function from the extracellular medium, it is convenient for the polynucleotide to encode the fusion protein of the invention with a signal sequence that allows the fusion protein access to the secretory pathway and the fusion protein's secretion into the medium. Suitable signal sequences for use together with the fusion protein include both the signal sequence of any of the fusion protein components (the signal sequence of Apo A, signal sequence of IL15 or signal sequence of the IL15 receptor a chain) or any signal sequences mentioned above in the context of the first component of the composition of the invention, in other words, suitable signal sequences of tissue plasminogen activator (tPA), of the growth hormone, of GM-CSF and of immunoglobulins, and, in particular the signal sequences of Igκ or of IgVχ.

In a preferred embodiment, the polynucleotide of the invention comprises the sequence identified as SEQ ID NO:44 encoding a fusion protein or conjugate comprising the human origin Sushi domain, human origin IL15 and human origin ApoA1, wherein the Sushi domain and IL15 are separated by a linker of sequence GGSGGGGSGGGSGGGGSLQ (SEQ ID NO:32), wherein IL15 and ApoA1 are separated by a linker of sequence GAP and wherein the fusion is preceded by the signal sequence of the human origin IL-15 receptor alpha chain.

In a preferred embodiment, the polynucleotide of the invention comprises the sequence identified as SEQ ID NO:45 encoding a fusion protein or conjugate comprising murine origin Sushi domain, murine origin IL15 and murine origin ApoA1, wherein the Sushi domain and IL15 are separated by a linker of sequence GGSGGGGSGGGSGGGGSLQ (SEQ ID NO:32), wherein IL15 and ApoA1 are separated by a linker of sequence GAP and wherein the fusion is preceded by the signal sequence of the murine origin IL-15 receptor alpha chain.

The polynucleotide that encodes the fusion protein of the invention can be operatively associated to a regulatory region of expression thereby giving rise to a gene construct. Therefore, in another aspect, the invention relates to a gene construct comprising a polynucleotide of the invention. Preferably, the construct comprises the polynucleotide of the invention placed under the operational control of sequences that regulate the expression of the polynucleotide of the invention. The expert in the art will appreciate that the polynucleotides of the invention must access the nucleus of a target tissue and therein be transcribed and translated to give rise to the biologically active fusion protein.

In principle, any promoter can be used for the gene constructs of the present invention on condition that said promoter is compatible with the cells in which the polynucleotide is to be expressed. Thus, suitable promoters for carrying out the present invention include, without necessarily limitation, constitutive promoters such as those derived from the genomes of eukaryote viruses such as the polyomavirus, adenovirus, SV40, CMV, bird sarcoma virus, hepatitis B virus, the metallothionein gene promoter, the thymidine kinase gene promoter of the herpes simplex virus, LTR regions of retroviruses, the immunoglobulin gene promoter, the actin gene promoter, the EF-1alpha gene promoter as well as inducible promoters wherein the expression of the protein depends on the addition of a molecule or exogenous signal, such as the tetracycline system, the NFκB/UV light system, the Cre/Lox system and the heat shock gene promoter, regulable promoters of RNA polymerase II described in WO/2006/135436 as well as specific tissue promoters.

The polynucleotides of the invention or gene constructs comprising them may form part of a vector. Thus, in another aspect, the invention relates to a vector which comprises a polynucleotide or a gene construct of the invention. The expert in the art will appreciate that there is no limitation in terms of the type of vector that can be used since said vector may be a cloning vector suitable for propagation and for obtaining the suitable polynucleotides or gene constructs, or expression vectors in different heterologous organisms suitable for purifying the conjugates. Thus, suitable vectors in accordance with the present invention include expression vectors in prokaryotes such as pUC18, pUC19, Bluescript and its derivatives, mp18, mp19, pBR322, pMB9, ColEI, pCRI, RP4, phages and "shuttle" vectors such as pSA3 and pAT28, expression vectors in yeasts such as 2-micra plasmid-type vectors, integration plasmids, YEP vectors, centromeric plasmids and similar, expression vectors in insect cells such as the pAC-series and pVL-series vectors, expression vectors in plants such as vectors of series pIBI, pEarleyGate, pAVA, pCAMBIA, pGSA, pGWB, pMDC, pMY, pORE and similar and expression vectors in superior eukaryotic cells well based in viral vectors (adenovirus, viruses associated to adenovirus as well as retrovirus and lentivirus) in addition to non-viral vectors such as pSilencer 4.1-CMV (Ambion), pcDNA3, pcDNA3.1/hyg pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and pKSV-10, pBPV-1, pML2d and pTDTI.

The vector of the invention can be used to transform, transfect or infect cells prone to transformation, transfection or infection by said vector. Said cells can be prokaryotic or eukaryotic. By way of an example, the vector wherein said DNA sequence is introduced may be a plasmid or a vector that, when introduced in a host cell, integrates in said cell's genome and replicates together with the chromosome (or chromosomes) into which it has been integrated. Said vector may be obtained by conventional methods known to technicians in the art (Sambrook et al., 2001, quoted supra).

Therefore, in another aspect, the invention relates to a cell comprising a polynucleotide, a gene construct or a vector of the invention, wherefore it has been possible to transform, transfect or infect said cell with a construct or vector provided by this invention. Transformed, transfected or infected cells can be obtained by conventional methods known to experts in the art (Sambrook et al., 2001, quoted supra). In a particular embodiment, said host cell is an animal cell transfected or infected with an appropriate vector.

Suitable host cells for the expression of the conjugates of the invention include, without limitation, the cells of mammals, plants, insects, fungi and bacteria. Bacterial cells include, without limitation, the cells of Gram-positive bacteria such as species of the genus *Bacillus, Streptomyces* and *Staphylococcus* and cells of Gram-negative bacteria such as cells of the genus *Escherichia* and *Pseudomonas*. Fungal cells include, preferably, yeast cells such as *Saccharomyces, Pichia pastoris* and *Hansenula polymorpha*. Insect cells include, without limitation, cells of Drosophila and Sf9 cells. Plant cells include, among others, cells from crop plants such as cereals, medicinal or ornamental plants or bulbs. Suitable mammal cells for the present invention include epithelial cell lines (porcine, etc.), osteosarcoma cell lines (human, etc.), neuroblastoma cell lines (human, etc.), epithelial carcinomas (human, etc.), glial cells (murine, etc.), liver cell lines (monkey, etc.). CHO cells (Chinese Hamster Ovary), COS cells, BHK cells, cells HeLa, 911, AT1080, A549, 293 or PER.C6, human ECCs NTERA-2 cells, D3 cells of the line of mESCs, human embryonic stem cells such as HS293 and BGV01, SHEF1, SHEF2 and HS181, cells NIH3T3, 293T, REH and MCF-7 and hMSCs cells.

In Vitro Methods of the Invention

The capacity of IL15 to promote the proliferation of antigen-sensitised T lymphocytes has been described. Thus, it has been demonstrated that contacting a population of isolated lymphocytes previously exposed to a determined antigen with IL15 results in an increase in lymphocyte proliferation. This expanded lymphocyte population can be used in adoptive immunotherapy whereby it is subsequently re-administered to the patient from which said initial population has been obtained. Therefore, in another aspect, the invention relates to an in vitro method for promoting the expansion of antigen-specific T lymphocytes comprising contacting a population of lymphocytes previously exposed to said antigen with a composition of the invention, a fusion protein of the invention, a polynucleotide of the invention, a vector of the invention, a gene construct of the invention or a host cell of the invention.

The term "expansion" is used in the present invention indiscriminately with proliferation and must be understood as cell division or cell growth. The expansion may be determined using extensively known methods, such as, for example, the methods described in Transplantation (1999) 67: 605-613.

The expression "antigen-specific T lymphocytes", as used in the present invention, refers to a lymphocyte population capable of recognising a specific antigen. Typically, lymphocytes are isolated from a patient who has been exposed to said antigen. Alternatively, the antigen may be placed in contact with the lymphocyte population in an artificial antigen-presenting system as described in US patents U.S. Pat. Nos. 6,828,150 or 6,787,154.

The term "antigen", as used in the present invention, refers to any substance capable of triggering an immune response in a subject who is intolerant to said antigen. The antigen may come from the subject himself, in which case it is an autoantigen, or may be an alloantigen, in other words, an antigen derived from an individual of the same species. Alternatively, the antigen may be a xenoantigen, in other words, an antigen derived from an individual of a different species.

The lymphocytes that can be used in the method of the present invention include, without limitation, cytotoxic T lymphocytes (CTL), T helper cells, lymphokine-activated cells, tumour-infiltrating lymphocytes (TILS), NK cells, naive cells, memory cells, gamma delta T cells, NKT cells as well as cell populations comprising variable quantities of one or more of the aforesaid cells. In a preferred embodiment, the lymphocytes are CTL. Suitable methods for obtaining CTLs for subsequent expansion in vitro using the method of the invention are extensively known to an expert in the art and include, without limitation, isolation from peripheral blood, from umbilical cord blood, from tissues containing lymphocytes. In a preferred embodiment, the lymphocytes are isolated through drainage from the lymph nodes of patients suffering from a particular disease.

Once the lymphocytes have been isolated, they are placed in contact with a composition of the invention, a fusion protein of the invention, a polynucleotide of the invention, a vector of the invention, a gene construct of the invention or a host cell of the invention in suitable conditions for lymphocyte expansion to take place. The general conditions for antigen-specific CTL expansion can be established according to well-known methods [for example, Carter J. et al., Immunology, 57 (1), 123-129, (1996)] and may be routinely optimised by an expert in the art. Typically, contacting the lymphocytes with the composition, fusion protein, polynucleotide, vector, gene construct or host cell of the invention is carried out by means of culturing the lymphocytes in a suitable medium for said cells. The cells may be cultured under conventional conditions in a suitable medium for growing lymphocytes which include a Minimum Essential Medium or RPMI 1640 Medium. With a view to promoting cell growth, necessary proliferation and viability factors may be added including serum, for example, foetal calf serum or human serum and antibiotics, for example, penicillin, streptomycin. The lymphocytes are kept in the necessary conditions for supporting growth, for example, at a suitable temperature of about 37° C. and atmosphere, for example, air plus 5% $CO_2$.

In a preferred embodiment, the lymphocytes can be treated prior to their stimulation using the compounds of the invention to promote their activation in vitro, by contacting the lymphocytes with the antigen against which they are specific. This is particularly necessary in the case of patients with tumours producing immunosuppressant substances. To achieve this, it is necessary to stimulate the lymphocyte's culture with the appropriate antigen. Typically, the antigen is presented to the T cell in such a way that the signal is triggered in the T cell through the TCR/CD3 complex. Preferably, the antigen can be presented to the T cell by means of an antigen-presenting cell.

The expression "antigen-presenting cell", as used in the present invention, refers to a cell that contributes to generating the immune response by means of presenting an antigen to the T lymphocytes. Antigen-presenting cells include dendritic cells, mononuclear phagocytes, B lymphocytes or Langerhans cells. Antigen-presenting cells may be isolated, for example, from the bone marrow, blood, thymus, epidermis, liver or foetal liver.

In the case of the antigen being a tumoral antigen, it is possible to use an extract of the autologous tumour and/or a recombinant tumour antigen. In the case of an antigen from a pathogen, the lymphocyte activation prior to expansion can be carried out using a pathogen-infected cell, for example a virus presenting antigens of the pathogen.

In the method for the antigen-specific CTL expansion of the present invention, it is preferable for the treatment of the cells with the compositions, fusion proteins of the invention to be carried out in the presence of an anti-CD3 antibody and, preferably, with a human monoclonal anti-CD3 antibody, and more preferably with OKT3. The concentration of anti-CD3 antibodies during the expansion process is not especially limited and is, for example, 0.001 to 100 mg/mL, and more preferably 0.01 to 100 mg/mL. Additionally or alternatively, the cells may be co-cultured with an anti-CD28 antibody, and more preferably with a human monoclonal anti-CD28 antibody. Additionally or alternatively, the cells can be co-cultured with a lymphocyte-stimulating factor, such as a lectin. Also, one or more of these components can be immobilised to a solid phase.

Also, in the method for the expansion of antigen-specific CTLs of the present invention, the cells can be co-cultured with feeder cells according to the circumstances. In principle, there is no limitation in terms of the type of feeder cells that can be used on condition that said feeder cells cooperate with the protein or composition of the invention or with the agents mentioned in the previous paragraph in the capacity to promote CTL-proliferation. Preferably, suitable feeder cells include, without limitation peripheral blood mononuclear cells (PBMCs) and autologous or non-autologous EBV-B cells. Normally, the feeder cells are treated once used to eliminate their proliferation capacity, preferably through treatment with X-rays or cytotoxic agents such as mitomycin.

The cytotoxic activity of the lymphocyte population obtained following the method of the invention can be determined using well-known methods. For example, it is possible to determine the lymphocytes' capacity to provoke a marked target cell's lysis and to determine the release of the marked substance. Alternatively, the cytotoxic activity can be determined by identifying the level of cytokine (for example, GM-CSF and IFN-γ) produced by the lymphocytes or the target cell. Alternatively, the cytotoxic activity can be determined by contacting the lymphocytes with a specific antibody of cytotoxic lymphocytes marked with a first fluorescent molecule and a complex formed by the antigenic peptide and the major complex of histocompatibility marked with a second fluorescent molecule followed by the detection of cells marked with both molecules by means of flow cytometry.

The lymphocyte populations expanded according to the methods of the present invention are particularly useful for use in adoptive immunotherapy, in other words, for re-administering to subjects requiring a higher immune response against a specific antigen. Preferably, T lymphocytes are used autologously, in other words, are re-administered to the subject from whom they were originally extracted.

Pharmaceutical Compositions of the Invention

The compositions, polynucleotides and fusion proteins of the invention are useful for treating diseases requiring a prolonged dose of IL15. Therefore, in another aspect, the invention relates to a pharmaceutical preparation comprising a therapeutically effective amount of a composition, a fusion protein, a polynucleotide, a gene construct, a vector or a host cell according to the invention and a pharmaceutically acceptable excipient or vehicle.

Preferred excipients for use in the present invention include sugars, starches, celluloses, gums and proteins. In a preferred embodiment, the pharmaceutical composition of the invention is formulated in a pharmaceutical form for administration as a solid (for example tablets, capsules, lozenges, granules, suppositories, crystalline or amorphous sterile solids that can be reconstituted to provide liquid forms, etc.), liquid (for example solutions, suspensions, emulsions, elixirs, lotions, unguents, etc.) or semi-solid (gels, ointments, creams and similar). The pharmaceutical compositions of the invention can be administered by any route, including, without limitation, oral, intravenous, intramuscular, intraarterial, intramedullary, intratecal, intraventricular, transdermic, subcutaneous, intraperitoneal, intranasal, enteric, topical, sublingual or rectal route. A revision of the different forms of administration of active principles, the excipients to be used and their manufacturing procedures can be found in the Tratado de Farmacia Galénica, C. Fauli i Trillo, Luzán 5, S.A. de Ediciones, 1993 and in Remington's Pharmaceutical Sciences (A. R. Gennaro, Ed.), $20^{th}$ edition, Williams & Wilkins PA, USA (2000) Examples of pharmaceutically acceptable vehicles are known in the state of the technique and include saline solutions buffered with phosphate, water, emulsions, such as oil/water emulsions, different types of humidifying agents, sterile solutions, etc. The compositions comprising said vehicles can be formulated by conventional procedures known in the state of the technique.

Alternatively, the compositions and compounds of the invention can be formulated as nanolipoparticles in those cases where the composition comprises an ApoA protein or a fusion of ApoA and a second component (IL15 or Sushi domain of the IL15 receptor alpha chain) or in those cases where the invention contemplates a fusion protein comprising Apo A, IL15 and the sushi domain of IL15RA). The formation of the nanolipoparticle is based on ApoA being the major component of high density lipoproteins (HDL).

In the context of the present invention, the term "nanolipoparticle" is equivalent to the terms "lipoprotein" or "lipoprotein particle" which can be used indiscriminately. Nanolipoparticle is understood to mean any water-soluble particle, formed by a nucleus of apolar lipids (such as esterified cholesterol and triglycerides) covered with an external polar layer formed by apoproteins, phospholipids and free cholesterol.

The nanolipoparticles or lipoproteins are classified according to their density into chylomicrons, very low density lipoproteins (VLDs), intermediate density lipoproteins (IDLs), low density lipoproteins (LDLs) and high density lipoproteins (HDLs). The different characteristics of the lipoproteins are shown in Table 1.

TABLE 1

| Density (g/mL) | Class | Diameter (nm) | % protein | % cholesterol | % phospholipid | % triacylglycerol |
| --- | --- | --- | --- | --- | --- | --- |
| >1.063 | HDL | 5-15 | 33 | 30 | 29 | 8 |
| 1.019-1.063 | LDL | 18-28 | 25 | 50 | 21 | 4 |
| 1.006-1.019 | IDL | 25-50 | 18 | 29 | 22 | 31 |
| 0.95-1.006 | VLDL | 30-80 | 10 | 22 | 18 | 50 |
| <0.95 | chylomicrons | 100-1000 | <2 | 8 | 7 | 84 |

In a more particular embodiment, the nanolipoparticle is an HDL-type lipoprotein characterised in that it presents a composition as indicated in the table above and in that the apolipoproteins that form the protein fraction are Apo A, Apo C, Apo D and Apo E.

Nanolipoparticles can be obtained by conventional methods known to technicians in the art. By way of illustration, the nanolipoparticles can be obtained in vitro through adding cholesterol and phosphatidylcholine to the fusion protein as described in Lerch et al. (Vox Sang, 1996, 71: 155-164) or in vivo by using a non-human animal that expresses the conjugate of the invention in the liver giving rise to the formation of nanolipoparticles that are secreted into serum, from where they can be isolated.

In the case of the pharmaceutical composition of the invention comprising nucleic acids (the polynucleotides of the invention, vectors or gene constructs), the invention contemplates specially prepared pharmaceutical compositions for administering said nucleic acids. The pharmaceutical compositions can comprise said nucleic acids in naked form, in other words, in the absence of compounds protecting the nucleic acids from degradation by the organism's nucleases, which entails the advantage of eliminating the toxicity associated to the reagents used for transfection. Suitable routes of administration for the naked compounds include intravascular, intratumoral, intracraneal, intraperitoneal, intrasplenic, intramuscular, subretinal, subcutaneous, mucous, topical and oral route (Templeton, 2002, DNA Cell Biol., 21:857-867). Alternatively, the nucleic acids can be administered forming part of liposomes, conjugated to cholesterol or conjugated to compounds capable of promoting translocation through cell membranes such as the Tat peptide derived from the TAT protein of HIV-1, the third helix of the homeodomain of the Antennapedia protein of D.melanogaster, the VP22 protein of the herpes simplex virus, oligomers of arginine and peptides such as those described in WO07069090 (Lindgren, A. et al., 2000, Trends Pharmacol. Sci, 21:99-103, Schwarze, S. R. et al., 2000, Trends Pharmacol. Sci., 21:45-48, Lundberg, M et al., 2003, Mol. Therapy 8:143-150 and Snyder, E. L. and Dowdy, S. F., 2004, Pharm. Res. 21:389-393). Alternatively, the polynucleotide can be administered forming part of a plasmidic vector or of a viral vector, preferably vectors based on an adenovirus, in adeno-associated viruses or in retroviruses, such as viruses based on the virus of murine leukaemia (MLV) or on lentiviruses (HIV, FIV, EIAV).

In another embodiment, the compositions, fusion proteins and polynucleotides of the invention are administered by so-called "hydrodynamic administration" as described by Liu, F., et al., (Gene Ther, 1999, 6:1258-66). According to the aforesaid method, the compounds are introduced into the organism intravascularly at high speed and volume, resulting in high levels of transfection with a more widespread distribution. It has been demonstrated that the efficacy of intracellular access depends directly on the volume of fluid administered and on the speed of the injection (Liu et al., 1999, Science, 305:1437-1441). In mice, the administration has been optimised to values of 1 ml/10 g of body weight over a period of 3-5 seconds (Hodges et al., 2003, Exp. Opin. Biol. Ther, 3:91-918). The exact mechanism that allows cellular transfection in vivo with polynucleotides following their hydrodynamic administration is not entirely known. In the case of mice, it is believed that administration by the tail vein occurs at a higher rhythm than the heart beat, provoking the administered fluid to accumulate in the superior vena cava. This fluid subsequently accesses the organ's vessels and, subsequently, through fenestration in the aforesaid vessels, accesses the extravascular space. In this way, the polynucleotide comes into contact with the cells of the target organ before mixing with the blood thereby reducing the possibilities of degradation by nucleases.

The compositions of the invention can be administered at doses of less than 10 mg per kilogram of body weight, preferably less than 5, 2, 1, 0.5, 0.1, 0.05, 0.01, 0.005, 0.001, 0.0005, 0.0001, 0.00005 or 0.00001 mg per each kg of body weight and less than 200 nmol of agent, in other words, approximately $4.4 \times 10^{16}$ copies per kg of body weight or less than 1500, 750, 300, 150, 75, 15, 7.5, 1.5, 0.75, 0.15 or 0.075 nmol per Kg of body weight. The unitary dose can be administered by injection, by inhalation or by topical administration. The bifunctional polynucleotides and compositions of the invention can be administered directly into the organ in which the target mRNA is expressed in which case doses will be administered of between 0.00001 mg and 3 mg per organ, or preferably between 0.0001 and 0.001 mg per organ, about 0.03 and 3.0 mg per organ, about 0.1 and 3.0 mg per organ or between 0.3 and 3.0 mg per organ.

The dose will depend on the severity and response to the condition to be treated and may vary between several days and several months or until the condition is seen to remit. The optimum dose can be determined by periodically measuring the agent's concentrations in the patient's organism. The optimum dose can be determined from the EC50 values obtained through previous in vitro or in vivo tests in animal models. The unitary dose can be administered once a day or less than once a day, preferably, less than once every 2, 4, 8 or 30 days. Alternatively, it is possible to administer an initial dose followed by one or several maintenance doses, generally in a lesser amount that the initial dose. The maintenance regime may involve treating the patient with doses ranging between 0.01 µand 1.4 mg/kg of body weight per day, for example 1, 0.1, 0.01, 0.001, or 0.00001 mg per kg of body weight per day. Maintenance doses are administered, preferably, at most once every 5, 10 or 30 days. The treatment must continue for a time that will vary according to the type of alteration suffered by the patient, its severity and the patient's condition. Following treatment, the patient's evolution must be monitored in order to determine whether the dose ought to be increased in the case of the disease not responding to the treatment or whether the dose ought to be decreased in the case of observing an improvement in the disease or unwanted secondary effects.

The daily dose can be administered in a single dose or in two or more doses according to the particular circumstances. If a repeated administration or frequent administrations are required, it is advisable to implant an administration device, such as a pump, a semi-permanent catheter (intravenous, intraperitoneal, intracisternal or intracapsular) or a reservoir.

Therapeutic Uses of the Compositions and Fusion Proteins of the Invention

In an additional aspect, the invention relates also to the compositions, fusion proteins and polynucleotides of the invention for use in medicine.

The compositions of the invention are capable of promoting the proliferation of intrasplenic, liver and peripheral blood CD8 lymphocytes in vivo (see example 5 of the invention), presenting an antitumoral effect in different models of colorectal adenocarcinoma (see examples 6 and 7) and demonstrating an anti-metastatic effect (see example 8). These effects in conjunction with evidence of IL15's capacity to promote NK cell activity allow use of the compounds and compositions of the invention to treat patients who can benefit from stimulation of the innate (NK cell-mediated) or adaptive (CD8 lymphocyte-mediated) immune response.

Therefore, in another aspect, the invention relates to a composition of the invention, a fusion protein of the invention, a polynucleotide of the invention, a vector or a gene construct of the invention, or a host cell of the invention for use in stimulating a subject's immune response.

Preferably, the composition of the invention, fusion protein of the invention, polynucleotide of the invention, vector or gene construct of the invention, or host cell of the invention are used to treat a disease that requires activation of the immune system in response to an antigen.

Alternatively, the invention relates to the use of a composition of the invention, a fusion protein of the invention, a polynucleotide of the invention, a vector or a gene construct of the invention, or a host cell of the invention for the manufacture of a medicament for stimulating a subject's immune response to an antigen or to treat a disease requiring activation of the immune system.

Alternatively, the invention relates to a method for promoting the stimulation of a subject's immune response to an antigen or for treating a disease requiring activation of the immune system which comprises the administration to said subject of a composition of the invention, a fusion protein of the invention, a polynucleotide of the invention, a vector or a gene construct of the invention, or a host cell of the invention.

The expression "stimulation of a subject's immune response", as used in the present invention, refers to the initiation of an immune response against a specific antigen in an individual wherein said response occurs for the first time as well as to the reactivation of the immune response in subjects wherein said immune response has already occurred. It is understood that the immune response can involve both the innate as well as the adaptive immune response, and can involve either a humoral or cellular-type response.

Therefore, the capacity of the compounds and compositions of the invention to increase a subject's immune response to a specific antigen can be useful for treating diseases associated to the presence of said antigen in the organism, which includes diseases caused by viral infections if dealing with a viral antigen, diseases caused by bacterial infections if dealing with a bacterial antigen, diseases caused by fungal infections if dealing with a fungal antigen, allergies if dealing with an allergen, diseases caused by a parasitic infestation if dealing with a parasitic antigen and/or a tumour if dealing with a tumour cell specific antigen. Therefore, in preferred embodiments, the disease requiring activation of the immune system is selected from the group of an infectious disease and a neoplastic disease.

Diseases caused by viral infections that can be treated using the compounds and combinations of the invention include, without limitation, diseases caused by infections with the HIV-1 virus (AIDS), by the human herpes virus such as the simple herpes virus (simple herpes, genital herpes), cytomegalovirus (mononucleosis, retinitis, hepatitis), the Epstein Barr virus (infectious mononucleosis, Burkitt's lymphoma and nasopharyngeal carcinoma) and the virus of varicella zoster (chickenpox, herpes zoster); by hepatitis viruses such as hepatitis B virus or hepatitis C virus, by paramyxovirus such as respiratory syncytial virus, the parainfluenza virus, rubella virus, measles virus, mumps virus, human papillomavirus; flavivirus such as the yellow fever virus, dengue fever virus, the virus of tick-transmitted encephalitis or the Japanese encephalitis virus) and rotavirus. Other types of viral infections that can be treated using the compounds and combinations of the present invention are described in detail in Fundamental Virology, second edition, eds. Fields, B. N. and Knipe, D. M. (Raven Press, New York, 1991).

Diseases caused by bacterial infections that can be treated using the compounds and combinations of the invention include, without limitation, diseases caused by microorganisms of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus* or *Bordetella*.

Diseases caused by fungal infections that can be treated using the compounds and combinations of the invention include, without limitation, candidiasis, aspergillosis, histoplasmosis, cryptococcal meningitis and similar.

Parasitic infections that can be treated using the compounds and combinations of the invention include, without limitation, malaria, infection by *Pneumocystis jiroveci*, pneumonia, sleeping sickness, leishmaniosis, cryptosporidiosis, toxoplasmosis and trypanosoma.

Allergic-type disorders that can be treated using the compounds and compositions of the invention include, without limitation, allergies caused by exposure to pollen (allergens of pollen from trees, herbs, weeds, and grasses), allergies caused by exposure to insect allergens (inhalable allergens, allergens from saliva, and poison), dandruff and animal hair allergens and food allergens.

The conjugates and compositions of the invention are also suitable for treating hyperproliferative diseases. The expression "proliferative disease", as used in the present invention, refers to diseases caused by or resulting from inappropriately high levels of cell division, inappropriately low levels of apoptosis or both and include both primary tumours as well as metastases. The term "primary tumour" refers to a tumour in the primary site where the tumour originated. The term "metastasis", as used in the present invention, refers to the process whereby a tumour extends to organism tissues other than those of the tumour's original primary site.

In the context of the invention, "treatment of a hyperproliferative disease" or "treatment of a tumour" is understood to mean the administration of the compounds and compositions of the invention in order to prevent or delay the appearance of symptoms, complications, or biochemical indications of the cancer or tumour, to alleviate its symptoms or to prevent or inhibit its growth and progression such as, for example, the appearance of metastasis. The treatment may be a prophylactic treatment to delay the appearance of the disease or to prevent the manifestation of its clinical or sub-clinical symptoms or a therapeutic treatment to eliminate or alleviate symptoms after manifestation of the disease or in relation to its treatment through surgery or radiotherapy.

The cancer to be treated in the context of the present invention may be any type of cancer or tumour. These tumours or cancer include, and are not limited to, malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genito-urinary apparatus and, more particularly, childhood acute lymphoblastic leukaemia, acute lymphoblastic leukaemia, acute lymphocytic leukaemia, acute myeloid leukaemia, adrenocortical carcinoma, adult (primary) hepatocellular cancer, adult (primary) liver cancer, adult acute lymphocytic leukaemia, adult acute myeloid leukaemia, adult Hodgkin's disease, adult Hodgkin's lymphoma, adult lymphocytic leukaemia, adult non-Hodgkin's lymphoma, adult primary liver cancer, adult soft tissue sarcoma, AIDS-related lymphoma, AIDS-related malignant tumours, anal cancer, astrocytoma, cancer of the biliary tract, cancer of the bladder, bone cancer, brain stem glioma, brain tumours, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukaemia, childhood acute myeloid leukaemia, childhood brain stem glioma, childhood cerebellar astrocytoma, childhood brain astrocytoma, childhood extracranial germ cell tumours, childhood Hodgkin's disease, childhood Hodgkin's lymphoma, childhood visual pathway and hypothalamic glioma, childhood lymphoblastic leukaemia, childhood medulloblastoma, childhood non-Hodgkin's lymphoma, childhood supratentorial primitive neuroectodermal and pineal tumours, childhood primary liver cancer, childhood rhabdomyosarcoma, childhood soft tissue sarcoma, childhood visual pathway and hypothalamic glioma, chronic lymphocytic leukaemia, chronic myeloid leukaemia, cancer of the colon, cutaneous T-cell lymphoma, endocrine pancreatic islet cells carcinoma, endometrial cancer, ependymoma, epithelial cancer, cancer of the oesophagus, Ewing's sarcoma and related tumours, cancer of the exocrine pancreas, extracranial germ cell tumour, extragonadal germ cell tumor, extrahepatic biliary tract cancer, cancer of the eye, breast cancer in women, Gaucher's disease, cancer of the gallbladder, gastric cancer, gastrointestinal carcinoid tumour, gastrointestinal tumours, germ cell tumours, gestational trophoblastic tumour, tricoleukaemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukaemia, myeloid leukaemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous osteosarcoma-Z, osteosarcoma-W, malignant fibrous histiocytoma, malignant fibrous osteosarcoma/histiocytoma of the bone, epithelial ovarian cancer, ovarian germ cell tumour, ovarian low malignant potential tumour, pancreatic cancer, paraproteinemias, purpura, parathyroid cancer, cancer of the penis, phaeochromocytoma, hypophysis tumour, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, Sezary's syndrome, skin cancer, small cell lung cancer, small intestine cancer, soft tissue sarcoma, squamous neck cancer, stomach cancer, pineal and supratentorial primitive neuroectodermal tumours, T-cell lymphoma, testicular cancer, thymoma, thyroid cancer, transitional cell cancer of the renal pelvis and ureter, transitional renal pelvis and ureter cancer, trophoblastic tumours, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumour and any other hyperproliferative disease, as well as neoplasia, located in the system of a previously mentioned organ.

Vaccine Compositions of the Invention

The compounds and compositions of the invention are useful also as adjuvants in vaccines to increase a patient's response to an antigen. Thus, in another aspect, the invention relates to a vaccine composition comprising an antigen and a composition, fusion protein, polynucleotide, gene construct, vector or host cell according to the invention.

The term "vaccine" or "vaccine composition", as used in the present invention, refers to a composition comprising at least one antigen of interest that allows activation of a subject's immune response to said antigen. The purpose of the vaccines is to activate immunity mediated by both cells as well as antibodies. Preferably, cell-mediated immunity includes the stimulation of a T-cell response, mainly, a response mediated by CD4+, and/or a response of CD8+ T cells.

The term "adjuvant", as used in the present invention, refers to an immunological agent capable of activating the immune system allowing a more intense and more efficient immune response to a vaccine than would be obtained as a result of administering the vaccine without the adjuvant. Typical responses to adjuvants include, without limitation, the activation, proliferation and/or differentiation of immune system cells (B cells, T cells, dendritic cells, antigen-presenting cells, macrophages, NK cells), the increase or decreased expression of markers and cytokines, the stimulation of IgA, IgM and/or IgG titres, splenomegalia (increase in spleen cellularity), hyperplasia, the formation of infiltrates in different organs and other types of responses that can be quantified by an expert in the art using standard technology.

Thus, the vaccines that can be used in combination with the combinations and compounds of the invention include vaccines presenting one or more antigens selected from the group of a viral antigen, bacterial antigens, a fungal antigen, an allergen or an environmental antigen and a tumoral antigen.

Viral antigens suitable for use in the vaccines that can be used with the compounds and combinations of the invention include HIV-1 antigens (such as tat, nef, gp120 or gp160, gp40, p24, gag, env, vif, vpr, vpu, rev), human herpes viruses, (such as gH, gL gM gB gC gK gE or gD or derivatives thereof) or immediate early protein such as ICP27, ICP47, ICP4, ICP36 of VHS1 or VHS2, cytomegalovirus, especially human, (such as gB or derivatives thereof), Epstein Barr viruses (such as gp350 or derivatives thereof), viruses of varicella zoster (such as gpI, II, III and IE63), or a virus of hepatitis such as the hepatitis B virus (for example surface antigen of hepatitis B or nucleus antigen of hepatitis), hepatitis C virus (for example nucleus antigens, E1, NS3 or NS5), of paramyxovirus such as respiratory syncytial virus (such as proteins F and G or derivatives thereof), of the parainfluenza virus, of the measles virus (such as proteins EI and E2), chickenpox virus, mumps virus, human papillomavirus (for example HPV6, 11, 16, 18, eg LI, L2, EI, E2, E3, E4, E5, E6, E7), flavivirus (for example the virus of yellow fever, dengue fever virus, virus of tick-transmitted encephalitis, Japanese encephalitis virus) or cells infected with influenza viruses, such as proteins HA, NP, NA or M, or combinations thereof), antigens of rotavirus (such as VP7sc and other rotavirus components), and similar (see Fundamental Virology, second edition, eds. Fields, B. N. and Knipe, D. M. (Raven Press, New York, 1991) for additional examples of viral antigens.

Bacterial antigens or derivatives suitable for use in the vaccines that can be used with the compounds and combinations of the invention include antigens of *Neisseria* spp, including *N. gonorrhea* and *N. meningitidis* (transferrin binding proteins, lactoferrin binding proteins, PiIC and adhesins); antigens of *S. pyogenes* (such as M proteins or fragments thereof and C5A protease); antigens of *S. agalactiae, S. mutans; H. ducreyi; Moraxella* spp, including *M catarrhalis*, also known as *Branhamella catarrhalis* (such as low and high molecular weight adhesins and invasins); antigens of *Bordetella* spp, including *B. pertussis* (for example *Parapertussis* and *B. bronchiseptica* (such as pertactin, the whooping cough toxin or derivatives thereof, filamentous hemagglutinin, adenylate cyclase, fimbriae); antigens of *Mycobacterium* spp., including *M. tuberculosis, M. bovis, M. leprae, M. avium, M. paratuberculosis, M. smegmatis; Legionella* spp, including *L. pneumophila*; (for example ESAT6, antigen 85A, -B or -C, MPT 44, MPT59, MPT45, HSPIO, HSP65, HSP70, HSP 75, HSP90, PPD of 19kDa [Rv3763], PPD of 38kDa [Rv0934]); antigens of *Escherichia* spp, including enterotoxigenic *E. coli* (for example colonisation factors, thermolabile toxin or derivatives thereof, thermostable toxin or derivatives thereof), antigens of enterohaemorrhagic *E. coli* and enteropathogenic *E. coli* (for example toxin similar to the Shiga-toxin or derivatives thereof); antigens of *Vibrio* spp, including *V. cholera* (for example cholera toxin or derivatives thereof); antigens of *Shigella* spp, including *S. sonnei, S. dysenteriae, S. flexnerii; Yersinia* spp, including *Y. enterocolitica* (for example a Yop protein); antigens of *Y. pestis, Y. pseudotuberculosis; Campylobacter* spp, including *C. jejuni* (for example toxins, adhesins and invasins); antigens of *Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); antigens of *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanic toxin and derivative thereof); antigens of *C. botulinum* (for example botulinic toxin and derivative thereof), antigens of *C. difficile* (for example toxins of clostridium A or B and derivatives thereof); antigens of *Bacillus* spp., including *B. anthracis* (for example the anthrax toxin and derivatives thereof); *Corynebacterium* spp., including *C. diphtheriae* (for example diphtheria toxin and derivatives thereof); antigens of *Borrelia* spp., including *B. burgdorferi* (for example OspA, OspC, DbpA, DbpB); antigens of *B. garinii* (for example OspA, OspC, DbpA, DbpB), *B. afzelii* (for example OspA, OspC, DbpA, DbpB), antigens of *B. andersonfi* (for example OspA, OspC, DbpA, DbpB), antigens of *B. hermsii; Ehrlichia* spp., including *E. equi* and the agent of human granulocytic ehrlichiosis; *Rickettsia* spp, including *R. rickettsii; Chlamydia* spp., including *C. trachomatis* (for example MOMP, heparin-binding proteins); antigens of *Chlamydia pneumoniae* (for example MOMP, heparin-binding proteins), antigens of *C. psittaci; Leptospira* spp., including *L. interrogans; Treponema* spp., including *T. pallidum* (for example rare outer membrane proteins), antigens of *T. denticola, T. hyodysenteriae*; antigens of *Plasmodium* spp., including *P. falciparum; Toxoplasma* spp. and *T. gondii* (for example SAG2, SAGS, Tg34); antigens of *Entamoeba* spp., including *E. histolytica; Babesia* spp., including *B. microti; Trypanosoma* spp., including *T. cruzi; Giardia* spp., including *G. lamblia; leishmania* spp., including *L. major; Pneumocystis* spp., including *P. carinii; Trichomonas* spp., including *T. vaginalis; Schisostoma* spp., including *S. Mansoni*.

Antigens of or derived from yeast such as *Candida* spp., including *C. albicans; Cryptococcus* spp., including *C. neoformans*; antigens of *M. tuberculosis* (such as Rv2557, Rv2558, RPFs: Rv0837c, Rv1884c, Rv2389c, Rv2450, Rv1009, aceA (Rv0467), PstS1, (Rv0932), SodA (Rv3846), Rv2031c of 16 kDal, Tb Ra12, Tb H9, Tb Ra35, Tb38-1, Erd 14, DPV, MTI, MSL, mTTC2 and hTCC1); antigens of *Chlamydia*, such as high molecular weight protein (HMWP), ORF3 (document EP 366 412) and possible membrane proteins (Pmp); antigens of *Streptococcus* spp, including *S. pneumoniae* (PsaA, PspA, streptolysin, choline binding proteins, the protein antigen pneumolysin, and mutant detoxified derivatives thereof); antigens derived from *Haemophilus* spp., including *H. influenzae* type B (for example PRP and conjugates thereof); antigens of unclassifiable *H. influenzae* (such as OMP26, high molecular weight adhesins, P5, P6, protein D and lipoprotein D, and fimbrin and fimbrin derived peptides, or variants of multiple copies or the fusion proteins thereof); antigens derived from *Plasmodium falciparum* (such as RTS.S, TRAP, MSP1, AMA1, MSP3, EBA, GLURP, RAP1, RAP2, sequestrin, PfEMP1, Pf332, LSA1, LSA3, STARP, SALSA, PfEXP1, Pfs25, Pfs28, PFS27/25, Pfs16, Pfs48/45, Pfs230 and analogues thereof in *Plasmodium* spp.)

Fungal antigens suitable for use in the vaccines that can be used with the compounds and combinations of the invention include, without limitation, for example, components of the fungal antigen of *Candida*; fungal antigens of *Histoplasma* such as heat shock protein 60 (HSP60) and other components of fungal antigens of *Histoplasma*; fungal antigens of cryptococcus such as capsular polysaccharides and other components of fungal antigens of cryptococcus; fungal antigens of coccidia such as antigens of spherula and other components of fungal antigens of coccidia; and fungal antigens of *Tinea* such as trichophytin and other components of fungal antigens of coccidia.

Protozoan antigens suitable for use in the vaccines that can be used with the compounds and combinations of the invention include, without limitation, antigens of *Plasmodium falciparum* such as merozoite surface antigens, sporozoite surface antigens, circumsporozoite antigens, gametocyte/gamete surface antigens, whole blood antigen pf, 55/RESA and other components of plasmoid antigens; antigens of *Toxoplasma* such as SAG-I, p30 and other components of *Toxoplasma* antigens; antigens of schistosoma such as glutation-S-transferase, paramyosin and other components of the schistosoma antigen; the antigen of *Leishmania* and other antigens of *Leishmania* tales such as gp63, lipophosphoglycan and its associated protein and other components of the

*Leishmania* antigen; and antigens of *Trypanosoma cruzi* such as the antigen of 75-77 kDa, the antigen of 56 kDa and other components of the *Trypanosoma* antigen.

Allergens or environmental antigens suitable for use in the vaccines that can be used with the compounds and combinations of the invention include, without limitation, antigens derived from naturally-produced allergens such as pollen allergens (allergens of the pollen from trees, herbs, weeds and grasses), insect allergens (inhalable allergens, from saliva and poison), dandruff and animal hair allergens, and food allergens. Important pollen allergens from trees, grasses and herbs originate from taxonomic orders of *Fagales, Oleales, Pinales* and *Platanaceae* including among others birch (*Betula*), alder (*Alnus*), hazel nut tree (*Corylus*), hornbeam (*Carpinus*) and olive (*Olea*), cedar (*Cryptomeria* and *Juniperus*), banana tree (*Platanus*), the order of Poales including among others grasses of the genera *Lolium, Phleum, Poa, Cynodon, Dactylis, Holcus, Phalaris, Secale and Sorghum*, the orders of Asterales and Urticales including among others herbs of the genera *Ambrosia, Artemisia* and *Parietaria*. Other allergenic antigens that can be used include the allergens of household dust mites of the genera *Dermatophagoides* and *Euroglyphus*, storage mites for example *Lepidoglyphys, Glycyphagus* and *Tyrophagus*, those of cockroaches, midges and fleas for example *Blatella, Periplaneta, Chironomus* and *Ctenocephalides*, those of mammals such as cat, dog and horse, birds, poison allergens including those originating from insect stings or bites such as those of the taxonomic order of Hymenoptera including bees (superfamily Apidae), wasps and ants (superfamily Formicoidae). Yet more allergenic antigens that can be used include inhaled fungal allergens such as from the genera *Alternaria* and *Cladosporium*.

Tumoral antigens suitable for use in the vaccines that can be used with the compounds and combinations of the invention include, without limitation, MAGE, MART-1/Melan-A, gp100, dipeptidyl peptidase IV (DPPIV), adenosine deaminase binding protein (ADAbp), cyclophilin b, colorectal associated antigen (CRC)-0017-1A/GA733, carcinoembrionary antigen (CEA) and its antigenic epitopes CAP-1 and CAP-2, etv6, aml1, prostate specific antigen (PSA) and its antigenic epitopes PSA-1, PSA-2, and PSA-3, prostate specific membrane antigen (PSMA), T-cell/CD3-c chain receptor, MAGE family of tumour antigens (for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE family of tumour antigens (for example, GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p2Iras, RCAS1, α-foetoprotein, E-cadherin, α-catenin, 13-catenin, γ-catenin, pl2Octn, gp100Pme1117, PRAME, NY-ESO-1, cdc27, adenomatous polyposis of the colon protein (APC), fodrin, Connexin 37, idiotype Ig, p15, gp75, GM2 and GD2 gangliosides, viral products such as the proteins of the human papillomavirus, Smad family of tumour antigens, Imp-1, PIA, EBV encoded nuclear antigen (EBNA)-1, brain glycogen phosphorylase, SSX-1, SSX-2 (HOM-MEL-40), SSX-3, SSX-4, SSX-5, SCP-1 and CT-7, and c-erbB-2, acute lymphoblastic leukaemia (etv6, amII, cyclophilin b), B cell lymphoma (idiotype Ig), glioma (E-cadherin, a-catenin, 13-catenin, 7-catenin, p120ctn), bladder cancer (p2Iras), biliary cancer (p2Iras), breast cancer (MUC family, HER2/neu, c-erbB-2), carcinoma of the cervix (p53, p2Iras), carcinoma of the colon (p2Iras, HER2/neu, c-erbB-2, MUC family), colorectal cancer (colorectal associated antigen (CRC)-0017-1A/GA733, APC), choriocarcinoma (CEA), epithelial cell cancer (cyclophilin b), gastric cancer (HER2/neu, c-erbB-2, ga733 glycoprotein), hepatocellular cancer, Hodgkin's lymphoma (Imp-1, EBNA-1), lung cancer (CEA, MAGE-3, NY-ESO-1), lymphoid cell-derived leukaemia (cyclophilin b), melanoma (p15 protein, gp75, oncofetal antigen, GM2 and GD2 gangliosides, Melan-A/MART-1, cdc27, MAGE-3, p2Iras, gp100Pme1117), myeloma (MUC family, p2Iras), non-small cell lung cancer (HER2/neu, c-erbB-2), nasopharyngeal cancer (Imp-1, EBNA-1), ovarian cancer (MUC family, HER2/neu, c-erbB-2), prostate cancer (prostate specific antigen (PSA) and its antigenic epitopes PSA-1, PSA-2 and PSA-3, PSMA, HER2/neu, c-erbB-2, ga733 glycoprotein), renal cancer (HER2/neu, c-erbB-2), squamous cell cancers of the cervix and oesophagus (viral products such as human papillomavirus proteins), testicular cancer (NY-ES0-1) and T-cell leukaemia (HTLV-1 epitopes).

The components of the compositions of the invention, specifically, the fusion of Apo A and IL15 or the polynucleotide encoding said fusion and the Sushi domain of the IL15 receptor alpha chain or the nucleic acid encoding said domain can be presented as a single formulation (for example, as a tablet or capsule comprising a fixed amount of each component) or, otherwise, can be presented as separate formulations for subsequent combination for joint, sequential or separate administration. The compositions of the invention also contemplate the formulation as a kit of parts wherein the components are formulated separately but are packaged in the same container.

The expert in the art will appreciate that the formulation of the first and second component of the compositions of the invention can be similar, in other words, formulated in a similar way (for example, in tablets or in pills), allowing administration by the same route. In an embodiment wherein the different components of the invention are formulated separately, the two components can be presented in a blister pack. Each blister will contain the medicaments to be consumed throughout the day. If the medicaments need to be administered several times a day, the medicaments corresponding to each administration can be arranged in separate sections of the blister pack, preferably noting on each section of the blister pack the time of day when they need to be administered. Alternatively, the components of the composition of the invention can be formulated in a different manner so that the different components are administered differently. Thus, it is possible, for example, for the first component to be formulated as a tablet or capsule for oral administration and for the second component to be formulated for intravenous administration.

The compositions of the invention are administered according to methods known to an expert in the art, including, without limitation, intravenous, oral, nasal, parenteral, topical, transdermic, rectal and similar.

The invention is described below through the following examples which are purely illustrative and not !imitative of the scope of the invention.

EXAMPLES

Example 1

Origin and Construction of Plasmids 1.1 RNA Extraction

Total mouse liver RNA was isolated from individual samples using TRI reagent (Sigma, Madrid, Spain). The concentration and purity of the samples was determined by absorbance at 260 and 280 nm with background correction at 320 nm in a spectrophotometer (Biophotometer, Eppendorf).

1.2 RT-PCR Synthesis of Total cDNA

Total RNA (3 µg) was treated with DNase I and retrotranscribed to cDNA with M-MLV RT in the presence of RNase OUT (all reagents of Invitrogen, Carfsbed, Calif.). 25 µl were obtained of total liver cDNA. The reaction was incubated for 1 h at 37° C., denatured for 1 min at 95° C. and taken to 4° C. The samples were used immediately for PCR or kept at −20° C.

1.3 Cloning the cDNA of Murine Apolipoprotein A-1 (mApoA1) and Obtaining the Plasmid pCMV-mApoA1 pCMV-mApoA1 (pApo) comprises a sequence SEQ ID NO:1 encoding a polypeptide comprising murine apolipoprotein A-I (Apoa1) preceded by its own signal peptide, and which is operatively joined to the cytomegalovirus promoter;

```
The sense primer FwATGmApoA1:
                                    (SEQ ID NO: 46)
5'-ATGAAAGCTGTGGTGCTGGC-3' was designed,
and antisense primer RvTGAmApoA1:
                                    (SEQ ID NO: 47)
5'-TCACTGGGCAGTCAGAGTCT-3'.
```

The cDNA of mApoA1 was amplified (795 total nucleotides, 72 nucleotides encoding the signal peptide and 723 nucleotides encoding the native protein) by PCR on total liver cDNA, using BioTaq DNA polymerase (Bioline, London, UK): 5 min 94° C., 30 cycles of 40 sec at 94° C., 40 sec at 55° C. and 40 sec at 72° C., followed by 7 min at 72° C. in the 2720 Thermal cycler (Applied Biosystems, Foster City, US). The product of PCR was migrated in 1% Agarose D-1 low EEO agarose gel (Pronadisa, Madrid, Spain), purifying the gel fragment using QIAquick Gel Extraction Kit (Qiagen, Valencia, Calif.). The purified cDNA of mApoA1 was cloned, following the manufacturer's instructions, in the expression vector pcDNA™3.1/V5-His TOPO® TA (Invitrogen, Carfsbed, Calif.), to be referred to as pCMV-mApoA1 or also as pApo. Finally, the obtained sequence was confirmed by sequencing.

1.4 Cloning the cDNA of Human Interleukin 15 (hIL15) and Obtaining the Plasmid pCMV-hIL15 pCMV-hIL15 (phIL15) comprises a sequence SEQ ID NO:2 encoding a polypeptide comprising human IL15 preceded by the signal peptide of the IgV$_\chi$ chain, and which is operatively joined to the cytomegalovirus promoter;

The sense primer FwAsclhIL15:
5"-AATAATGGCGCGCCGAACTGGATAGATG-3' (SEQ ID NO:48), was designed, which introduces the sequence of 9 nucleotides (GGCGCGCCC) that constitute a restriction site for enzyme AscI in 5';
and the antisense primer RvNotlh IL15:

```
                                    (SEQ ID NO: 49)
5'-GTTCATCAACACGTCCTGAGCGGCCGC-3',
``` which introduces the sequence of 8 nucleotides (GCGGCCGC) that constitute a restriction site for enzyme NotI in 5'.

The cDNA of hIL15 was amplified (345 total nucleotides) by PCR on the expression plasmid pVkL/IL-15IRESneo (Meazza et al. Eur. J. Immunol. 1997; 27: 1049-1054). This plasmid contains the sequence encoding human mature IL15 preceded by the IgV$_\chi$ chain, under the control of the cytomegalovirus promoter. The term pCMV-hIL5 or phIL15 will be used to refer to it.

The PCR was carried out using EasyA high fidelity PCR Cloning Enzyme (Stratagene,Cedar Creek,Tex., US). The amplification conditions were: 2 min 95° C., 30 cycles of 40 sec at 95° C., 30 sec at 57° C. and 45 sec at 72° C., followed by 7 min at 72° C. in the 2720 Thermal cycler (Applied Biosystems Foster City, US). The product of PCR was migrated in 1% Agarose D-1 low EEO agarose gel (Pronadisa, Madrid, Spain), purifying the gel fragment using the QIAquick Gel Extraction Kit (Qiagen, Valencia, Calif.). The purified cDNA of hIL15 was cloned, following the instructions provided, in expression vector pTrcHis2 TOPO® TA (Invitrogen, Carfsbed, Calif.), which is to be referred to as pTrcHis2-hIL15. Finally, the obtained sequence was confirmed by sequencing.

1.5 Construction of Plasmid DCMV-Apo-hIL15 (pApo-hIL15) Encoding the Gene Fusion of mApoA1 and hIL15 pCMV-Apo-hIL15 (pApo-hIL15), comprises a sequence SEQ ID NO: 40, which encodes a fusion protein comprising murine apolipoprotein A-I, joined to human IL15 by a GAP linker, and that is operatively joined to the cytomegalovirus promoter; and The antisense primer RvAsclmApoA1:
5'-GGCGCGCCCTGGGCAGTCAGAGTCTCGC-3' (SEQ ID NO:50) was designed, which introduces the sequence of 9 nucleotides (GGCGCGCCC) that constitutes a restriction site for enzyme AscI in 3' of the ApoA1 gene and eliminates the stop codon. This added restriction sequence will translate into a short linker peptide GAP, which will give certain mobility to the constituent proteins.

Amplification was by PCR, using as a template pCMV-mApoA1 (see example 1.3), and primers FwATGmApoA1 and RvAsclmApoA1, with the BioTaq DNA polymerase enzyme (Bioline, London, UK), 5 min 94° C., 30 cycles of 40 sec at 94° C., 40 sec at 57° C. and 40 sec at 72° C., followed by 7 min at 72° C. in the 2720 Thermal cycler (Applied Biosystems Foster City, US). The product of PCR (804 nucleotides) was migrated in 1% Agarose D-1 low EEO agarose gel (Pronadisa, Madrid, Spain), purifying the gel fragment using the QIAquick Gel Extraction Kit (Qiagen, Valencia, Calif.). The purified DNA of mApoA1-AscI was cloned, following the instructions provided, in the expression vector pcDNA™3.1/V5-His TOPO® TA (Invitrogen, Carfsbed, Calif.), to be referred to as pCMV-mApoA1-AscI. Finally, the obtained sequence was confirmed by sequencing.

In parallel, using as a template pTrcHis2-hIL15 (see example 1.4) it was digested 50 min at 37° C. with the AscI enzyme and Buffer 4 (New England Biolabs). The product of digestion was migrated in 1% Agarose D-1 low EEO agarose gel (Pronadisa, Madrid, Spain), purifying the gel fragment using the QIAquick Gel Extraction Kit (Qiagen, Valencia, Calif.). The purified DNA AscI-hIL15-pTrcHis2 was then digested for 50 min at 37° C. with the enzyme NotO, 1×BSA and Buffer 3 (New England Biolabs). The product of digestion was migrated in 1% Agarose D-1 low EEO agarose gel (Pronadisa, Madrid, Spain), purifying the gel fragment using the QIAquick Gel Extraction Kit (Qiagen, Valencia, Calif.), obtaining the purified DNA AscI-hIL15-NotI (345 nucleotides).

To perform the gene fusion, plasmid pCMV-mApoA1-AscI was digested 50 min at 37° C. with AscI enzyme and Buffer 4 (New England Biolabs). The product of digestion was migrated in 1% Agarose D-1 low EEO agarose gel (Pronadisa, Madrid, Spain), purifying the gel fragment using the QIAquick Gel Extraction Kit (Qiagen, Valencia, Calif.). The purified DNA pCMV-mApoA1 was then digested 50 min at 37° C. with NotI enzyme, 1×BSA and Buffer 3 (New England Biolabs) taking advantage of the restriction site present in the skeleton of pcDNA 3.1 V5-His TOPO® TA. The product of digestion was migrated in 1% Agarose D-1 low EEO agarose gel (Pronadisa, Madrid, Spain), purifying the gel fragment using the QIAquick Gel Extraction Kit (Qiagen, Valencia, Calif.). The vector opened by AscI and NotI pCMV-mApoA1 was bound to the insert AscI-hIL15-NotI in a ratio of 1:3 (vector: insert) using T4 DNA ligase High Concentration and as buffer solution 2×Rapid Ligation Buffer (Promega Madison, Wis., U.S.), incubating the mixture 10 min at room temperature. Subsequently Top10 bacteria (Invitrogen, Carfsbed, Calif.) were transformed. The transformed bacteria were selected for their growth in Petri plates with LB medium with ampicillin, since the vector contains a resistance gene to this antibiotic. Plasmidic DNA was extracted from the positive bacteria using the MiniPrep technique (Qiagen, Germany) for subsequent digestion of 2 µg of said plasmid with AscI/PmeI enzymes (New England Biolabs) and separation by electrophoresis of the result of said digestion in 1% agarose gel to check the presence of the insert. The resulting 6669 nts plasmid is hereinafter referred to as pCMV-Apo-hIL15 or also as pApo-hIL15.

1.6 Origin of the pSushi Plasmid

The plasmid referred to in the context of this invention as pCMV-Sushi (pSushi) corresponds to plasmid IL-15RΔMD previously described by Duitmann et al. (Duitman, E. H., et al., Mol Cell Biol, 2008; 28: 4851-4861), kindly provided by the authors of this work.

pCMV-Sushi (pSushi) contains a sequence SEQ ID NO:20 encoding a polypeptide that comprises the Sushi domain of the murine 1L15 receptor α chain (IL15ra), preceded by a signal peptide of Igκ, and that is operatively bound to the cytomegalovirus promoter.

1.7 Cloning the cDNA of Murine Interleukin 15 (mIL15) and Obtaining Plasmid pCMV-mSushi-mIL15 (pmSushi-mIL15)

pCMV-mSushi-mIL15 (pmSushi-mIL15), comprises a sequence encoding a polypeptide that comprises the Sushi domain of the murine IL15 receptor α chain (IL15ra), bound to the murine IL15 by a flexible linker of the type GGSGGGGSGGGSGGGGSLQ (SEQ ID NO:32).

The gene encoding the Sushi domain fused to the murine IL15 followed by two stop codons flanked by one NheI restriction site in 3' and another XhoI in 5', was synthesised by GENEART AG (GENEART AG, BioPark, Josef-Engert-Straβe 11, 93053 Regensburg, Germany) and introduced in the plasmid pSecTag2/Hygro A (Invitrogen, Frankfurter Straβe 129B, 64293 Darmstadt, Germany).

The expression of the Sushi domain fused to the murine IL15 is under the control of the cytomegalovirus promoter and its secretion is directed under the Igκ-chain V-J2 signal peptide.

1.8 Construction of the Plasmid pCMV-mSushi-mIL15-mApoA1 (pmSushi-mIL15-mApo) Encoding the Gene Fusion of mSushi, mIL15 and mApoA1 pCMV-mSushi-mIL15-mApoA1, comprises a sequence SEQ ID NO:45 encoding a fusion protein comprising the Sushi domain of the murine IL15 receptor α chain (IL15ra), murine IL15, and murine apolipoprotein A-I.

Primers were designed to amplify the Sushi sequence fused to the murine IL15 and to join to it at the same time the sequence of 9 nucleotides (GGCGCGCC) that constitutes a restriction site for the AscI enzyme in 3' of the gene and eliminates the stop codon. This added restriction sequence will allow cloning with an Apo sequence that contains the AscI sequence in 5' and will translate into a GAP short linker peptide, which will give certain mobility to the constituent proteins.

The primers were:

```
                                       (SEQ ID NO: 51)
Fw Sushi       5'-ATGGAGACAGACACCCTGCTG-3'

(SEQ ID NO: 52)
Rv IL15 AscI:  5'-GGGCGCGCCGCTGGTGTTGATGAACAT-3'
```

The sequence was amplified by PCR, using as a template the pmSushi-mIL15 described in the previous example, and the primers Fw Sushi and Rv IL15 AscI, with enzyme BioTaq DNA polymerase (Bioline, London, UK), 1 min 94° C., 30 cycles of 30 sec at 94° C., 30 sec at 58° C. and 45 sec at 72° C., followed by 2 min at 72° C. in the 2720 Thermal cycler (Applied Biosystems Foster City, US). The product of PCR was migrated in 1% Agarose D-1 low EEO agarose gel (Pronadisa, Madrid, Spain), purifying the gel fragment using the QIAquick Gel Extraction Kit (Qiagen, Valencia, Calif.). The purified DNA was cloned, following the instructions provided, in the expression vector pcDNA™3.1/V5-His TOPO® TA (Invitrogen, Carfsbed, Calif.), to be referred to as pCMV-mSushi-mIL15-AscI. Finally, the obtained sequence was confirmed by sequencing.

To perform the gene fusion, plasmid pCMV-mIFN-AscI-mApo (described in patent application WO2009150284 and comprising a polynucleotide encoding a fusion protein between mIFN and mApo), was digested for 50 min at 37° C. with enzymes AscI and NcoI in Buffer 4 (New England Biolabs). The product of the digestion was migrated in 1% Agarose D-1 low EEO agarose gel (Pronadisa, Madrid, Spain), and the upper band containing the open vector without the IFN sequence was purified from the gel using the QIAquick Gel Extraction Kit (Qiagen, Valencia, Calif.). The plasmid pCMV-mSushi-mIL15-AscI was digested using the same enzymes and conditions. In this case the lower band containing the mSushi-mIL15 fragment was purified. Both purified fragments were bound in a ratio of 1:3 (vector: insert) using T4 DNA ligase High Concentration and as buffer solution 2×Rapid Ligation Buffer (Promega Madison, Wis., U.S.), incubating the mixture for 10 min at room temperature. Subsequently Top10 bacteria (Invitrogen, Carfsbed, Calif.) were transformed. The transformed bacteria were selected for their growth in Petri plates with LB medium with ampicillin, since the vector contains a resistance gene to this antibiotic. Plasmidic DNA was extracted from the positive bacteria using the MiniPrep technique (Qiagen, Germany) for subsequent digestion of 2 µg of said plasmid with enzymes AscI/PmeI (New England Biolabs) and separation by electrophoresis of the result of said digestion in 1% agarose gel to check the presence of the insert. The resulting plasmid is hereafter referred to as pCMV-mSushi-mIL15-mApoA1 or also as amSushi-mIL15-mApo.

Example 2

Experimental Models 2.1 Animals

Experiments were performed on female immunocompetent BALB/c and C57BL/6 mice between 5-7 weeks old (Harlan, Barcelona, Spain). "Knock-out" mice were used for the IL15Rα gene (Lodolce et al. IL15 receptor maintains lymphoid homeostasis by supporting lymphocyte homing and proliferation. *Immunity* 1998; 9: 669-676). The animals were treated in accordance with ethical rules for animal experimentation, under specific conditions free from external pathogens.

2.2 Animal Handling

Each DNA plasmid (10 µg) was resuspended in 1.8 ml saline serum 0.9% (Braun) introduced in the tail vein by hydrodynamic injection, using 27.5G needles and 2.5 ml syringes (Becton-Dickinson, Spain). Blood samples were obtained retroorbitally, following inhalatory anaesthesia with isoflurane (Forane, Abbott). The serum was recovered through two consecutive centrifugations at 9.1×g during 5 minutes and stored at −20° C. The parenteral anaesthesia was carried out by intraperitoneal injection of 200 µl/mouse with a 9:1 mixture of ketamine (Imalgene) and xylazine (Rompun).

2.3 Cell Lines

The CT26 cell line derives from a BALB/C mouse colorectal adenocarcinoma, and was induced by the carcinogen N-nitrous-N-methyl-urethane.

The MC38 line comes from a murine adenocarcinoma.

Both were cultured in complete RPMI-1640 medium (Gibco-BRL, Paisley, UK), supplemented with 10% foetal calf serum (FCS) inactivated at 56° C., 2 mM glutamine, 100 U/ml streptomycin, 100 mg/ml penicillin, 1% β-mercaptoethanol 5.10-3. The described cells were cultured in humidified incubating chambers at 37° C. and at an atmosphere of 5% $CO_2$. The culture plates and bottles were supplied by Greiner Bio-one (Essen, Germany).

2.4 Determination of hIL15

Serum levels of hIL15 were measured by ELISA assay in NUNC MaxiSorp flat-bottom 96-well plates using an ELISA kit (Set Human IL15, BD Biosiences, San Diego, Calif., US), following the manufacturer's instructions.

2.5 Flow Cytometry

Cell populations were studied by flow cytometry. To this effect blood obtained retroorbitally as well as from animals' spleen and liver was used. Solid organs were incubated during 15 min with a collagenase and DNAse solution to facilitate cellular disintegration, which was carried out with the help of a Cell Strainer© (BC Falcon, Bedford, Mass., US). The liver lymphocytes were isolated by centrifugation of the cellular suspension in 35% Percoll© solution (GE Heathcare, Uppsala, Sweden). For each liver, the following reagents were used: 1.6 mL of PBS 10×, 15.8 mL of Percoll©, 200U of Heparin (Mayne Pharma, Madrid, Spain) and 28 mL of RPMI (Gibco, Invitrogen, Grand Island, N.Y., US).

All studied cellular suspensions were treated with Tris $NH_4Cl$ buffer during 5 minutes to lysate erythrocytes.

Cells were resuspended in 50 µL of PBS and incubated during 10 min at 4° C. in darkness with the mixture of corresponding antibodies. Subsequently two washes were made and they were analysed in a FACScalibur© cytometer (BD Bioscience, San Diego, Calif., US). The subsequent data analysis was carried out using the Flow program Version 5.7.2.

The antibodies used were NK1.1-PE, CD3-FITC, CD8-PE, CD44-APC, CD62L-PE, CD8-PECy7 and NK1.1-APC (BD-Pharmamingen, BD Bioscience, San Diego, Calif., US).

2.6 Statistical Data Analysis

Data were statistically analysed using the Prism 5 computer program (GraphPad Software, Inc.). Data on tumour appearance were recorded on Kaplan-Meier graphs. Data studied at different times were analysed by repeated measurement ANOVA followed by the Bonferroni test. Significant values were considered p<0.05.

Example 3

Circulating Levels of hIL15 Following Hydrodynamic Administration of the Plasmid Constructs To study the levels of human hIL15 in mouse serum, groups of 2-3 mice were arranged and each mouse was hydrodynamically administered 10 µg of the corresponding plasmid (or combination of plasmids). The plasmids injected into the different groups were: pApo-hIL15, pApo-hIL15+pSushi, phIL15, phIL15+pSushi, pApo or saline (S).

Serum samples were obtained at 8, 24, 96, 168 and 240 hours and hIL15 concentration in them was determined by an ELISA sandwich assay. Sera of the mice receiving the control plasmid which expresses ApoA1 did not contain detectable levels of hIL15 (FIG. 1). Mice that had been injected with the plasmid expressing hIL15 presented maximum hIL15 concentrations at 8 h which rapidly decreased (FIG. 1). However, mice receiving the plasmids encoding ApoA1-hIL15 (with or without co-infection of the pSushi plasmid) presented higher serum hIL15 concentrations at 8 h, which continued to increase up to 24 h. At 168h it was still possible to detect hIL15 in mice treated with pApo-hIL15 in contrast to that observed in mice injected with phIL15 (FIG. 1). Therefore, the constructs expressing fusion proteins ApoA1-hIL15 achieve higher and longer-lasting circulating levels of hIL15.

To conclude, hydrodynamic administration of plasmid pApo-hIL15 induces high serum concentrations of hIL15, far exceeding those produced by the administration of phIL15.

Example 4

Functional assay in CTLL2 cells

To study the pharmacodynamic effects of the pApo-hIL15 plasmid, a functional assay was carried out using CTLL2 cells, which require IL-2 or IL15 in order to proliferate (Meazza et al. Expression of two interleukin-15 mRNA isoforms in human tumors does not correlate with secretion: role of different signal peptides. *Eur J Immunol* 1997; 27: 1049-1054).

Figure 2:
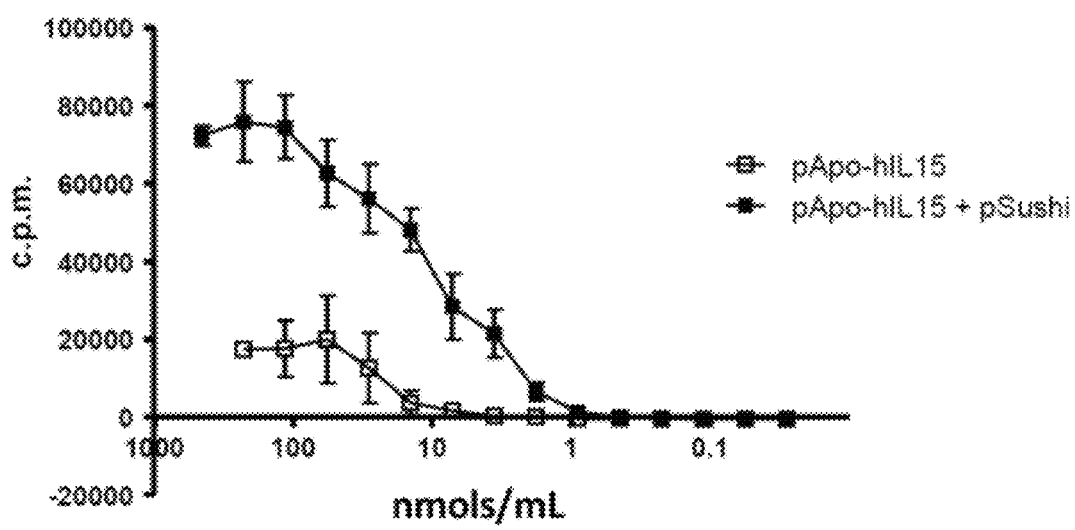
FIG. 2. Functional proliferation assay of pApo-hIL15 co-administered with pSushi by hydrodynamic injection. CTLL2 cells were cultured in serial dilutions of serums obtained 24 hours after treating mice with pApo-hIL15 and pApo-hIL15+pSushi. At 48 h the incorporation of tritiated thymidine into CTLL2 cells was studied as a proliferation index (c.p.m.) observing that mice sera treated with pApo-hIL15 and pSushi simultaneously induced a higher proliferation than the sera of mice treated only with pApo-hIL15 ($p<0.001$). The mean and mean standard deviation of a representative experiment with 4-5 animals per group is shown. The results were statistically compared by repeated measurement ANOVA.

The plasmids were administered by hydrodynamic injection and serum samples were obtained at 24 h. Serum was decomplemented by heat denaturation (45 minutes 56° C.) and added to CTLL2 cell cultures during 48 h, and cellular proliferation was measured with tritiated thymidine. Serum concentration of hIL15 was measured using a commercial ELISA sandwich assay. In terms of the equimolar quantities of hIL15, mouse serum treated with pApo-hIL15+pSushi induced a more intense proliferation of CTLL2 cells (FIG. 2).

Therefore, it is concluded that co-administration of the pSushi plasmid with pApo-hIL15 increases its biological effect. The plasmid constructs of ApoA1 fused with hIL15 presented a higher induction effect of CTLL2 cell proliferation than when administered with a plasmid encoding the sushi domain (pSushi) of IL15Rα.

Example 5

Stimulation of CD8 Lymphocyte Proliferation

Figure 3:
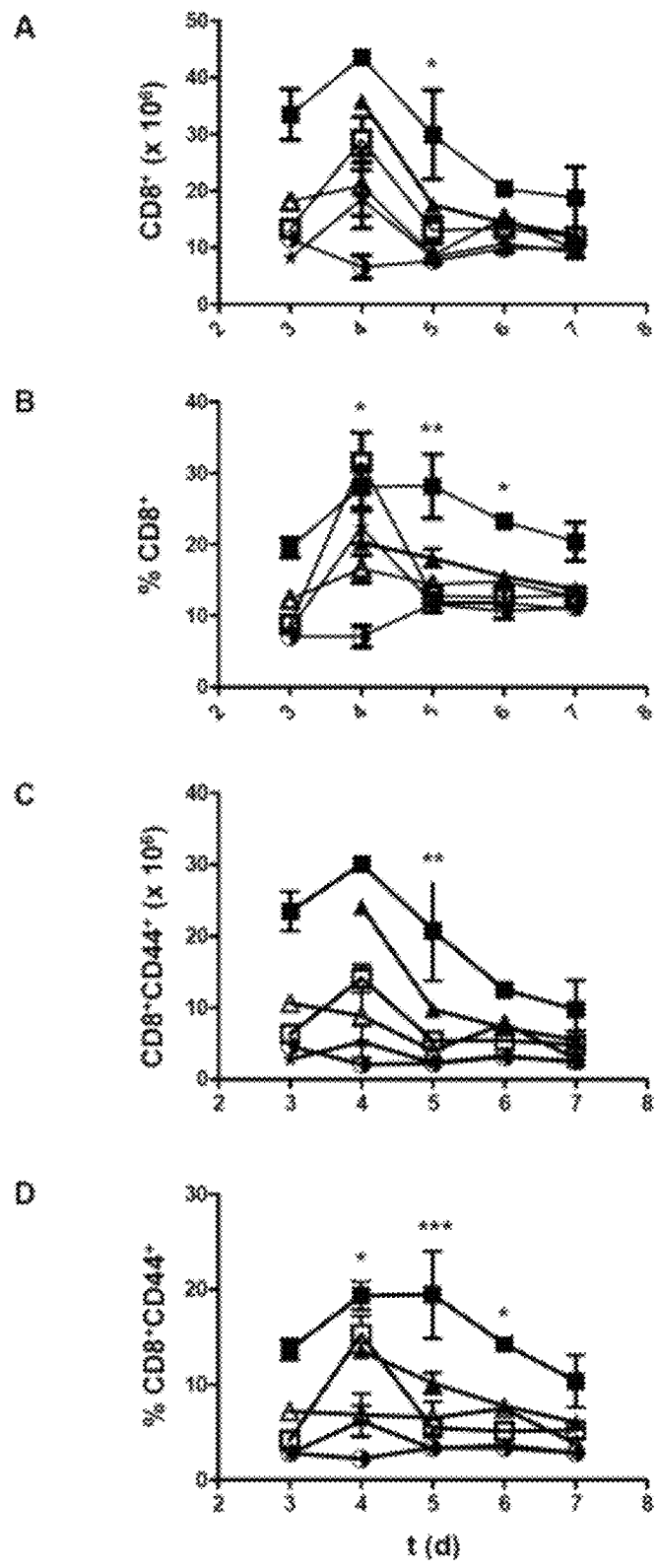
FIG. 3. Increase in total number and percentage of $CD8^+$ T cells in relation to total splenocytes over time (t (d), in days). Groups of C57B16 mice received a hydrodynamic injection of the different plasmid constructs and at 3, 4, 5, 6 and 7 days were sacrificed and spleens removed. The number of $CD8^+$ T cells were measured (A), the percentage of $CD8^+$ T cells in relation to total splenocytes (B), the number of $CD8^+CD44^+$ memory T cells (C) and the percentage of $CD8^+CD44^+$ memory T cells in respect of total splenocytes (D). The group of mice to which plasmids pApo-hIL15 and pSushi (■) were administered present a higher number of $CD8^+$ T cells in relation to other groups: pApo-hIL15 (□), phIL15 +pSushi (▲), phIL15 (Δ), pApo (○) and saline vehicle (*). The mean and mean standard deviation of a representative experiment with 2 animals per group is shown. Data were analysed by a repeated measurement ANOVA followed by a Bonferroni test comparing the pApo-hIL15+pSushi group and the phIL15+pSushi group * $p<0.05$;  $p<0.001$; * $p<0.0001$.

In order to study the potential immunostimulant effect of the constructs expressed in the liver by means of hydrodynamic injection, first the increase in number of CD8 T cells in spleen was analysed. To do this, the plasmids were injected hydrodynamically and 3, 4, 5, 6 and 7 days later, spleens were disintegrated to obtain a unicellular suspension, total cells were counted and, after labelling CD8 T lymphocytes with anti-CD3, anti-CD8 and anti-CD44 antibodies were analysed by multicolour flow cytometry. The joint injection of plasmids pApo-hIL15 and pSushi increased the number of CD8 T lymphocytes in the spleen to a greater extent than the other treatments (FIG. 3A). The same happened with the number of memory CD8 T lymphocytes determined as CD3+, CD8+, CD44hi cells (FIG. 3C). The percentage of CD8 T and CD8 memory cells in relation to total splenocytes was also higher in the group of mice administered plasmids pApo-hIL15 and pSushi when compared to the other groups (FIGS. 3B and 3D).

Figure 4:
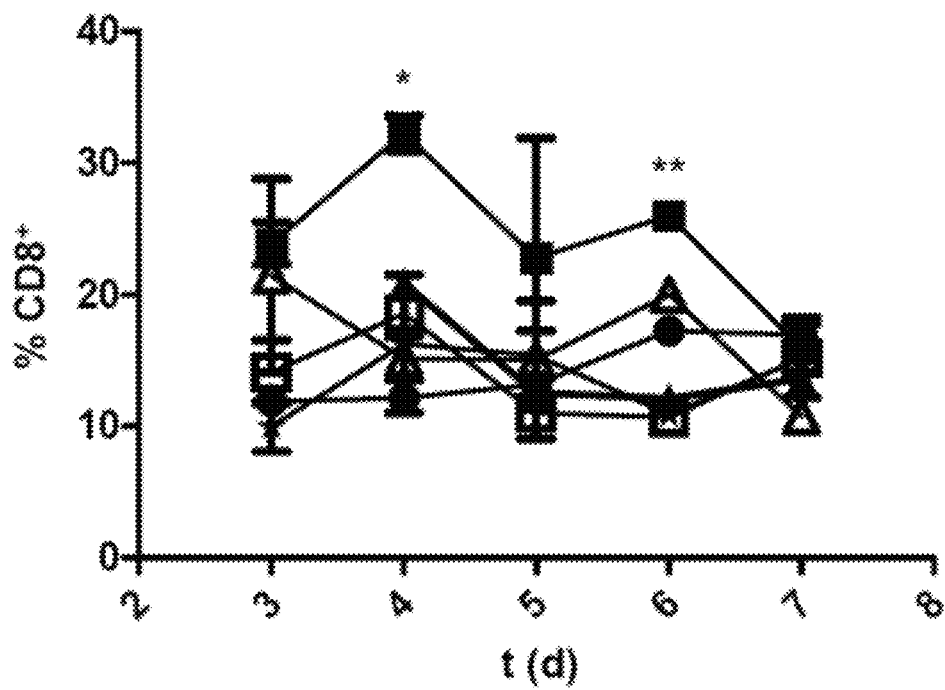
FIG. 4. Increase in the percentage of $CD8^+$ T cells in relation to total lymphocytes in liver over time (t (d), in days). C57B16 mice were hydrodynamically administered the different constructs. At 3, 4, 5, 6 and 7 days the animals were sacrificed and livers isolated. The percentage of $CD8^+$ T cells in relation to total lymphocytes was measured. The group of mice administered the plasmids pApo-hIL15 and pSushi (■) presented a higher percentage of $CD8^+$ T cells than the rest of the groups: pApo-hIL15 (□), phIL15+pSushi (▲), phIL15 (Δ), pApo (○) and saline vehicles (*). The mean and mean standard deviation of a representative experiment with 2 animals per group is shown. Data were analysed by repeated measurement ANOVA followed by a Bonferroni test comparing the pApo-hIL15+pSushi group and the phIL15+pSushi group * $p<0.05$;  $p<0.001$; * $p<0.0001$.

The percentage of CD8 T lymphocytes was also analysed in relation to the lymphocytes present in the liver of mice treated with the different plasmids. To do this, plasmids were injected hydrodynamically and at days 3, 4, 5, 6 and 7 livers were disintegrated, lymphocytes were isolated by centrifugation in a Percoll© solution and, after labelling the CD8 T lymphocytes with anti-CD3 and anti-CD8 antibodies, they were analysed by flow cytometry. Mice administered plasmids pApo-hIL15 and pSushi jointly presented a higher percentage of CD8 T lymphocytes in liver than the mice in the rest of the groups (FIG. 4).

Figure 5:
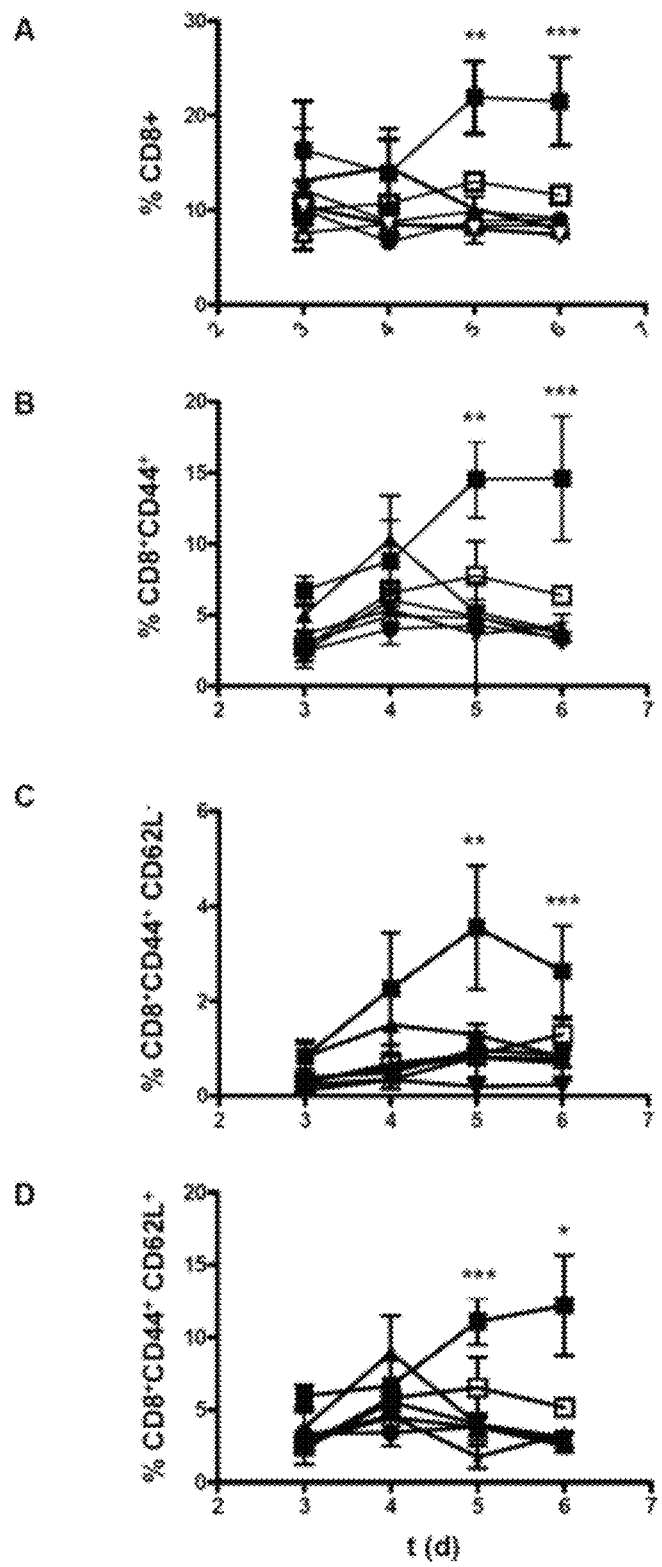
FIG. 5. Increase in total number and percentage of $CD8^+$ T cells in respect of peripheral blood lymphocytes. C57B16 mice were hydrodynamically administered the different constructs with phIL15. At 3, 4, 5 and 6 days blood was extracted and the percentage of $CD8^+$ T lymphocytes (A), of $CD8^+CD44^+$ memory T cells (B), and the percentages of effector memory cells $CD8^+CD44^+CD62L^-$ (C) and central memory cells $CD8^+CD44^+CD62L^+$ (D) were measured. In all studied populations, the group of mice receiving plasmids pApo-hIL15 and pSushi (■) presented a higher percentage of $CD8^+$ T cells in relation to the other groups: pApo-hIL15 (□), phIL15+pSushi (▲), phIL15 (Δ), pApo (●), pSushi ( ) and saline vehicle (*). The mean and mean standard deviation of a representative experiment with 3 animals per group is shown. Data were analysed by a repeated measurement ANOVA followed by a Bonferroni test comparing the pApo-hIL15+Sushi group and the phIL15+pSushi group * $p<0.05$;  $p<0.001$; * $p<0.0001$.

Subsequently, the percentage of CD8 T lymphocytes was analysed in relation to the lymphocytes present in the peripheral blood of the mice treated with the different plasmids. To do this, plasmids were injected hydrodynamically and at days 3, 4, 5 and 6 blood samples were obtained and CD8 T lymphocytes were labelled with anti-CD3, anti-CD8, anti-CD44 and anti-CD62L antibodies. They were analysed by flow cytometry. Mice administered plasmids pApo-hIL15 and pSushi jointly presented a higher percentage of CD8 T lymphocytes in peripheral blood than mice from the rest of the groups on days 5 and 6 following treatment (FIG. 5A). A higher percentage of CD8 T memory lymphocytes (CD8+ CD44+) was also observed in this group (FIG. 5B) and within the subpopulations of CD8 T effector memory cells (CD8+ CD44+CD62L−) and CD8 central memory cells (CD8+ CD44+CD62L+) (FIGS. 5C and 5d).

Studies of the number and percentage of CD8 T lymphocytes demonstrate that administration of pApo-hIL15 and pSushi induces more abundant populations of CD8 T lymphocytes in spleen, liver and peripheral blood than the administration of other plasmids. Specifically, administration of pApo-hIL15 and pSushi results in a significantly higher population of CD8 T lymphocytes in spleen, liver and blood than the administration of constructs phIL15 and pSushi.

Example 6

Antitumoral Effect of the ApoA1 and hIL15-Based Constructs on Subcutaneous CT26 Tumour Model To study the antitumoral effect of the ApoA1 and hIL15-based constructs injected hydrodynamically, a subcutaneous tumour model was chosen in Balb/c mice induced by the CT26 cell line derived from a colorectal adenocarcinoma. $5 \times 10^5$ cells per mouse were injected subcutaneously and treated at 3 days with the different constructs based on ApoA1, hIL15 and Sushi. Tumour size was measured calculating the product of 2 diameters twice a week with a digital calliper. Mice were sacrificed once the size exceeded 246 mm².

Figure 6:
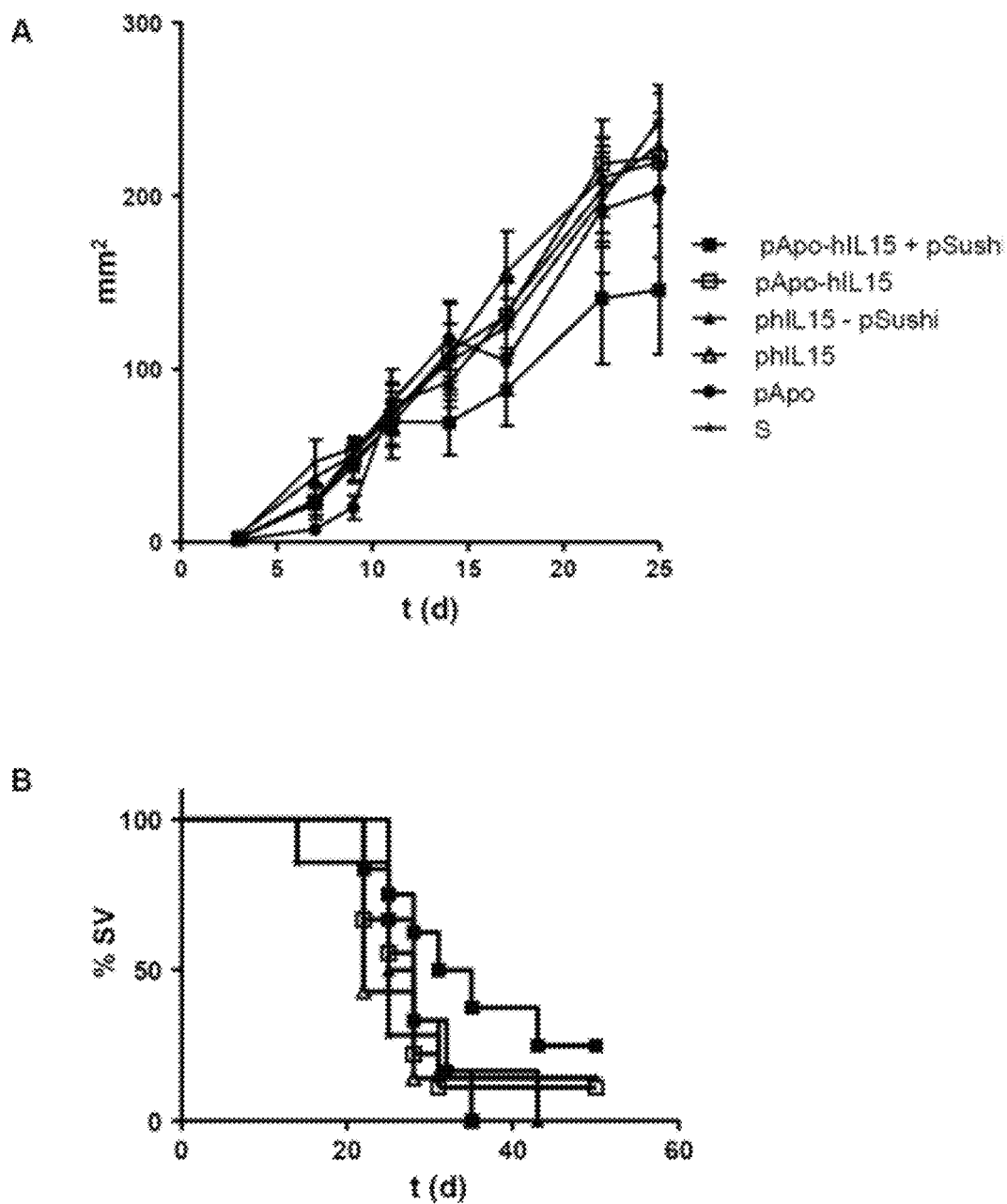
FIG. 6. Antitumoral effect over time (t (d), in days) of the constructs in the subcutaneous CT26 tumour model. Balb/c mice received $5\times10^5$ of CT26 cells subcutaneously and after 3 days were treated hydrodynamically with pApo-hIL15, pApo-hIL15+pSushi, phIL15, phIL15+pSushi, pApo or with saline solution (S). Tumours were measured in $mm^2$ using a digital calliper every 2 days (A), observing the animal's survival time (% SV) (B). Mice administered plasmids pApo-hIL15 and pSushi were observed to present delayed tumour growth and a higher survival rate than mice from the other groups. The mean and mean standard deviation of a representative experiment with 8 animals per group is shown.

Delayed tumour growth was observed in the group of mice treated with pApo-hIL15 and pSushi, which was not statistically significant (FIG. 6A). 25% of mice treated with pApo-hIL15 and pSushi survived 50 days after the tumour's inoculation and showed no visible tumour (FIG. 6B). 14% of mice treated with the pApo plasmid survived, as did 11% of mice treated with pApo-hIL15. No mouse of the other treatment groups survived the tumour. These data show that treatment with pApo-hIL15 and pSushi has certain antitumoral effects in the subcutaneous CT26 tumour model.

Example 7

Antitumoral Effect of the ApoA1 and hIL15-Based Constructs on the Subcutaneous MC38 Tumour Model In order to continue studying the antitumoral effect of the ApoA1 and hIL15-based constructs another model of subcutaneous tumour was selected. C57B16 mice were injected subcutaneously with $5 \times 10^5$ cells of the MC38 line and treated at 6 days with the different constructs based on ApoA1, hIL15 and Sushi for mice carrying tumoral nodules. Tumour size was measured calculating the product of 2 diameters twice a week with a digital calliper and mice were sacrificed once the size exceeded 246 mm².

Figure 7:
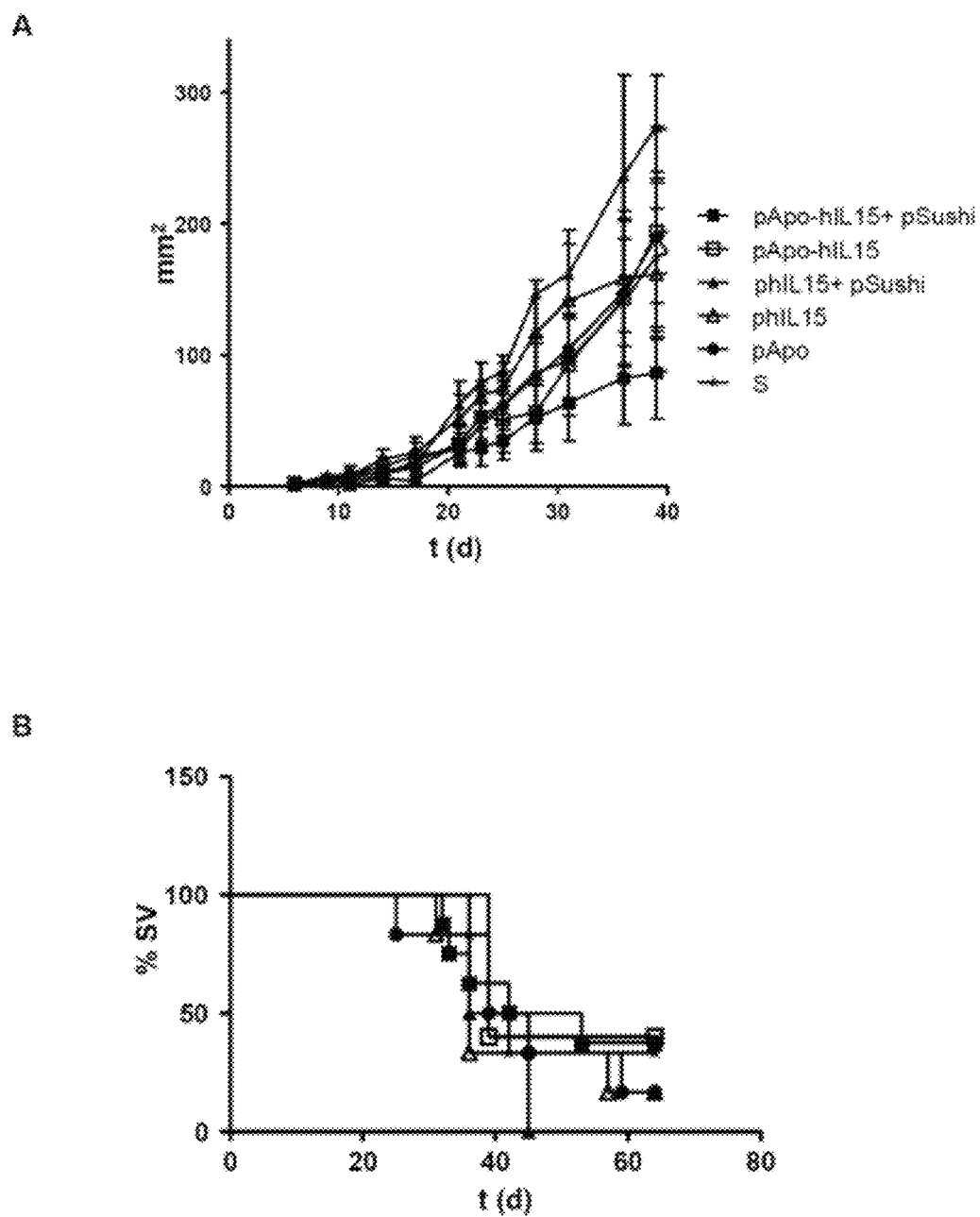
FIG. 7. Antitumoral effect over time (t (d): in days) of the plasmids in the subcutaneous MC38 tumour model. C57B16 mice were administered $5\times10^5$ of MC38 cells subcutaneously and after 6 days were treated hydrodynamically with pApo-hIL15, pApo-hIL15+pSushi, phIL15, phIL15+pSushi, pApo or saline solution (S). Tumours were measured in $mm^2$ using a digital calliper every 2 days (A), observing the animal's survival time (% SV) (B). Mice administered plasmids pApo-hIL15 and pSushi were observed to present delayed tumour growth. The mean and mean standard deviation of a representative experiment is shown.

Delayed tumour growth was observed in the group of mice treated with pApo-hIL15 and pSushi, which was not statistically significant (FIG. 7a). 37.6% of mice treated with pApo-hIL15 and pSushi survived 64 days from inoculation of the tumour and showed no visible tumour (FIG. 7b). 16.7% of mice treated with the pApo plasmid survived, as did 40% of mice treated with pApo-hIL15, 17% of those treated with phIL15 and 33% of those who received only saline (S). No mouse from the phIL15+pSushi group survived.

These data indicate that treatment with pApo-hIL15 and pSushi has certain antitumoral effects on the subcutaneous MC38 tumour model.

Example 8

Antimetastatic Effect of the ApoA1 and hIL15-Based Constructs on the Intrasplenic MC38 Tumour Model Study of the antitumoral effect of ApoA1 and hIL15-based constructs continued with an intrasplenic injection model of tumour cells that produce liver metastases.

C57B16 mice were injected intrasplenically with $5 \times 10^5$ cells per mouse of the MC38 line and treated the following day with the different constructs based on ApoA1, hIL15 and pSushi.

At 19 days mice were sacrificed and the number of metastases present in liver was observed. Mice were divided into 3 groups according to the number of metastases: I mice deceased due to massive liver metastases or generalised metastasis (it is not possible to observe healthy liver tissue at first sight); II mice presenting metastases in part of the liver tissue; III mice free of liver metastasis.

Figure 8:
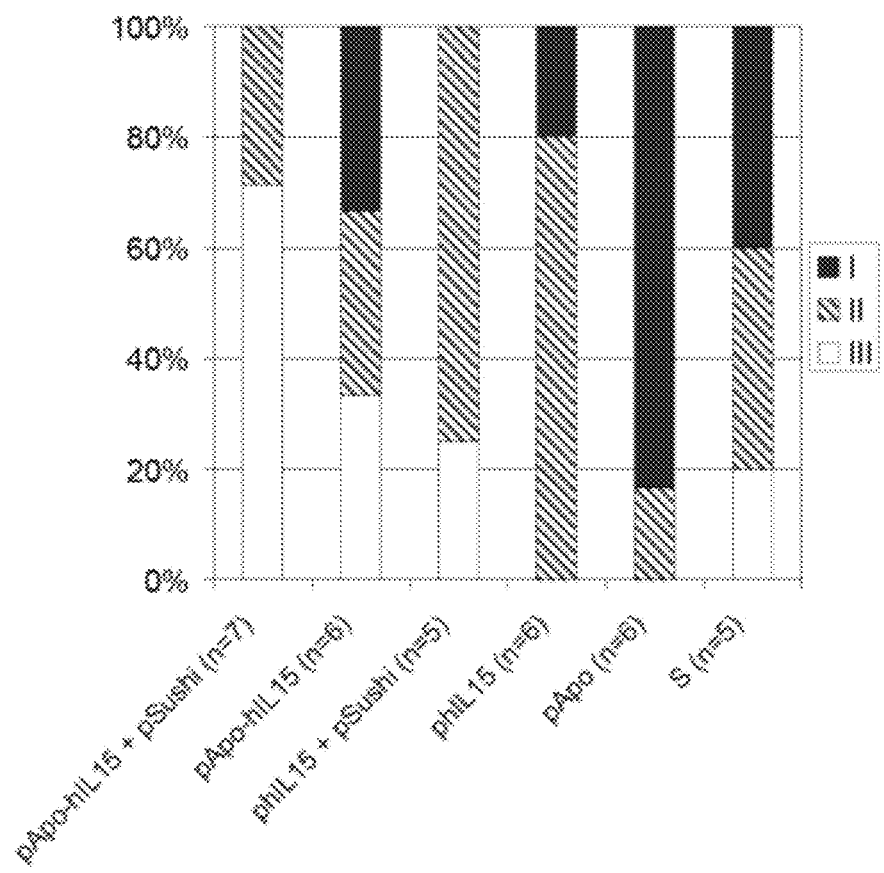
FIG. 8. Antimetastatic effect of the different plasmids in the intrasplenic MC38 tumour model. C57B16 mice were intrasplenically administered $5\times10^5$ of MC38 cells and the following day were treated hydrodynamically with pApo-hIL15, pApo-hIL15+pSushi, phIL15, phIL15+pSushi, pApo or saline solution (S). After 19 days the mice were sacrificed and divided into 3 groups: I, mice dead due to liver metastases or generalised metastasis; II, mice presenting metastases in part of the liver tissue; III, mice free of liver metastasis. Data of a representative experiment are shown.

In the group of mice treated with pApo-hIL15 and pSushi 71% presented a liver free of metastasis, against 30% of mice treated with pApo-hIL15, 25% treated with phIL15+pSushi, 20% of those receiving saline (S) and 0% of the phIL15 and pApo groups (FIG. 8).

From these data, it is concluded that administration of pApo-hIL15 and pSushi has more efficient antimetastatic effects than the other constructs studied in the intrasplenic MC38 tumour model.

Example 9

Effect of Administering ApoA1 and hIL15-based Constructs on "Knock Out" Mice for the IL15 α Receptor Studies continued of the immunostimulant effects of the ApoA1 and hIL15-based constructs on mice lacking the IL15 α receptor. These mice present a characteristic phenotype, since they lack NK cells and have a small amount of memory CD8 T cells (Lodolce et al. *Immunity* 1998; 9: 669-676).

Figure 9A:
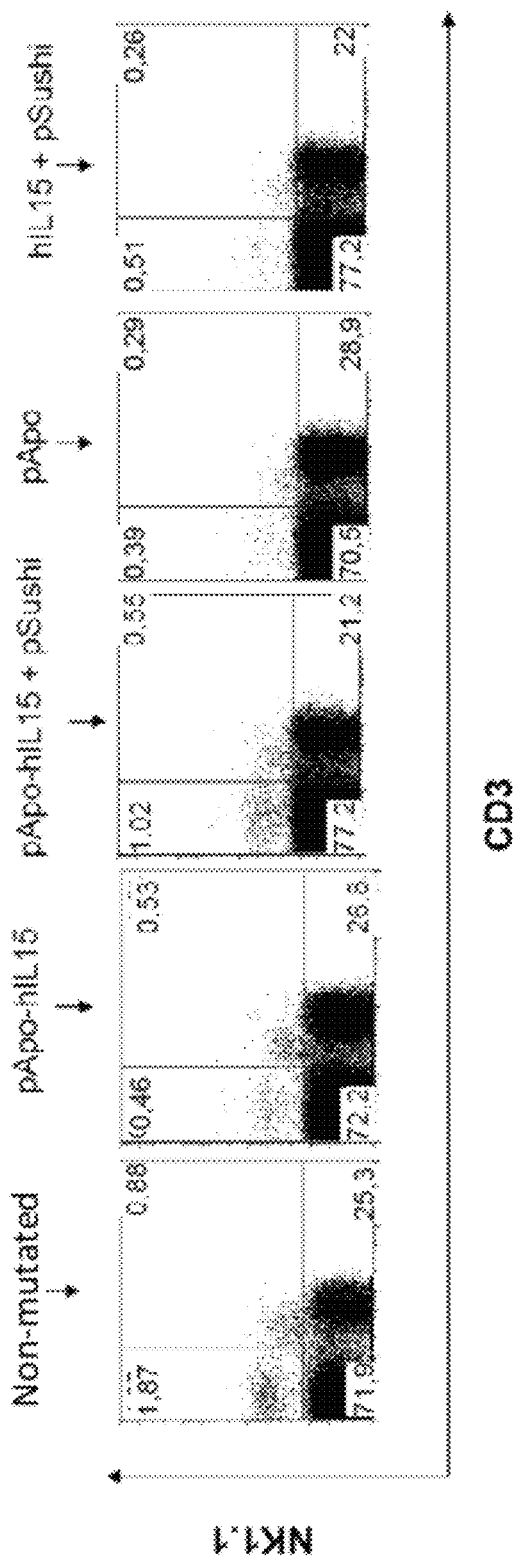
FIG. 9. Effect of the different plasmids in "knock out" mice for the α receptor of IL15. Four mice lacking the α receptor of IL15 were treated hydrodynamically with plasmids pApo-hIL15 and pSushi, phIL15 and pSushi, pApo and pApo-hIL15. Animals were sacrificed after 5 days, extracting the spleen and measuring the splenic populations of NK cells and CD8$^+$ T memory lymphocytes by flow cytometry using the CD3 marker for differentiation. The figure also includes NK and CD8$^+$ T memory populations of a non-mutated C57B16 mouse. The percentage of NK cells (A) of the CD8$^+$ T lymphocytes (B) and of the CD8$^+$CD44$^+$ subpopulation (C) of the studied mice are shown. Cell percentages in relation to total splenocytes are indicated.
Figure 9B:
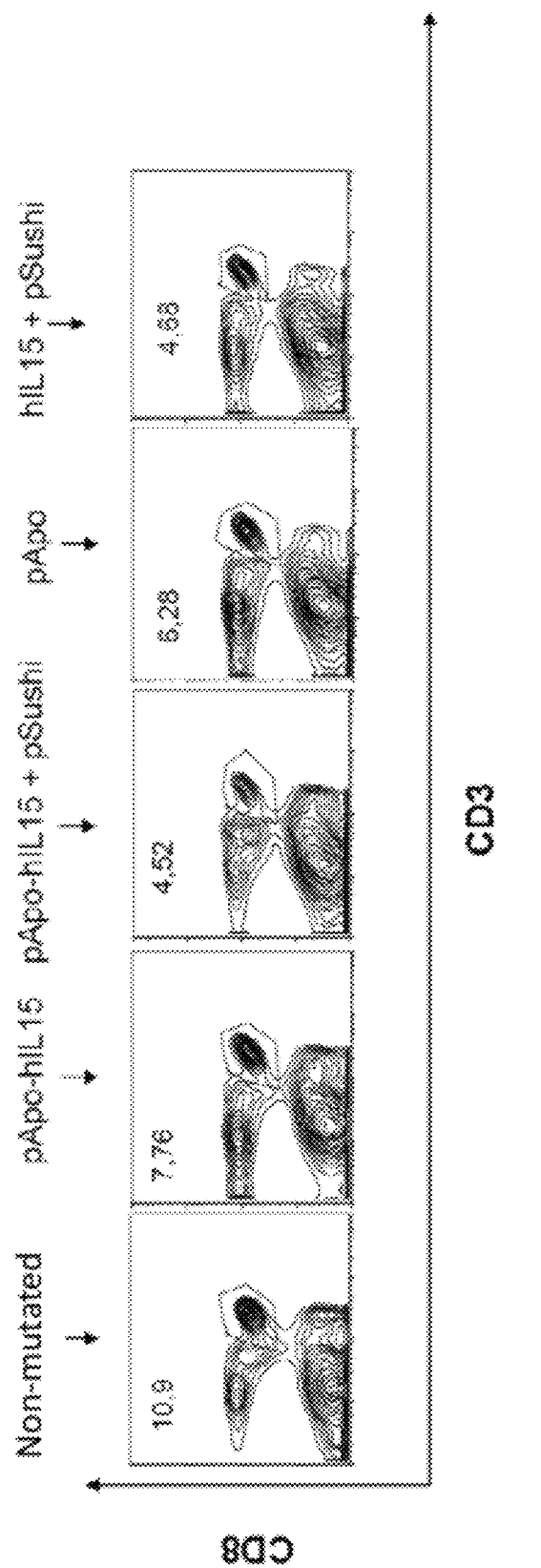
Figure 9C:
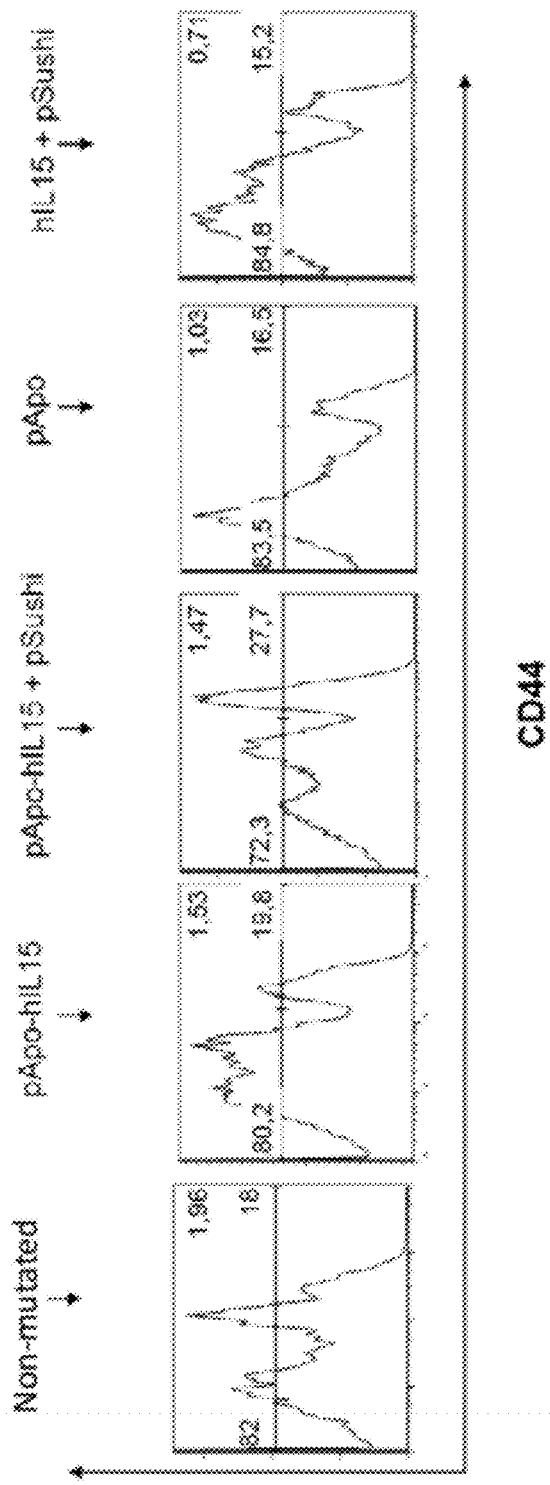

The purpose of this experiment was to observe whether pApo-hIL15 and pSushi could modify this phenotype. Four mice were injected, one with plasmids pApo-hIL15 and pSushi, one with phIL15 and pSushi, one with pApo and finally one with pApo-hIL15. At five days the mice were killed, the spleen removed and the splenic populations of NK cells and CD8 T memory lymphocytes were studied by flow cytometry (FIG. 9).

The mouse treated with plasmids pApo-hIL15 and pSushi presented a percentage of NK cells of 1.02%, far above the mouse treated with pApo (0.39%). As for the CD8 T memory lymphocytes of mice treated with pApo-hIL15 and pSushi there was 1.47% of CD8+ CD44+ cells in relation to total splenocytes. This percentage is similar to that achieved with the pApo-hIL15 construct alone. This experiment indicates that treatment with the pApo-hIL15 and pSushi constructs partially recovers the phenotype of the "knock out" mice for the IL15 α receptor, obtaining higher splenic percentages of NK and CD8 T memory cells than those obtained with the rest of the constructs under study.

Example 10

Effect of the Administration of a Triple Construct, Based on the Fusion of Sushi, IL15 and ApoA1

To study the potential immunostimulant effect of the plasmid pmSushi-mIL15-mApo with the triple construct described in example 1.8., a new test of CD8 lymphocyte proliferation was performed, in a similar way as described in example 5.

To do this, groups of C57BL/6 mice were established (2-3 animals per treatment group), hydrodynamically injected with the plasmid to be tested (2.5 μg/mouse). Six days later, spleens were disintegrated to obtain a unicellular suspension, total cells were counted and after labelling the CD8 T lymphocytes with anti-CD3, anti-CD8 and anti-CD44 antibodies and NK cells with anti-CD3, anti-NK1.1 antibodies, were analysed by multicolour flow cytometry.

The plasmids to be tested in the different treatment groups were:
pmSushi-mIL15-mApo;
pApo-hIL15 in combination with pSushi (pApo-hIL15+pSushi);
pApo-hIL15;
phIL15 in combination with pSushi (phIL15+pSushi);
phIL15; and
pApo.

Figure 10:
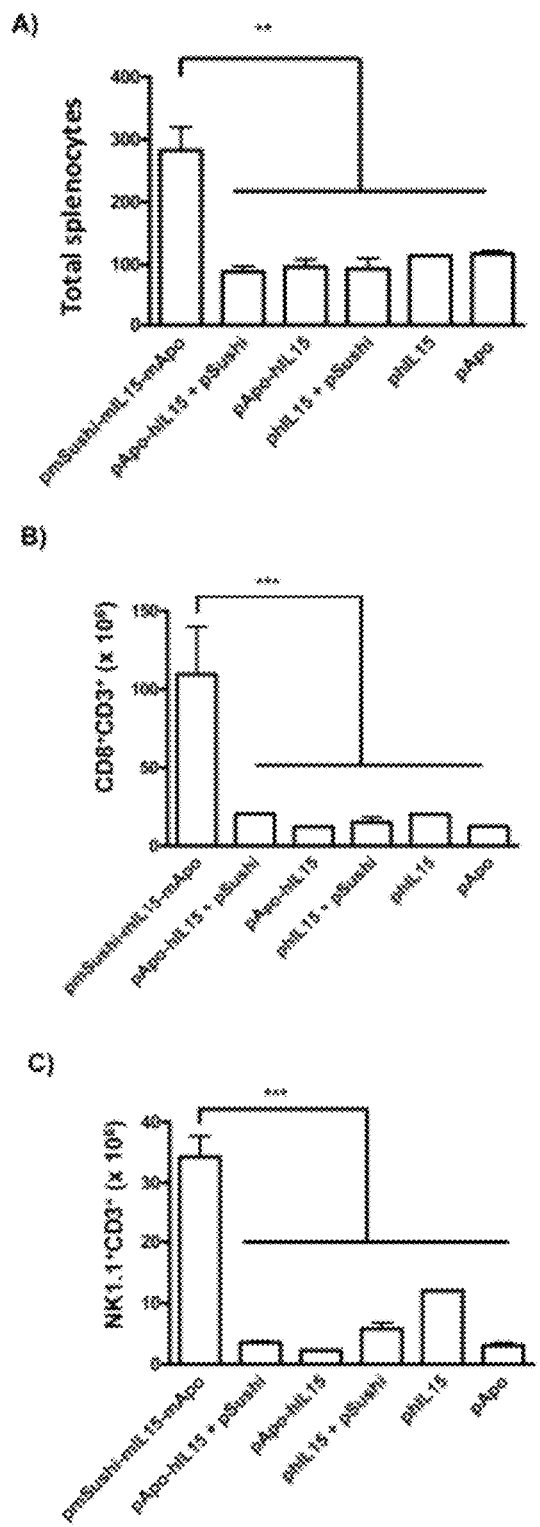
FIG. 10. Increase in the total number of splenocytes and CD8$^+$ T and NK1.1 cells. Groups of C57B16 mice were treated by hydrodynamic injection with plasmids: 1) pmSushi-mIL15-mApo; 2) pApo-hIL15 in combination with pSushi (pApo-hIL15+pSushi); 3) pApo-hIL15; 4) phIL15 in combination with pSushi (phIL15+pSushi); 5) phIL15 and 6) pApo. At 6 days the animals were sacrificed and spleens extracted. A flow cytometry study was made of A) the total splenocyte population; B) CD8$^+$ T memory lymphocytes (CD8$^+$CD3$^+$); and C) NK cells (NK1.1$^+$CD3$^+$). The group of mice administered pmSushi-mIL15-mApo presented a higher number of CD8$^+$ T cells in relation to total splenocytes than the other groups. The mean and mean standard deviation of a representative experiment with 2-3 animals per group is shown. Data were analysed by one-way ANOVA followed by a Bonferroni test comparing the pmSushi-mIL15-mApo group with the rest of the groups injected with plasmids encoding the indicated proteins * p<0.05; * * p<0.001; * * * p<0.0001.

In this test, a notably higher proliferation of the number of spleen cells was observed in the group of animals treated with the pmSushi-mIL15-mApo plasmid, which encodes the triple fusion protein, than in the rest of the treatment groups (FIG. 10A). Similarly, treatment with pmSushi-mIL15-mApo induced a very significantly higher proliferation in the number of CD8 T lymphocytes (FIG. 10B) and NK cells (FIG. 10C) than observed with the other treatments.

Example 11

Effect of the Constructs Encoding for Murine IL15 and for Human IL15 on Stimulating CD8 T and NK Cell Proliferation in Mouse Spleen A comparative study was made of the stimulating activity on the number of splenocytes of the constructs encoding molecules mIL15 and hIL15, by administering the corresponding plasmids by hydrodynamic injection (10 μg/mouse) co-administered or not with the pSushi plasmid. Four days later, spleen were disintegrated to obtain a unicellular suspension, total cells were counted, and after labelling CD8 T lymphocytes with anti-CD3 and anti-CD8 antibodies and NK cells with anti-NK1.1 and anti-CD-3 antibodies, were analysed by multicolour flow cytometry.

Figure 11:
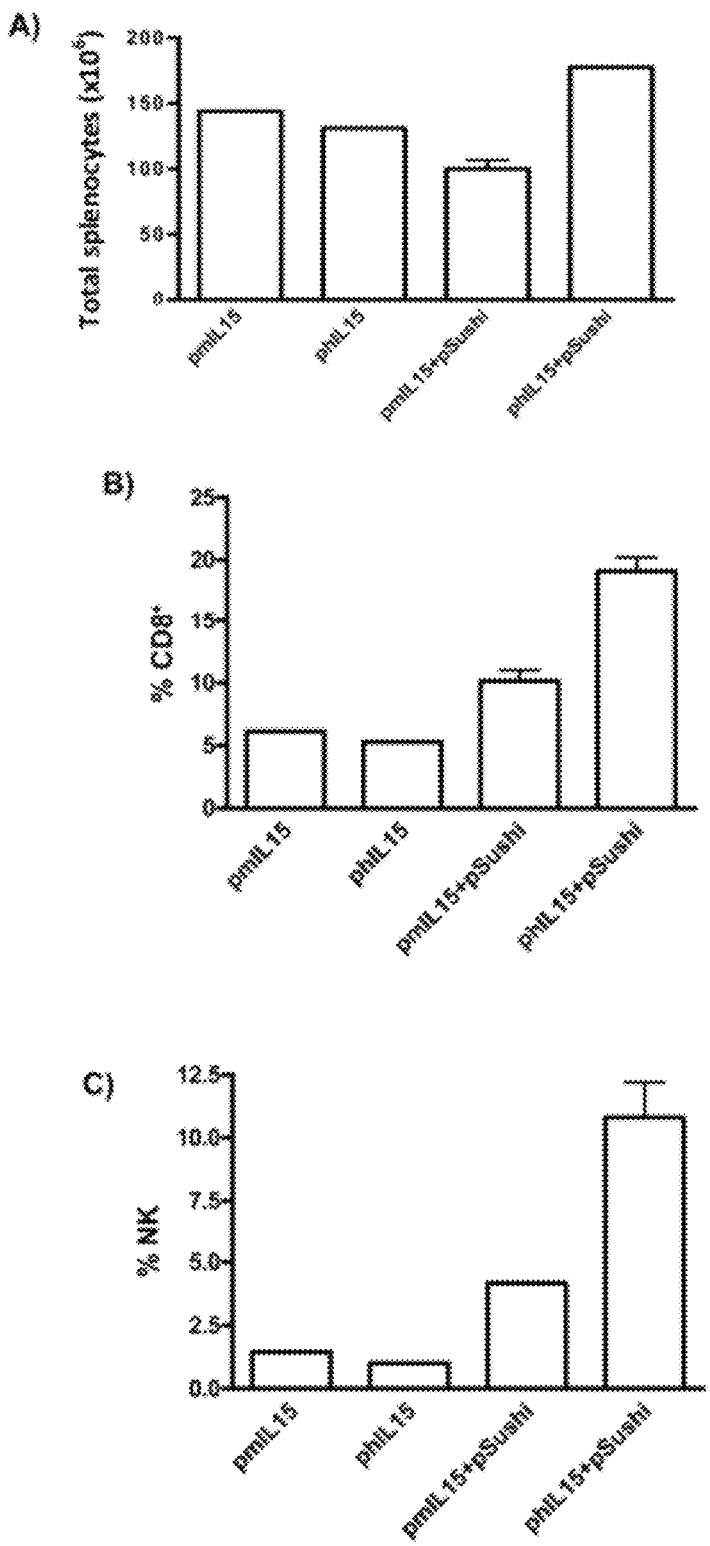
FIG. 11. Comparative effect of the human or murine isoform of IL15 on the increase in total number of splenocytes and the percentage of CD8$^+$ T and NK cells in relation to total splenocytes. Groups of C57BL/6 mice were treated by hydrodynamic injection with plasmids: 1) pmIL15; 2) phIL15; 3) pmIL15 in combination with pSushi; and 4) phIL15 in combination with pSushi. After 4 days animals were sacrificed and the spleens isolated counting total splenocytes (A), CD8 T cells in relation to the total number of splenocytes (B), and NK cells in relation to the total number of splenocytes (C). The mean and mean standard deviation (where applicable) of a representative experiment with 1-2 animals per group is shown. Data were analysed by a Kruskall-Wallis test followed by Dunn's multiple comparison test. The figures show that mIL15 and hIL15 stimulate the number of splenocytes and CD8 T and NK cells in spleen in a similar manner.

Injections of plasmid pmIL15 and plasmid phIL15 induced a similar number of splenocytes, as well as similar percentages of CD8 T and NK cells (FIG. 11). Likewise, when plasmids pmIL15 or phIL15 were co-administered with pSushi, it was observed that the spleen of mice injected with the plasmid encoding the human protein presented a higher percentage of CD8 T and NK cells, although this trend did not prove statistically significant (Kruskall-Wallis test).

Example 12

Effect of the Fusion of mSushi with mIL15 and Apo on the Percentage of NK Cells in Spleen and in Liver Plasmid pmSushi-mIL15-mApo, encoding the triple fusion protein, increases the number of NK cells in spleen and liver to a greater extent than the plasmid pmSushi-mIL15 co-administered with plasmid pApo.

Figure 12:
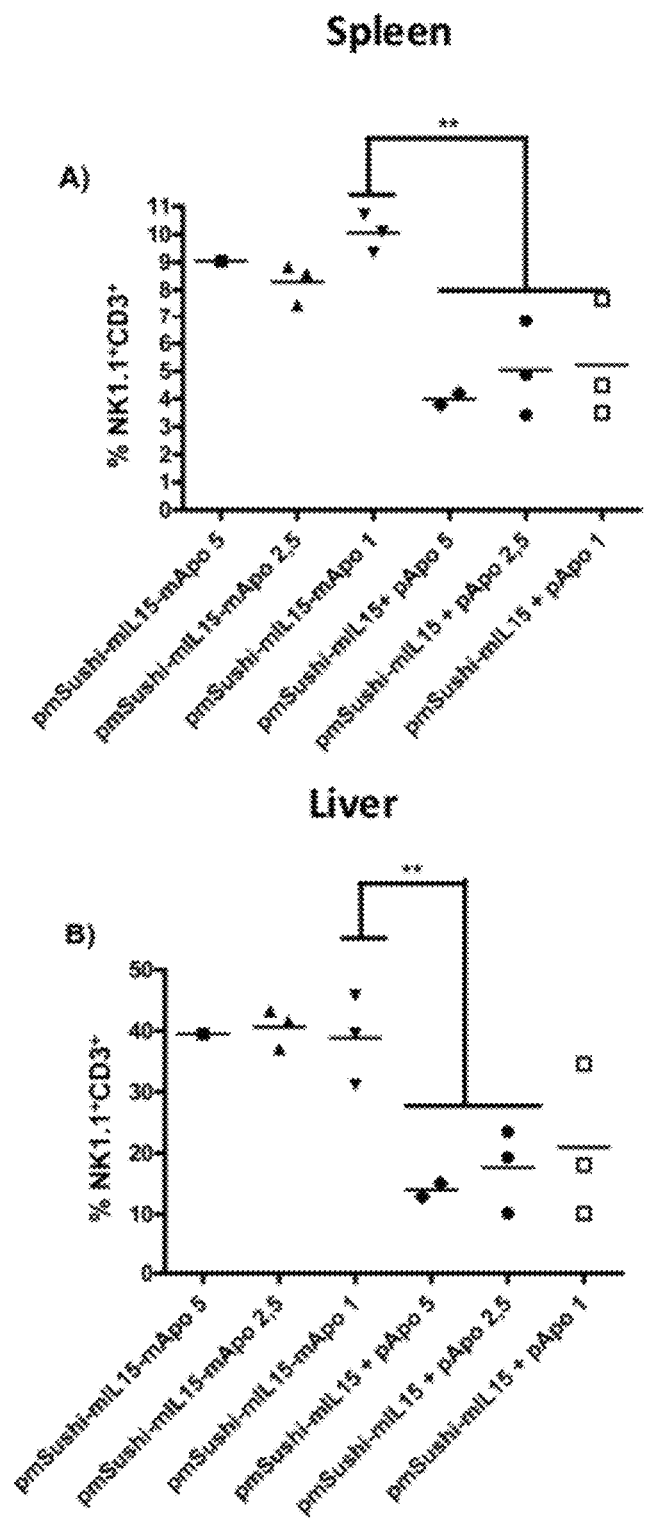
FIG. 12. Effect of the fusion of mSushi with mIL15 and ApoAI on the percentage of NK cells in spleen (A) and in liver (B). Groups of C57BL/6 mice were treated by hydrodynamic injection with plasmids: 1) pmSushi-mIL15-mApo, administered at different doses of 1 μg/mouse, 2.5 μg/mouse, and 5 μg/mouse, respectively; and 2) pmSushi-mIL15 in combination with pApo, both administered at the same 3 doses. After 4 days animals were sacrificed and spleens (A) and livers (B) isolated marking NK cells (NK1.1$^+$CD3$^+$). At all studied doses, the group of mice administered the plasmid pmSushi-mIL5-mApo presented a higher percentage of NK cells than the other groups. Each replicate and the mean of a representative experiment with 2-3 animals per group, is shown. Data were analysed by one-way ANOVA.

Groups of C57BL/6 mice were established, hydrodynamically injected with the plasmid to be tested:
pmSushi-mIL15-mApo, at a dose of 1 μg/mouse;
pmSushi-mIL15-mApo, at a dose of 2.5 μg/mouse;
pmSushi-mIL15-mApo, at a dose of 5 μg/mouse;
pmSushi-mIL15 in combination with pApo, at a dose of 1 μg/mouse;
pmSushi-mIL15 in combination with pApo, at a dose of 2.5 μg/mouse; and
pmSushi-mIL15 in combination with pApo, at a dose of 5 μg/mouse;

Four days later spleens were disintegrated to obtain a unicellular suspension and liver lymphoid cells were isolated by centrifugation with Percoll©. NK cells were labelled with anti-NK1.1 and anti-CD-3 antibodies and were analysed by multicolour flow cytometry. The injection of pmSushi-mIL15-mApo induced the presence of a higher percentage of NK cells in spleen and in liver than the co-administration of pmSushi-mIL15 and pApo (pSushi-mIL-15+pApo) (FIG. 12).

Example 13

Antitumoral Effect of a Triple Construct, Based on the Fusion of Sushi, IL15 and ApoA1 on Subcutaneous MC38 Tumour Model In order to continue studying the antitumoral effect of the pmSushi-mIL15-mApo plasmid with the triple construct described on example 1.8, the subcutaneous tumour model was chosen. C57B16 mice were subcutaneously injected with $5 \times 10^5$ cells of the MC38 line and were treated at 8 and 19 days with the different constructs. The plasmids to be tested in the different treatment groups were:

pApo;
pmSushi-mIL15-mApo;
pApo-hIL15 in combination with pSushi (pApo-hIL15+pSushi);

To do this, groups of C57BL/6 mice carrying tumoral nodules were established: 5 mice were treated with pApo; 8 mice were treated with pmSushi-mIL15-mApo and 9 mice were treated with pApo-hIL15+pSushi by hidrodinamically injecting the plasmid to be tested pApo (1 µg/mouse), pmSushi-mIL15-mApo (1 µg/mouse) and pApo-hIL15+pSushi (10 µg/mouse of each one). Tumour size was measured calculating the product of 2 diameters twice a week with a digital calliper and mice were sacrificed once the size exceeded 246 $mm^2$.

Figure 13:
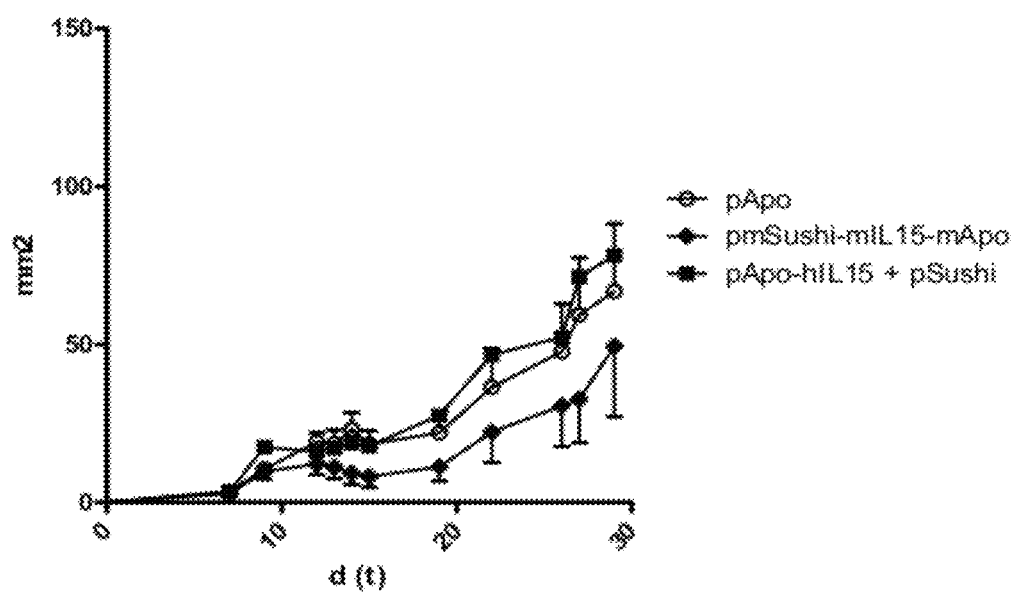
FIG. 13. Antitumoral effect of the fusion of mSushi with mIL15 and ApoAI in the subcutaneous MC38 tumour model. C57B16 mice were administered 5×10$^5$ of MC38 cells subcutaneously and after 8 and 19 days were treated hydrodynamically with plasmids: 1) pApo; 2) pmSushi-mIL15-mApo and 3) pApo-hIL15 in combination with pSushi (pApo-hIL15+pSushi). Tumours were measured in mm$^2$ using a digital calliper every 2-3 days. Mice administered pmSushi-mIL15-mApo were observed to present delayed tumour growth. The mean and standard deviation of a representative experiment with 5-9 animals per group is shown.

Delayed tumour growth was observed in the group of mice treated with pmSushi-mIL15-mApo, which encodes the triple fusion protein, and which was not statistically significant (FIG. 13). 33.3% of mice treated with pmSushi-mIL15-mApo showed no visible tumour at the end of the study (29 days after the inoculation) and only 33.3% of mice showed surface tumours >40 $mm^2$. 20% of mice treated with pApo plasmid showed visible tumour the day of the sacrifice (29 days) and 80% of mice showed a tumour >40 $mm^2$, whereas no mouse treated with pApo-hIL15+pSushi was free of tumours at the end of the study (day 29) and 80% of mice had a tumour >40 $mm^2$ despite having received a dose of separate plasmids 10 times greater than the dose of the triple fusion.

These data indicate that treatment with pmSushi-mIL15-mApo has certain antitumoral effects on the subcutaneous MC38 tumour model.

The invention claimed is:

1. A composition comprising, separately or in the form of a single fusion molecule,
   (i) a first component selected from the group of
      (a) a polypeptide comprising an Apolipoprotein A "Apo A" polypeptide and
      (b) a polynucleotide encoding an Apo A polypeptide and
   (ii) a second component selected from the group of
      (a) Interleukin 15 "IL15" and
      (b) a polynucleotide encoding IL15 and
   (iii) a third component selected from the group of
      (a) the Sushi domain of the IL15 receptor alpha chain and
      (b) a polynucleotide encoding the Sushi domain of the IL15 receptor alpha chain.

2. A composition according to claim 1, wherein the first and second component form part of a single molecule and wherein
   a. if the first and second components are polypeptides, said single molecule is a fusion protein comprising an Apo A polypeptide and IL15 and
   b. if the first and second components are polynucleotides, said single molecule is a polynucleotide encoding a fusion protein comprising a polypeptide comprising an Apo A polypeptide and IL15.

3. A composition according to claim 2, wherein the arrangement of the first and second component of said single molecule is selected from the group consisting of
   c. the first component is located in the N terminal or 5' position in relation to the second component and
   d. the first component is located in the C terminal or 3' position in relation to the second component.

4. A composition according to claim 1, wherein
   the Apo A polypeptide is of human origin or of murine origin,
   the IL15 polypeptide is of human origin or of murine origin and/or
   the Sushi domain of the IL15 receptor alpha chain is of human origin or of murine origin.

5. A pharmaceutical composition comprising a composition according to claim 1 and a pharmaceutically acceptable vehicle.

6. An In vitro method for promoting the expansion of antigen-specific T lymphocytes comprising contacting a population of lymphocytes previously exposed in vivo to said antigen with a composition according to claim 1.

7. The method according to claim 6, wherein the lymphocytes are previously subjected to an in vitro activation by contacting the lymphocytes with the antigen to which the aforesaid T-lymphocytes have been exposed, wherein said activation is carried out prior to said contacting step.

8. A method for increasing the proliferation of CD8 T lymphocytes and/or natural killer (NK) cells in a subject, comprising the administration to said subject of a composition according to claim 1.

9. A composition according to claim 1 comprising, separately or in the form of a single fusion molecule,
   (i) a first component selected from the group of
      (a) a polypeptide comprising an Apo A polypeptide comprising the amino acid sequence set forth in SEQ ID NO: 1, SEQ ID NO: 2 or SEQ ID NO: 3;
      (b) a polynucleotide encoding an Apo A polypeptide wherein the polynucleotide comprises the nucleotide sequence set forth in SEQ ID NO: 4, SEQ ID NO: 5 or SEQ ID NO: 6; and
   (ii) a second component selected from the group of
      (a) IL15 comprising the amino acid sequence set forth in SEQ ID NO: 7, SEQ ID NO:8 or SEQ ID NO: 9;
      (b) a polynucleotide encoding IL15 wherein the polynucleotide comprises the nucleotide sequence set forth in SEQ ID NO: 12, SEQ ID NO: 13 or SEQ ID NO: 14; and
   (iii) a third component selected from the group of
      (a) the Sushi domain of the IL15 receptor alpha chain comprising the amino acid sequence set forth in SEQ ID NO: 17 or SEQ ID NO: 18 and
      (b) a polynucleotide encoding the Sushi domain of the IL15 receptor alpha chain wherein the polynucleotide comprises the nucleotide sequence set forth in SEQ ID NO: 19 or SEQ ID NO: 20.

10. A fusion protein comprising
(i) a region A formed by an Apo A polypeptide,
(ii) a region B formed by IL15 and
(iii) a region C formed by the Sushi domain of the IL15 receptor alpha chain.

11. A fusion protein according to claim 10, wherein the arrangement of regions A, B and C in the direction N-to C-terminal in said fusion protein is selected from the group consisting of A-B-C, A-C-B, B-A-C, B-C-A, C-A-B and C-B-A.

12. A fusion protein according to claim 11, wherein at least one of the bonds between regions A, B and C is established by a peptide linker.

13. A fusion protein according to claim 10, further comprising a peptide linker connecting at least one of the regions A, B and C to at least one neighboring region.

14. A polynucleotide encoding a fusion protein according to claim 10.

15. A vector or a gene construct comprising a polynucleotide according to claim 14.

16. A host cell comprising a fusion protein according to claim 10.

17. A fusion protein according to claim 10, wherein
a. the Apo A polypeptide is of human origin or of murine origin,
b. the IL15 polypeptide is of human origin or of murine origin and/or
c. the Sushi domain of the IL15 receptor alpha chain is of human origin or of murine origin.

18. A pharmaceutical composition comprising a fusion protein according to claim 10 and a pharmaceutically acceptable vehicle.

19. An in vitro method for promoting the expansion of antigen-specific T lymphocytes comprising contacting a population of lymphocytes previously exposed in vivo to said antigen with a fusion protein according to claim 10.

20. The method according to claim 19, wherein the lymphocytes are previously subjected to an in vitro activation by contacting the lymphocytes with the antigen to which the aforesaid T-lymphocytes have been exposed, wherein said activation is carried out prior to said contacting step.

21. A method of increasing survival of a subject suffering from adenocarcinoma, comprising the administration to said subject of a fusion protein according to claim 10.

22. A fusion protein according to claim 10 which comprises the sequence set forth in SEQ ID NO: 42 or SEQ ID NO: 43.

* * * * *

SEQUENCE LISTING

<160> NUMBER OF SEQ ID NOS: 52

<210> SEQ ID NO 1
<211> LENGTH: 267
<212> TYPE: PRT
<213> ORGANISM: Homo sapiens

<400> SEQUENCE: 1

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 2
<211> LENGTH: 264
<212> TYPE: PRT
<213> ORGANISM: Mus musculus

<400> SEQUENCE: 2

Met Lys Ala Val Val Leu Ala Val Ala Leu Val Phe Leu Thr Gly Ser
1               5                   10                  15

Gln Ala Trp His Val Trp Gln Gln Asp Glu Pro Gln Ser Gln Trp Asp
                20                  25                  30

Lys Val Lys Asp Phe Ala Asn Val Tyr Val Asp Ala Val Lys Asp Ser
                35                  40                  45

Gly Arg Asp Tyr Val Ser Gln Phe Glu Ser Ser Ser Leu Gly Gln Gln
            50                  55                  60

Leu Asn Leu Asn Leu Leu Glu Asn Trp Asp Thr Leu Gly Ser Thr Val
65              70                  75                  80

Ser Gln Leu Gln Glu Arg Leu Gly Pro Leu Thr Arg Asp Phe Trp Asp
                85                  90                  95

Asn Leu Glu Lys Glu Thr Asp Trp Val Arg Gln Glu Met Asn Lys Asp
                100                 105                 110

Leu Glu Glu Val Lys Gln Lys Val Gln Pro Tyr Leu Asp Glu Phe Gln
                115                 120                 125

Lys Lys Trp Lys Glu Asp Val Glu Leu Tyr Arg Gln Lys Val Ala Pro
            130                 135                 140

Leu Gly Ala Glu Leu Gln Glu Ser Ala Arg Gln Lys Leu Gln Glu Leu
145                 150                 155                 160

Gln Gly Arg Leu Ser Pro Val Ala Glu Glu Phe Arg Asp Arg Met Arg
                165                 170                 175

Thr His Val Asp Ser Leu Arg Thr Gln Leu Ala Pro His Ser Glu Gln
                180                 185                 190

Met Arg Glu Ser Leu Ala Gln Arg Leu Ala Glu Leu Lys Ser Asn Pro
                195                 200                 205

Thr Leu Asn Glu Tyr His Thr Arg Ala Lys Thr His Leu Lys Thr Leu
            210                 215                 220

Gly Glu Lys Ala Arg Pro Ala Leu Glu Asp Leu Arg His Ser Leu Met
225                 230                 235                 240

Pro Met Leu Glu Thr Leu Lys Thr Lys Ala Gln Ser Val Ile Asp Lys
                245                 250                 255

Ala Ser Glu Thr Leu Thr Ala Gln
            260

<210> SEQ ID NO 3
<211> LENGTH: 259
<212> TYPE: PRT
<213> ORGANISM: Rattus norvegicus

<400> SEQUENCE: 3

Met Lys Ala Ala Val Leu Ala Val Ala Leu Val Phe Leu Thr Gly Cys
1               5                   10                  15

Gln Ala Trp Glu Phe Trp Gln Gln Asp Glu Pro Gln Ser Gln Trp Asp
                20                  25                  30

```
Arg Val Lys Asp Phe Ala Thr Val Tyr Val Asp Ala Val Lys Asp Ser
            35                  40                  45

Gly Arg Asp Tyr Val Ser Gln Phe Glu Ser Ser Thr Leu Gly Lys Gln
 50                  55                  60

Leu Asn Leu Asn Leu Leu Asp Asn Trp Asp Thr Leu Gly Ser Thr Val
 65                  70                  75                  80

Gly Arg Leu Gln Glu Gln Leu Gly Pro Val Thr Gln Glu Phe Trp Ala
                 85                  90                  95

Asn Leu Glu Lys Glu Thr Asp Trp Leu Arg Asn Glu Met Asn Lys Asp
            100                 105                 110

Leu Glu Asn Val Lys Gln Lys Met Gln Pro His Leu Asp Glu Phe Gln
            115                 120                 125

Glu Lys Trp Asn Glu Glu Val Glu Ala Tyr Arg Gln Lys Leu Glu Pro
            130                 135                 140

Leu Gly Thr Glu Leu His Lys Asn Ala Lys Glu Met Gln Arg His Leu
145                 150                 155                 160

Lys Val Val Ala Glu Glu Phe Arg Asp Arg Met Arg Val Asn Ala Asp
                165                 170                 175

Ala Leu Arg Ala Lys Phe Gly Leu Tyr Ser Asp Gln Met Arg Glu Asn
            180                 185                 190

Leu Ala Gln Arg Leu Thr Glu Ile Lys Asn His Pro Thr Leu Ile Glu
            195                 200                 205

Tyr His Thr Lys Ala Ser Asp His Leu Lys Thr Leu Gly Glu Lys Ala
            210                 215                 220

Lys Pro Ala Leu Asp Asp Leu Gly Gln Gly Leu Met Pro Val Leu Glu
225                 230                 235                 240

Ala Trp Lys Ala Lys Ile Met Ser Met Ile Asp Glu Ala Lys Lys Lys
                245                 250                 255

Leu Asn Ala

<210> SEQ ID NO 4
<211> LENGTH: 965
<212> TYPE: DNA
<213> ORGANISM: Homo sapiens

<400> SEQUENCE: 4
gaattcaaaa aaaaagaaa aaaaaaaaa aaaaaaaaaa aaaaaagag agactgcgag      60 aaggaggtcc cccacggccc ttcaggatga agctgcggt gctgaccttg gccgtgctct    120
tcctgacggg gagccaggct cggcatttct ggcagcaaga tgaaccccc cagagccct    180 gggatcgagt gaaggacctg ccactgtgt acgtggatgt gctcaaagac agcggcagag   240
actatgtgtc ccagtttgaa ggctccgcct tgggaaaaca gctaaaccta agctccttg   300 acaactggga cagcgtgacc tccaccttca gcaagctgcg cgaacagctc ggccctgtga   360
cccaggagtt ctgggataac ctggaaaagg agacagaggg cctgaggcag agatgagca   420 aggatctgga ggaggtgaag gccaaggtgc agccctacct ggacgacttc cagaagaagt   480
ggcaggagga gatggagctc taccgccaga aggtggagcc gctgcgcgca gagctccaag   540
agggcgcgcg ccagaagctg cacgagctgc aagagaagct gagcccactg ggcgaggaga   600
tgcgcgaccg cgcgcgcgcc catgtggacg cgctgcgcac gcatctggcc cctacagcg    660 acgagctgcg ccagcgcttg gccgcgcgcc ttgaggctct caaggagaac ggcggcgcca   720
gactggccga gtaccacgcc aaggccaccg agcatctgag cacgctcagc gagaaggcca   780
agcccgcgct cgaggacctc cgccaaggcc tgctgccccgt gctggagagc ttcaaggtca   840
```

```
gcttcctgag cgctctcgag gagtacacta agaagctcaa cacccagtga ggcgcccgcc    900
gccgcccccc ttcccggtgc tcagaataaa cgtttccaaa gtgggaaaaa aaaaaaaaag    960
aattc                                                                965

<210> SEQ ID NO 5
<211> LENGTH: 924
<212> TYPE: DNA
<213> ORGANISM: Mus musculus

<400> SEQUENCE: 5
accccagact gtcggagagc tccggggagg tcacccacac ccttcaggat gaaagctgtg     60
gtgctggccg tggctctggt cttcctgaca gggagccagg cttggcacgt atggcagcaa    120
gatgaacccc agtcccaatg gacaaagtg aaggatttcg ctaatgtgta tgtggatgcg     180
gtcaaagaca gcggcagaga ctatgtgtcc cagtttgaat cctcctcctt gggccaacag    240
ctgaacctga atctcctgga aaactgggac actctgggtt caaccgttag tcagctgcag    300
gaacggctgg gcccattgac tcgggacttc tgggataacc tggagaaaga aacagattgg    360
gtgagacagg agatgaacaa ggacctagag gaagtgaaac agaaggtgca gccctacctg    420
gacgaattcc agaagaaatg gaaagaggat gtggagctct accgccagaa ggtggcgcct    480
ctgggcgccg agctgcagga gagcgcgcgc cagaagctgc aggagctgca agggagactg    540
tcccctgtgg ctgaggaatt cgcgaccgc atgcgcacac acgtagactc tctgcgcaca    600
cagctagcgc cccacagcga acagatgcgc gagagcctgg cccagcgcct ggctgagctc    660
aagagcaacc ctaccttgaa cgagtaccac accagggcca aacccaccct gaagacactt    720
ggcgagaaag ccagacctgc gctggaggac ctgcgccata gtctgatgcc catgctggag    780
acgcttaaga ccaaagccca gagtgtgatc gacaaggcca gcgagactct gactgcccag    840
tgaggtgccc gcttccactc cccaccccg cattggcttt cttacaataa ccttttccaa    900
aatggaaaaa aaaaaaaaaa aaaa                                           924

<210> SEQ ID NO 6
<211> LENGTH: 889
<212> TYPE: DNA
<213> ORGANISM: Rattus norvegicus

<400> SEQUENCE: 6
agactgttgg agagctccgg gggaggtcgc cacatccttc aggatgaaag ctgcagtgtt     60
ggctgtggcc ctggtcttcc tgacaggttg ccaagcttgg agttctggc agcaagatga    120 gccccagtcc caatgggaca gggtgaagga tttcgccact gtgtatgtgg atgcagtcaa    180
ggacagcggc agagactatg tgtcccagtt tgaatcctcc actttgggca acagctgaa    240 cctgaatctc ctggacaact gggacactct gggttcaact gttggtcgcc tacaggaaca    300
gctaggccca gtgactcagg agttctggc taacctggag aaagaaacag attggctgag    360
aaacgagatg aacaaggacc tggagaatgt gaaacagaag atgcagcccc acctggatga    420
attccaggag aagtggaacg aggaggtcga ggcctaccgc cagaagctgg agcctctggg    480
caccgagctt cacaaaaacg cgaaggagat gcaaaggcat ctaaaggttg tggccgagga    540
gtttcgagac cgcatgcgtg tgaatgcaga cgcgctgcgc gcaaagtttg ggctctacag    600
cgatcagatg cgcgagaacc tggcccagcg cctgaccgag atcaagaacc ccctacccct    660
gatcgagtat cataccaagg ccagcgacca cctgaagaca cttggtgaga agccaaacc    720
```

```
cgcgctggat gacctgggcc agggcctgat gccggtgctg gaagcctgga aggccaaaat    780
catgagtatg atcgatgagg ccaaaaagaa gctgaacgct tagtgaggcg cccgtcacca    840
ctccccaccc ctgaattggc tttcttacaa taaacgtttc caaagtggg              889
```

<210> SEQ ID NO 7
<211> LENGTH: 162
<212> TYPE: PRT
<213> ORGANISM: Homo sapiens

<400> SEQUENCE: 7

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 8
<211> LENGTH: 162
<212> TYPE: PRT
<213> ORGANISM: Mus musculus

<400> SEQUENCE: 8

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
```

```
                130                 135                 140
Thr Glu Phe Leu Gln Ser Phe Ile Arg Ile Val Gln Met Phe Ile Asn
145                 150                 155                 160

Thr Ser

<210> SEQ ID NO 9
<211> LENGTH: 162
<212> TYPE: PRT
<213> ORGANISM: Rattus norvegicus

<400> SEQUENCE: 9

Met Lys Ile Leu Lys Pro Tyr Met Arg Asn Thr Ser Ile Leu Tyr Tyr
1               5                   10                  15

Leu Cys Phe Leu Leu Asn Ser His Phe Leu Thr Glu Ala Gly Ile His
                20                  25                  30

Val Phe Ile Leu Gly Cys Val Ser Val Gly Leu Pro Lys Thr Glu Ala
            35                  40                  45

Asn Trp Ile Asp Val Arg Tyr Asp Leu Glu Lys Ile Glu Ser Leu Ile
        50                  55                  60

Gln Phe Ile His Ile Asp Thr Thr Leu Tyr Thr Asp Ser Asp Phe His
65                  70                  75                  80

Pro Ser Cys Lys Val Thr Ala Met Asn Cys Phe Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ile Glu Ser Gly Cys Lys Glu Cys Glu Glu Leu Glu Glu Arg Asn Phe
    130                 135                 140

Thr Glu Phe Leu Gln Ser Phe Ile His Ile Val Gln Met Phe Ile Asn
145                 150                 155                 160

Thr Ser

<210> SEQ ID NO 10
<211> LENGTH: 162
<212> TYPE: PRT
<213> ORGANISM: Felis catus

<400> SEQUENCE: 10

Met Arg Ile Leu Lys Pro Tyr Leu Arg Ser Thr Ser Ile Gln Cys Tyr
1               5                   10                  15

Leu Cys Leu Leu Leu Asn Ser His Phe Leu Thr Glu Ala Cys Ile Pro
                20                  25                  30

Val Phe Ile Leu Ser Cys Ile Asn Ala Gly Leu Pro Lys Thr Glu Ala
            35                  40                  45

Asn Trp Gln Asp Val Ile Ser Asp Leu Lys Ile Ile Asp Lys Ile Ile
        50                  55                  60

Gln Ser Leu His Ile Asp Ala Thr Leu Tyr Thr Glu Ser Asp Val His
65                  70                  75                  80

Pro Asn Cys Lys Val Thr Ala Met Lys Cys Phe Leu Leu Glu Leu His
                85                  90                  95

Val Ile Ser Leu Glu Ser Lys Asn Glu Thr Ile His Gln Thr Val Glu
            100                 105                 110

Asn Ile Ile Ile Leu Ala Asn Ser Gly Leu Ser Ser Asn Arg Asn Ile
        115                 120                 125
```

```
Thr Glu Thr Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser

<210> SEQ ID NO 11
<211> LENGTH: 162
<212> TYPE: PRT
<213> ORGANISM: Bos taurus

<400> SEQUENCE: 11

Met Arg Ile Leu Lys Pro Tyr Leu Arg Ser Thr Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Ile Ser Ala Ser Leu Pro Lys Thr Glu Ala
        35                  40                  45

Asn Trp Gln Tyr Val Ile Asn Asp Leu Lys Thr Ile Glu His Leu Ile
    50                  55                  60

Gln Ser Ile His Met Asp Ala Thr Leu Tyr Thr Glu Ser Asp Ala His
65                  70                  75                  80

Pro Asn Cys Lys Val Thr Ala Met Gln Cys Phe Leu Leu Glu Leu Arg
                85                  90                  95

Val Ile Leu His Glu Ser Lys Asn Ala Thr Ile Tyr Glu Ile Ile Glu
            100                 105                 110

Asn Leu Thr Met Leu Ala Asn Ser Asn Leu Ser Ser Ile Glu Asn Lys
        115                 120                 125

Thr Glu Leu Gly Cys Lys Glu Cys Glu Glu Leu Glu Glu Lys Ser Ile
    130                 135                 140

Lys Glu Phe Leu Lys Ser Phe Val His Ile Val Gln Met Phe Ile Asn
145                 150                 155                 160

Thr Ser

<210> SEQ ID NO 12
<211> LENGTH: 411
<212> TYPE: DNA
<213> ORGANISM: Artificial
<220> FEATURE:
<223> OTHER INFORMATION: Sequence encoding a polypeptide comprising
      human IL15
<220> FEATURE:
<221> NAME/KEY: misc_feature
<222> LOCATION: (1)..(66)
<223> OTHER INFORMATION: Secuence encoding the signal peptide of IgV-ji
      chain
<220> FEATURE:
<221> NAME/KEY: mis_feature
<222> LOCATION: (67)..(411)
<223> OTHER INFORMATION: Secuence encoding mature human IL15
      (NM_172174.2 REGION: 990..1331)

<400> SEQUENCE: 12
atggattttc aggtgcagat tttcagcttc ctgctaatca gtgcctcagt cataatgtct      60
agagccaact gggtgaatgt aataagtgat ttgaaaaaaa ttgaagatct tattcaatct     120
atgcatattg atgctacttt atatacggaa agtgatgttc accccagttg caaagtaaca     180
gcaatgaagt gctttctctt ggagttacaa gttatttcac ttgagtccgg agatgcaagt     240
attcatgata cagtagaaaa tctgatcatc ctagcaaaca acagtttgtc ttctaatggg     300
```

```
aatgtaacag aatctggatg caaagaatgt gaggaactgg aggaaaaaaa tattaaagaa    360
ttttttgcaga gttttgtaca tattgtccaa atgttcatca acacttcttg a           411
```

<210> SEQ ID NO 13
<211> LENGTH: 489
<212> TYPE: DNA
<213> ORGANISM: Mus musculus

<400> SEQUENCE: 13

```
atgaaaattt tgaaaccata tatgaggaat acatccatct cgtgctactt gtgtttcctt    60
ctaaacagtc acttttttaac tgaggctggc attcatgtct tcattttggg ctgtgtcagt  120
gtaggtctcc ctaaaacaga ggccaactgg atagatgtaa gatatgacct ggagaaaatt  180
gaaagcctta ttcaatctat tcatattgac accactttat acactgacag tgactttcat  240
cccagttgca aagttactgc aatgaactgc tttctcctgg aattgcaggt tattttacat  300
gagtacagta acatgactct taatgaaaca gtaagaaacg tgctctacct tgcaaacagc  360
actctgtctt ctaacaagaa tgtagcagaa tctggctgca aggaatgtga ggagctggag  420
gagaaaacct tcacagagtt tttgcaaagc tttatacgca ttgtccaaat gttcatcaac  480
acgtcctga                                                          489
```

<210> SEQ ID NO 14
<211> LENGTH: 489
<212> TYPE: DNA
<213> ORGANISM: Rattus norvegicus

<400> SEQUENCE: 14

```
atgaaaattt tgaaaccata tatgaggaat acatccatct tgtactacct gtgtttcctt    60
ctcaacagtc acttcttaac tgaggctggc atccatgtct tcattttggg ctgtgtcagt  120
gtaggtctcc ctaaaacaga ggccaactgg atagatgtaa gatacgatct ggagaaaatt  180
gaaagtctta ttcaatttat tcatattgat actactctat acactgacag tgactttcat  240
cccagttgca aagttactgc aatgaactgc tttctcctgg aattacaggt tattttgcac  300
gagtacagta acatgactct taatgaaaca gtaagaaacg tgctctacct tgcaaacagc  360
actctgtctt ctaacaagaa tgtaatagag tctggctgca aggaatgtga ggagctggag  420
gagagaaact tcacggagtt tttgcagagt tttatacata ttgtccaaat gttcatcaac  480
acgtcctga                                                          489
```

<210> SEQ ID NO 15
<211> LENGTH: 489
<212> TYPE: DNA
<213> ORGANISM: Felis catus

<400> SEQUENCE: 15

```
atgagaattt tgaaaccata tttgagaagt acttccatcc agtgctactt gtgtttactt    60
ctgaacagcc attttttaac tgaagcttgc attcctgttt cattttgag ctgtattaat   120
gcaggtcttc ctaaaacaga ggcaaactgg caggatgtaa taagtgattt gaaaataatt  180
gacaagatta ttcaatcctt acatatcgat gccactttat atactgaaag tgatgttcat  240
cccaattgca aagtaacagc gatgaagtgc tttctcctgg agttacatgt tatttcgctt  300
gagtccaaaa atgagaccat tcatcaaaca gtagaaaaca ttattatcct ggcaaacagt  360
ggtttatctt ctaacaggaa tataactgaa acaggatgca aagaatgtga ggaactggag  420
gaaaagaaca ttaaagaatt tctgcagagt tttgtacata ttgtacaaat gttcatcaac  480
```

```
acttcttga                                                           489

<210> SEQ ID NO 16
<211> LENGTH: 489
<212> TYPE: DNA
<213> ORGANISM: Bos taurus

<400> SEQUENCE: 16
atgagaattt tgaaaccata tttgagaagt acttccatcc agtgctactt gtgtttactt       60
ctgaacagtc attttttaac agaggctggc attcatgtct tcattttggg ctgtatcagt      120
gcaagtcttc ccaaaacaga agcaaactgg cagtatgtaa taaatgattt gaaaacaatt      180
gagcatctta ttcaatctat acatatggat gccactttat atactgaaag tgatgctcat      240
cccaattgca agtaacagc gatgcagtgc tttctcctgg agttacgagt tattttacac       300
gagtccaaaa atgccaccat ttatgaaata atagaaaatc ttaccatgct agcaaacagc      360
aatttatctt ctattgagaa taaaacagaa tgggatgca aagaatgtga ggaactggag       420
gaaaaaagta tcaaagaatt tttgaagagt tttgtacata ttgtgcaaat gttcatcaac      480
acttcttga                                                           489

<210> SEQ ID NO 17
<211> LENGTH: 61
<212> TYPE: PRT
<213> ORGANISM: Homo sapiens

<400> SEQUENCE: 17

Cys Pro Pro Pro Met Ser Val Glu His Ala Asp Ile Trp Val Lys Ser
1               5                  10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
    50                  55                  60

<210> SEQ ID NO 18
<211> LENGTH: 61
<212> TYPE: PRT
<213> ORGANISM: Mus musculus

<400> SEQUENCE: 18

Cys Pro Pro Pro Val Ser Ile Glu His Ala Asp Ile Arg Val Lys Asn
1               5                  10                  15

Tyr Ser Val Asn Ser Arg Glu Arg Tyr Val Cys Asn Ser Gly Phe Lys
            20                  25                  30

Arg Lys Ala Gly Thr Ser Thr Leu Ile Glu Cys Val Ile Asn Lys Asn
        35                  40                  45

Thr Asn Val Ala His Trp Thr Thr Pro Ser Leu Lys Cys
    50                  55                  60

<210> SEQ ID NO 19
<211> LENGTH: 291
<212> TYPE: DNA
<213> ORGANISM: Artificial
<220> FEATURE:
<223> OTHER INFORMATION: Sequence encoding a polypeptide comprising the
      Sushi domain of the human IL15 receptor alpha subunit (IL15RA)
<220> FEATURE:
<221> NAME/KEY: misc_feature
```

```
<222> LOCATION: (1)..(288)
<223> OTHER INFORMATION: Secuence encoding the signal peptide and Sushi
      domain of the human IL15 receptor alpha subunit (IL15RA)
      (NM_002189.2 REGION: 83 ..371)

<400> SEQUENCE: 19
atggccccgc ggcgggcgcg cggctgccgg accctcggtc tcccggcgct gctactgctg     60
ctgctgctcc ggccgccggc gacgcggggc atcacgtgcc ctcccccat gtccgtggaa    120 cacgcagaca tctgggtcaa gagctacagc ttgtactcca gggagcggta catttgtaac    180
tctggtttca gcgtaaagc cggcacgtcc agcctgacgg agtgcgtgtt gaacaaggcc    240
acgaatgtcg cccactggac aaccccagt ctcaaatgca ttagagactg a             291

<210> SEQ ID NO 20
<211> LENGTH: 273
<212> TYPE: DNA
<213> ORGANISM: Artificial
<220> FEATURE:
<223> OTHER INFORMATION: Sequence encoding a polypeptide comprising the
      Sushi domain of murine IL15alpha receptor (Il15ra)
<220> FEATURE:
<221> NAME/KEY: misc_features
<222> LOCATION: (1)..(64)
<223> OTHER INFORMATION: Sequence encoding a Ig-kappa signal peptide
<220> FEATURE:
<221> NAME/KEY: misc_features
<222> LOCATION: (65)..(273)
<223> OTHER INFORMATION: Sequence encoding the Sushi domain of murine
      IL15 receptor alpha subunit (Il15ra)

<400> SEQUENCE: 20
atggagacag acaccctgct gctctgggtg ctgctgctgt gggtgcccgg ctctaccggc     60
gacggcacca cctgcccctcc ccctgtgtcc atcgagcacg ccgacatcag agtgaagaac    120
tactccgtga actctcggga gagatacgtg tgcaactccg gcttcaagcg gaaggccggc    180
acctccaccc tgatcgagtg cgtgatcaac aagaacacca acgtggccca ctggaccacc    240
ccttccctga agtgcatccg ggacccttcc tga                                 273

<210> SEQ ID NO 21
<211> LENGTH: 279
<212> TYPE: DNA
<213> ORGANISM: Homo sapiens

<400> SEQUENCE: 21
atggccccgc ggcgggcgcg cggctgccgg accctcggtc tcccggcgct gctactgctg     60
ctgctgctcc ggccgccggc gacgcggggc atcacgtgcc ctcccccat gtccgtggaa    120 cacgcagaca tctgggtcaa gagctacagc ttgtactcca gggagcggta catttgtaac    180
tctggtttca gcgtaaagc cggcacgtcc agcctgacgg agtgcgtgtt gaacaaggcc    240
acgaatgtcg cccactggac aaccccagt ctcaaatgc                            279

<210> SEQ ID NO 22
<211> LENGTH: 93
<212> TYPE: PRT
<213> ORGANISM: Homo sapiens

<400> SEQUENCE: 22

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30
```

Cys Pro Pro Met Ser Val Glu His Ala Asp Ile Trp Val Lys Ser
              35                  40                  45

Tyr Ser Leu Tyr Ser Arg Glu Arg Tyr Ile Cys Asn Ser Gly Phe Lys
 50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys
                 85                  90

<210> SEQ ID NO 23
<211> LENGTH: 14
<212> TYPE: PRT
<213> ORGANISM: Artificial
<220> FEATURE:
<223> OTHER INFORMATION: Linker

<400> SEQUENCE: 23

Ser Gly Gly Thr Ser Gly Ser Thr Ser Gly Thr Gly Ser Thr
1               5                   10

<210> SEQ ID NO 24
<211> LENGTH: 15
<212> TYPE: PRT
<213> ORGANISM: Artificial
<220> FEATURE:
<223> OTHER INFORMATION: Linker

<400> SEQUENCE: 24

Ala Gly Ser Ser Thr Gly Ser Ser Thr Gly Pro Gly Ser Thr Thr
1               5                   10                  15

<210> SEQ ID NO 25
<211> LENGTH: 7
<212> TYPE: PRT
<213> ORGANISM: Artificial
<220> FEATURE:
<223> OTHER INFORMATION: Linker

<400> SEQUENCE: 25

Gly Gly Ser Gly Gly Ala Pro
1               5

<210> SEQ ID NO 26
<211> LENGTH: 8
<212> TYPE: PRT
<213> ORGANISM: Artificial
<220> FEATURE:
<223> OTHER INFORMATION: Linker

<400> SEQUENCE: 26

Gly Gly Gly Val Glu Gly Gly Gly
1               5

<210> SEQ ID NO 27
<211> LENGTH: 7
<212> TYPE: PRT
<213> ORGANISM: Artificial
<220> FEATURE:
<223> OTHER INFORMATION: Linker

<400> SEQUENCE: 27

Gly Thr Lys Val His Met Lys
1               5

<210> SEQ ID NO 28

```
<211> LENGTH: 13
<212> TYPE: PRT
<213> ORGANISM: Artificial
<220> FEATURE:
<223> OTHER INFORMATION: Linker

<400> SEQUENCE: 28

Pro Gly Thr Ser Gly Gln Gln Pro Ser Val Gly Gln Gln
1               5                   10

<210> SEQ ID NO 29
<211> LENGTH: 5
<212> TYPE: PRT
<213> ORGANISM: Artificial
<220> FEATURE:
<223> OTHER INFORMATION: Linker

<400> SEQUENCE: 29

Gly Thr Ser Gly Gln
1               5

<210> SEQ ID NO 30
<211> LENGTH: 10
<212> TYPE: PRT
<213> ORGANISM: Artificial
<220> FEATURE:
<223> OTHER INFORMATION: Linker

<400> SEQUENCE: 30

Pro Lys Pro Ser Thr Pro Pro Gly Ser Ser
1               5                   10

<210> SEQ ID NO 31
<211> LENGTH: 11
<212> TYPE: PRT
<213> ORGANISM: Artificial
<220> FEATURE:
<223> OTHER INFORMATION: Linker

<400> SEQUENCE: 31

Ala Pro Ala Glu Thr Lys Ala Glu Pro Met Thr
1               5                   10

<210> SEQ ID NO 32
<211> LENGTH: 19
<212> TYPE: PRT
<213> ORGANISM: Artificial
<220> FEATURE:
<223> OTHER INFORMATION: Linker

<400> SEQUENCE: 32

Gly Gly Ser Gly Gly Gly Gly Ser Gly Gly Gly Ser Gly Gly Gly Gly
1               5                   10                  15

Ser Leu Gln

<210> SEQ ID NO 33
<211> LENGTH: 5
<212> TYPE: PRT
<213> ORGANISM: Artificial
<220> FEATURE:
<223> OTHER INFORMATION: Enterokinase cleavage site

<400> SEQUENCE: 33

Asp Asp Asp Asp Lys
1               5
```

-continued

```
<210> SEQ ID NO 34
<211> LENGTH: 5
<212> TYPE: PRT
<213> ORGANISM: Artificial
<220> FEATURE:
<223> OTHER INFORMATION: Factor Xa cleavage site

<400> SEQUENCE: 34

Ile Glu Asp Gly Arg
1               5

<210> SEQ ID NO 35
<211> LENGTH: 6
<212> TYPE: PRT
<213> ORGANISM: Artificial
<220> FEATURE:
<223> OTHER INFORMATION: Thrombin cleavage site

<400> SEQUENCE: 35

Leu Val Pro Arg Gly Ser
1               5

<210> SEQ ID NO 36
<211> LENGTH: 7
<212> TYPE: PRT
<213> ORGANISM: Artificial
<220> FEATURE:
<223> OTHER INFORMATION: TEV protease cleavage site

<400> SEQUENCE: 36

Glu Asn Leu Tyr Phe Gln Gly
1               5

<210> SEQ ID NO 37
<211> LENGTH: 8
<212> TYPE: PRT
<213> ORGANISM: Artificial
<220> FEATURE:
<223> OTHER INFORMATION: PreScission protease cleavage site

<400> SEQUENCE: 37

Leu Glu Val Leu Phe Gln Gly Pro
1               5

<210> SEQ ID NO 38
<211> LENGTH: 5
<212> TYPE: PRT
<213> ORGANISM: Artificial
<220> FEATURE:
<223> OTHER INFORMATION: MMP9 cleavage site

<400> SEQUENCE: 38

Leu Phe Pro Thr Ser
1               5

<210> SEQ ID NO 39
<211> LENGTH: 1155
<212> TYPE: DNA
<213> ORGANISM: Artificial
<220> FEATURE:
<223> OTHER INFORMATION: Sequence encoding hApo-hIL15 fusion protein
<220> FEATURE:
<221> NAME/KEY: misc_feature
<222> LOCATION: (1)..(801)
<223> OTHER INFORMATION: Sequence encoding human apolipoprotein A-I
      (APOA1) (NM_000039.1 REGION: 39..839)
<220> FEATURE:
<221> NAME/KEY: misc_feature
<222> LOCATION: (802)..(810)
```

```
<223> OTHER INFORMATION: Sequence encoding GAP linker
<220> FEATURE:
<221> NAME/KEY: misc_feature
<222> LOCATION: (811)..(1153)
<223> OTHER INFORMATION: Sequence encoding mature human IL15
      (NM_172174.2 REGION: 990..1331)

<400> SEQUENCE: 39
```

| | | |
|---|---|---|
| atgaaagctg cggtgctgac cttggccgtg ctcttcctga cggggagcca ggctcggcat | 60 |
| ttctggcagc aagatgaacc ccccagagc ccctgggatc gagtgaagga cctgccact | 120 |
| gtgtacgtgg atgtgctcaa agacagcggc agagactatg tgtcccagtt tgaaggctcc | 180 |
| gccttgggaa acagctaaa cctaaagctc cttgacaact gggacagcgt gacctccacc | 240 |
| ttcagcaagc tgcgcgaaca gctcggccct gtgacccagg agttctggga taacctggaa | 300 |
| aaggagacag agggcctgag gcaggagatg agcaaggatc tggaggaggt gaaggccaag | 360 |
| gtgcagccct acctggacga cttccagaag aagtggcagg aggagatgga gctctaccgc | 420 |
| cagaaggtgg agccgctgcg cgcagagctc aagagggcg cgcgccagaa gctgcacgag | 480 |
| ctgcaagaga agctgagccc actgggcgag gagatgcgcg accgcgcgcg cgcccatgtg | 540 |
| gacgcgctgc gcacgcatct ggcccccta cagcgacgag tgcgccagcg cttggccgcg | 600 |
| cgccttgagg ctctcaagga aacggcggc gccagactgg ccgagtacca cgccaaggcc | 660 |
| accgagcatc tgagcacgct cagcgagaag gccaagcccg cgctcgagga cctccgccaa | 720 |
| ggcctgctgc ccgtgctgga gagcttcaag gtcagcttcc tgagcgctct cgaggagtac | 780 |
| actaagaagc tcaacaccca gggcgcgccc aactgggtga atgtaataag tgatttgaaa | 840 |
| aaaattgaag atcttattca atctatgcat attgatgcta ctttatatac ggaaagtgat | 900 |
| gttcaccccca gttgcaaagt aacagcaatg aagtgctttc tcttggagtt acaagttatt | 960 |
| tcacttgagt ccggagatgc aagtattcat gatacagtag aaaatctgat catcctagca | 1020 |
| aacaacagtt tgtcttctaa tgggaatgta acagaatctg gatgcaaaga atgtgaggaa | 1080 |
| ctggaggaaa aaaatattaa agaatttttg cagagttttg tacatattgt ccaaatgttc | 1140 |
| atcaacactt cttga | 1155 |

```
<210> SEQ ID NO 40
<211> LENGTH: 1146
<212> TYPE: DNA
<213> ORGANISM: Artificial
<220> FEATURE:
<223> OTHER INFORMATION: Sequence encoding a mApo-hIL15 fusion protein
<220> FEATURE:
<221> NAME/KEY: misc_feature
<222> LOCATION: (1)..(792)
<223> OTHER INFORMATION: Sequence encoding murine apolipoprotein A-I
      (Apoa1) (NM_009692.2 REGION: 47 .. 838)
<220> FEATURE:
<221> NAME/KEY: misc_feature
<222> LOCATION: (793)..(800)
<223> OTHER INFORMATION: Sequence encoding GAP linker
<220> FEATURE:
<221> NAME/KEY: misc_feature
<222> LOCATION: (801)..(1143)
<223> OTHER INFORMATION: Sequence encoding mature human IL15
      (NM_172174.2 REGION: 990..1331)

<400> SEQUENCE: 40
```

| | |
|---|---|
| atgaaagctg tggtgctggc cgtggctctg gtcttcctga cagggagcca ggcttggcac | 60 |
| gtatggcagc aagatgaacc ccagtcccaa tgggacaaag tgaaggattt cgctaatgtg | 120 |
| tatgtggatg cggtcaaaga cagcggcaga gactatgtgt cccagtttga atcctcctcc | 180 |

-continued
ttgggccaac agctgaacct gaatctcctg gaaaactggg acactctggg ttcaaccgtt 240
agtcagctgc aggaacggct gggcccattg actcgggact tctgggataa cctggagaaa 300
gaaacagatt gggtgagaca ggagatgaac aaggacctag aggaagtgaa acagaaggtg 360
cagccctacc tggacgaatt ccagaagaaa tggaaagagg atgtggagct ctaccgccag 420
aaggtggcgc ctctgggcgc cgagctgcag gagagcgcgc gccagaagct gcaggagctg 480
caagggagac tgtcccctgt ggctgaggaa tttcgcgacc gcatgcgcac acacgtagac 540
tctctgcgca cacagctagc gccccacagc gaacagatgc gcgagagcct ggcccagcgc 600
ctggctgagc tcaagagcaa ccctaccttg aacgagtacc acaccagggc caaaacccac 660
ctgaagacac ttggcgagaa agccagacct gcgctggagg acctgcgcca tagtctgatg 720
cccatgctgg agacgcttaa gaccaaagcc cagagtgtga tcgacaaggc cagcgagact 780
ctgactgccc agggcgcgcc caactgggtg aatgtaataa gtgatttgaa aaaaattgaa 840
gatcttattc aatctatgca tattgatgct actttatata cggaaagtga tgttcacccc 900
agttgcaaag taacagcaat gaagtgcttt ctcttggagt tacaagttat ttcacttgag 960
tccggagatg caagtattca tgatacagta gaaaatctga tcatcctagc aaacaacagt 1020
ttgtcttcta atgggaatgt aacagaatct ggatgcaaag aatgtgagga actggaggaa 1080
aaaaatatta aagaattttt gcagagtttt gtacatattg tccaaatgtt catcaacact 1140
tcttga 1146

<210> SEQ ID NO 41
<211> LENGTH: 1290
<212> TYPE: DNA
<213> ORGANISM: Artificial
<220> FEATURE:
<223> OTHER INFORMATION: mApoI-mIL15

<400> SEQUENCE: 41
atgaaagctg tggtgctggc cgtggctctg gtcttcctga cagggagcca ggcttggcac 60
gtatggcagc aagatgaacc ccagtcccaa tgggacaaag tgaaggattt cgctaatgtg 120
tatgtggatg cggtcaaaga cagcggcaga gactatgtgt cccagtttga atcctcctcc 180
ttgggccaac agctgaacct gaatctcctg gaaaactggg acactctggg ttcaaccgtt 240
agtcagctgc aggaacggct gggcccattg actcgggact tctgggataa cctggagaaa 300
gaaacagatt gggtgagaca ggagatgaac aaggacctag aggaagtgaa acagaaggtg 360
cagccctacc tggacgaatt ccagaagaaa tggaaagagg atgtggagct ctaccgccag 420
aaggtggcgc ctctgggcgc cgagctgcag gagagcgcgc gccagaagct gcaggagctg 480
caagggagac tgtcccctgt ggctgaggaa tttcgcgacc gcatgcgcac acacgtagac 540
tctctgcgca cacagctagc gccccacagc gaacagatgc gcgagagcct ggcccagcgc 600
ctggctgagc tcaagagcaa ccctaccttg aacgagtacc acaccagggc caaaacccac 660
ctgaagacac ttggcgagaa agccagacct gcgctggagg acctgcgcca tagtctgatg 720
cccatgctgg agacgcttaa gaccaaagcc cagagtgtga tcgacaaggc cagcgagact 780
ctgactgccc agggcgcgcc catgaaaatt ttgaaaccat atatgaggaa tacatccatc 840
tcgtgctact tgtgtttcct tctaaacagt cactttttaa ctgaggctgg cattcatgtc 900
ttcattttgg gctgtgtcag tgtaggtctc cctaaaacag aggccaactg gatagatgta 960
agatatgacc tggagaaaat tgaaagcctt attcaatcta ttcatattga caccacttta 1020
tacactgaca gtgactttca tcccagttgc aaagttactg caatgaactg ctttctcctg 1080

```
gaattgcagg ttattttaca tgagtacagt aacatgactc ttaatgaaac agtaagaaac   1140
gtgctctacc ttgcaaacag cactctgtct tctaacaaga atgtagcaga atctggctgc   1200
aaggaatgtg aggagctgga ggagaaaacc ttcacagagt ttttgcaaag ctttatacgc   1260
attgtccaaa tgttcatcaa cacgtcctga                                   1290
```

<210> SEQ ID NO 42
<211> LENGTH: 443
<212> TYPE: PRT
<213> ORGANISM: Artificial
<220> FEATURE:
<223> OTHER INFORMATION: hSushi-hIL15-hApoA1

<400> SEQUENCE: 42

```
Cys Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
                20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys Ile Arg Asp
        50                  55                  60

Gly Gly Ser Gly Gly Gly Ser Gly Gly Gly Ser Gly Gly Gly
65                  70                  75                  80

Ser Leu Gln Asn Trp Val Asn Val Ile Ser Asp Leu Lys Lys Ile Glu
                85                  90                  95

Asp Leu Ile Gln Ser Met His Ile Asp Ala Thr Leu Tyr Thr Glu Ser
            100                 105                 110

Asp Val His Pro Ser Cys Lys Val Thr Ala Met Lys Cys Phe Leu Leu
        115                 120                 125

Glu Leu Gln Val Ile Ser Leu Glu Ser Gly Asp Ala Ser Ile His Asp
130                 135                 140

Thr Val Glu Asn Leu Ile Ile Leu Ala Asn Asn Ser Leu Ser Ser Asn
145                 150                 155                 160

Gly Asn Val Thr Glu Ser Gly Cys Lys Glu Cys Glu Glu Leu Glu Glu
                165                 170                 175

Lys Asn Ile Lys Glu Phe Leu Gln Ser Phe Val His Ile Val Gln Met
            180                 185                 190

Phe Ile Asn Thr Ser Gly Ala Pro Asp Glu Pro Gln Ser Pro Trp
        195                 200                 205

Asp Arg Val Lys Asp Leu Ala Thr Val Tyr Val Asp Val Leu Lys Asp
        210                 215                 220

Ser Gly Arg Asp Tyr Val Ser Gln Phe Glu Gly Ser Ala Leu Gly Lys
225                 230                 235                 240

Gln Leu Asn Leu Lys Leu Leu Asp Asn Trp Asp Ser Val Thr Ser Thr
                245                 250                 255

Phe Ser Lys Leu Arg Glu Gln Leu Gly Pro Val Thr Gln Glu Phe Trp
            260                 265                 270

Asp Asn Leu Glu Lys Glu Thr Glu Gly Leu Arg Gln Glu Met Ser Lys
        275                 280                 285

Asp Leu Glu Glu Val Lys Ala Lys Val Gln Pro Tyr Leu Asp Asp Phe
        290                 295                 300

Gln Lys Lys Trp Gln Glu Glu Met Glu Leu Tyr Arg Gln Lys Val Glu
305                 310                 315                 320
```

Pro Leu Arg Ala Glu Leu Gln Glu Gly Ala Arg Gln Lys Leu His Glu
              325                 330                 335

Leu Gln Glu Lys Leu Ser Pro Leu Gly Glu Glu Met Arg Asp Arg Ala
          340                 345                 350

Arg Ala His Val Asp Ala Leu Arg Thr His Leu Ala Pro Tyr Ser Asp
      355                 360                 365

Glu Leu Arg Gln Arg Leu Ala Ala Arg Leu Glu Ala Leu Lys Glu Asn
  370                 375                 380

Gly Gly Ala Arg Leu Ala Glu Tyr His Ala Lys Ala Thr Glu His Leu
385                 390                 395                 400

Ser Thr Leu Ser Glu Lys Ala Lys Pro Ala Leu Glu Asp Leu Arg Gln
              405                 410                 415

Gly Leu Leu Pro Val Leu Glu Ser Phe Lys Val Ser Phe Leu Ser Ala
          420                 425                 430

Leu Glu Glu Tyr Thr Lys Lys Leu Asn Thr Gln
      435                 440

<210> SEQ ID NO 43
<211> LENGTH: 459
<212> TYPE: PRT
<213> ORGANISM: Artificial
<220> FEATURE:
<223> OTHER INFORMATION: mSushi-mIL15-mApoA1

<400> SEQUENCE: 43

Cys Pro Pro Pro Val Ser Ile Glu His Ala Asp Ile Arg Val Lys Asn
1               5                   10                  15

Tyr Ser Val Asn Ser Arg Glu Arg Tyr Val Cys Asn Ser Gly Phe Lys
              20                  25                  30

Arg Lys Ala Gly Thr Ser Thr Leu Ile Glu Cys Val Ile Asn Lys Asn
          35                  40                  45

Thr Asn Val Ala His Trp Thr Thr Pro Ser Leu Lys Cys Gly Gly Ser
      50                  55                  60

Gly Gly Gly Gly Ser Gly Gly Ser Gly Gly Gly Ser Leu Gln
65                  70                  75                  80

Thr Glu Ala Gly Ile His Val Phe Ile Leu Gly Cys Val Ser Val Gly
              85                  90                  95

Leu Pro Lys Thr Glu Ala Asn Trp Ile Asp Val Arg Tyr Asp Leu Glu
          100                 105                 110

Lys Ile Glu Ser Leu Ile Gln Ser Ile His Ile Asp Thr Thr Leu Tyr
      115                 120                 125

Thr Asp Ser Asp Phe His Pro Ser Cys Lys Val Thr Ala Met Asn Cys
  130                 135                 140

Phe Leu Leu Glu Leu Gln Val Ile Leu His Glu Tyr Ser Asn Met Thr
145                 150                 155                 160

Leu Asn Glu Thr Val Arg Asn Val Leu Tyr Leu Ala Asn Ser Thr Leu
              165                 170                 175

Ser Ser Asn Lys Asn Val Ala Glu Ser Gly Cys Lys Glu Cys Glu Glu
          180                 185                 190

Leu Glu Glu Lys Thr Phe Thr Glu Phe Leu Gln Ser Phe Ile Arg Ile
      195                 200                 205

Val Gln Met Phe Ile Asn Thr Ser Gly Ala Pro Asp Glu Pro Gln Ser
  210                 215                 220

Gln Trp Asp Lys Val Lys Asp Phe Ala Asn Val Tyr Val Asp Ala Val
225                 230                 235                 240

```
Lys Asp Ser Gly Arg Asp Tyr Val Ser Gln Phe Glu Ser Ser Ser Leu
                245                 250                 255
Gly Gln Gln Leu Asn Leu Asn Leu Leu Glu Asn Trp Asp Thr Leu Gly
            260                 265                 270
Ser Thr Val Ser Gln Leu Gln Glu Arg Leu Gly Pro Leu Thr Arg Asp
        275                 280                 285
Phe Trp Asp Asn Leu Glu Lys Glu Thr Asp Trp Val Arg Gln Glu Met
290                 295                 300
Asn Lys Asp Leu Glu Glu Val Lys Gln Lys Val Gln Pro Tyr Leu Asp
305                 310                 315                 320
Glu Phe Gln Lys Lys Trp Lys Glu Asp Val Glu Leu Tyr Arg Gln Lys
                325                 330                 335
Val Ala Pro Leu Gly Ala Glu Leu Gln Glu Ser Ala Arg Gln Lys Leu
            340                 345                 350
Gln Glu Leu Gln Gly Arg Leu Ser Pro Val Ala Glu Glu Phe Arg Asp
        355                 360                 365
Arg Met Arg Thr His Val Asp Ser Leu Arg Thr Gln Leu Ala Pro His
370                 375                 380
Ser Glu Gln Met Arg Glu Ser Leu Ala Gln Arg Leu Ala Glu Leu Lys
385                 390                 395                 400
Ser Asn Pro Thr Leu Asn Glu Tyr His Thr Arg Ala Lys Thr His Leu
                405                 410                 415
Lys Thr Leu Gly Glu Lys Ala Arg Pro Ala Leu Glu Asp Leu Arg His
            420                 425                 430
Ser Leu Met Pro Met Leu Glu Thr Leu Lys Thr Lys Ala Gln Ser Val
        435                 440                 445
Ile Asp Lys Ala Ser Glu Thr Leu Thr Ala Gln
450                 455

<210> SEQ ID NO 44
<211> LENGTH: 1428
<212> TYPE: DNA
<213> ORGANISM: Artificial
<220> FEATURE:
<223> OTHER INFORMATION: Sequence encoding a hSushi-hIL15-hApo fusion
      protein
<220> FEATURE:
<221> NAME/KEY: misc_feature
<222> LOCATION: (1)..(288)
<223> OTHER INFORMATION: Sequence encoding signal peptide and Sushi
      domain of the human IL15 receptor alpha subunit (IL15RA)
      (NM_002189.2 REGION: 83..371)
<220> FEATURE:
<221> NAME/KEY: misc_feature
<222> LOCATION: (289)..(345)
<223> OTHER INFORMATION: Sequence encoding a linker (Linker)
<220> FEATURE:
<221> NAME/KEY: misc_feature
<222> LOCATION: (346)..(687)
<223> OTHER INFORMATION: Sequence encoding mature human IL15
      (NM_172174.2 REGION: 990..1331)
<220> FEATURE:
<221> NAME/KEY: misc_feature
<222> LOCATION: (688)..(696)
<223> OTHER INFORMATION: Sequence encoding GAP linker (Linker)
<220> FEATURE:
<221> NAME/KEY: misc_feature
<222> LOCATION: (697)..(1425)
<223> OTHER INFORMATION: Sequence encoding mature human apolipoprotein
      A-I (APOA1) (NM_000039.1 REGION: 111..839)

<400> SEQUENCE: 44 atggcccgc ggcgggcgcg cggctgccgg accctcggtc tcccggcgct gctactgctg    60
```

| | |
|---|---|
| ctgctgctcc ggccgccggc gacgcggggc atcacgtgcc ctccccccat gtccgtggaa | 120 |
| cacgcagaca tctgggtcaa gagctacagc ttgtactcca gggagcgta catttgtaac | 180 |
| tctggtttca gcgtaaagc cggcacgtcc agcctgacgg agtgcgtgtt gaacaaggcc | 240 |
| acgaatgtcg cccactggac aaccccagt ctcaaatgca ttagagacgg cggctctgga | 300 |
| ggtggaggat ccggcggagg atctggcggc ggaggaagcc tgcagaactg ggtgaatgta | 360 |
| ataagtgatt tgaaaaaaat tgaagatctt attcaatcta tgcatattga tgctacttta | 420 |
| tatacggaaa gtgatgttca ccccagttgc aaagtaacag caatgaagtg ctttctcttg | 480 |
| gagttacaag ttatttcact tgagtccgga gatgcaagta ttcatgatac agtagaaaat | 540 |
| ctgatcatcc tagcaaacaa cagtttgtct tctaatggga atgtaacaga atctggatgc | 600 |
| aaagaatgtg aggaactgga ggaaaaaaat ttaaagaat ttttgcagag ttttgtacat | 660 |
| attgtccaaa tgttcatcaa cacttctggc gcgcccgatg aacccccca gagcccctgg | 720 |
| gatcgagtga aggacctggc cactgtgtac gtggatgtgc tcaaagacag cggcagagac | 780 |
| tatgtgtccc agtttgaagg ctccgccttg ggaaaacagc taaacctaaa gctccttgac | 840 |
| aactgggaca cgtgacctc caccttcagc aagctgcgcg aacagctcgg ccctgtgacc | 900 |
| caggagttct gggataacct ggaaaaggag acagagggcc tgaggcagga gatgagcaag | 960 |
| gatctggagg aggtgaaggc caaggtgcag ccctacctgg acgacttcca gaagaagtgg | 1020 |
| caggaggaga tggagctcta ccgccagaag gtggagccgc tgcgcgcaga gctccaagag | 1080 |
| ggcgcgcgcc agaagctgca cgagctgcaa gagaagctga gcccactggg cgaggagatg | 1140 |
| cgcgaccgcg cgcgcgccca tgtgacgcg ctgcgcacgc atctggcccc ctacagcgac | 1200 |
| gagctgcgcc agcgcttggc cgcgcgcctt gaggctctca aggagaacgg cggcgccaga | 1260 |
| ctggccgagt accacgccaa ggccaccgag catctgagca cgctcagcga aaggccaag | 1320 |
| cccgcgctcg aggacctccg ccaaggcctg ctgccgtgc tggagagctt caaggtcagc | 1380 |
| ttcctgagcg ctctcgagga gtacactaag aagctcaaca cccagtga | 1428 |

<210> SEQ ID NO 45
<211> LENGTH: 1407
<212> TYPE: DNA
<213> ORGANISM: Artificial
<220> FEATURE:
<223> OTHER INFORMATION: mSushi-mIL15-mApoA1 cDNA

<400> SEQUENCE: 45

| | |
|---|---|
| atggagacag acaccctgct gctctgggtg ctgctgctgt gggtgcccgg ctctaccggc | 60 |
| gacggcacca cctgccctcc ccctgtgtcc atcgagcacg ccgacatcag agtgaagaac | 120 |
| tactccgtga actctcggga gagatacgtg tgcaactccg gcttcaagcg gaaggccggc | 180 |
| acctccaccc tgatcgagtg cgtgatcaac aagaacacca acgtggccca ctggaccacc | 240 |
| ccttccctga gtgcatccg ggacccttcc ggcggctctg aggtggagg atccggcgga | 300 |
| ggatctggcg gcggaggaag cctgcaggag ccaactgga tcgacgtgcg ctacgacctg | 360 |
| gagaagatcg agtccctgat ccagtccatc cacatcgaca ccaccctgta caccgactcc | 420 |
| gacttccacc cttcctgcaa ggtgaccgcc atgaactgct tctgctgga gctgcaggtg | 480 |
| atcctgcacg agtactccaa catgaccctg aacgagacag tgcggaacgt gctgtacctg | 540 |
| gccaactcca ccctgtcctc caacaagaac gtggccgagt ccggctgcaa ggagtgcgag | 600 |
| gagctggagg agaagacctt caccgagttt ctgcagtcct tcatccggat cgtgcagatg | 660 |
| ttcatcaaca ccagcggcgc gcccgatgaa cccccagtccc aatgggacaa agtgaaggat | 720 |

-continued

```
ttcgctaatg tgtatgtgga tgcggtcaaa gacagcggca gagactatgt gtcccagttt      780
gaatcctcct ccttgggcca acagctgaac ctgaatctcc tggaaaactg ggacactctg      840
ggttcaaccg ttagtcagct gcaggaacgg ctgggcccat tgactcggga cttctgggat      900
aacctggaga agaaaacaga ttgggtgaga caggagatga acaaggacct agaggaagtg      960
aaacagaagg tgcagcccta cctggacgaa ttccagaaga atggaaaga ggatgtggag     1020 ctctaccgcc agaaggtggc gcctctgggc gccgagctgc aggagagcgc gcgccagaag    1080
ctgcaggagc tgcaagggag actgtcccct gtggctgagg aatttcgcga ccgcatgcgc    1140
acacacgtag actctctgcg cacacagcta gcgccccaca gcgaacagat gcgcgagagc    1200
ctggcccagc gcctggctga gctcaagagc aaccctacct tgaacgagta ccacaccagg    1260
gccaaaaccc acctgaagac acttggcgag aaagccagac ctgcgctgga ggacctgcgc    1320
catagtctga tgcccatgct ggagacgctt aagaccaaag cccagagtgt gatcgacaag    1380
gccagcgaga ctctgactgc ccagtga                                        1407
```

<210> SEQ ID NO 46
<211> LENGTH: 20
<212> TYPE: DNA
<213> ORGANISM: Artificial
<220> FEATURE:
<223> OTHER INFORMATION: FwATGmApoA1 primer

<400> SEQUENCE: 46

```
atgaaagctg tggtgctggc                                                  20
```

<210> SEQ ID NO 47
<211> LENGTH: 20
<212> TYPE: DNA
<213> ORGANISM: Artificial
<220> FEATURE:
<223> OTHER INFORMATION: RvTGAmApoA1 primer

<400> SEQUENCE: 47

```
tcactgggca gtcagagtct                                                  20
```

<210> SEQ ID NO 48
<211> LENGTH: 28
<212> TYPE: DNA
<213> ORGANISM: Artificial
<220> FEATURE:
<223> OTHER INFORMATION: FwAscIhIL15 primer

<400> SEQUENCE: 48

```
aataatggcg cgccgaactg gatagatg                                         28
```

<210> SEQ ID NO 49
<211> LENGTH: 27
<212> TYPE: DNA
<213> ORGANISM: Artificial
<220> FEATURE:
<223> OTHER INFORMATION: RvNotIhIL15 primer

<400> SEQUENCE: 49

```
gttcatcaac acgtcctgag cggccgc                                          27
```

<210> SEQ ID NO 50
<211> LENGTH: 28
<212> TYPE: DNA
<213> ORGANISM: Artificial
<220> FEATURE:

```
<223> OTHER INFORMATION: RvAscImApoA1 primer

<400> SEQUENCE: 50
ggcgcgccct gggcagtcag agtctcgc                                              28

<210> SEQ ID NO 51
<211> LENGTH: 21
<212> TYPE: DNA
<213> ORGANISM: Artificial
<220> FEATURE:
<223> OTHER INFORMATION: Fw Sushi primer

<400> SEQUENCE: 51
atggagacag acaccctgct g                                                     21

<210> SEQ ID NO 52
<211> LENGTH: 27
<212> TYPE: DNA
<213> ORGANISM: Artificial
<220> FEATURE:
<223> OTHER INFORMATION: Rv IL15 AscI primer

<400> SEQUENCE: 52
gggcgcgccg ctggtgttga tgaacat                                               27
```